(12) United States Patent
Skolnick et al.

(10) Patent No.: US 8,138,377 B2
(45) Date of Patent: Mar. 20, 2012

(54) ARYLBICYCLO[3.1.0]HEXYLAMINES AND METHODS AND COMPOSITIONS FOR THEIR PREPARATION AND USE

(75) Inventors: Phil Skolnick, Edgewater, NJ (US); Zhengming Chen, Belle Meade, NJ (US); Ji Yang, Princeton Junction, NJ (US)

(73) Assignee: DOV Pharmaceutical, Inc., Somerset, NJ (US)

( * ) Notice: Subject to any disclaimer, the term of this patent is extended or adjusted under 35 U.S.C. 154(b) by 1027 days.

(21) Appl. No.: 11/936,016

(22) Filed: Nov. 6, 2007

(65) Prior Publication Data

US 2008/0293822 A1 Nov. 27, 2008

(51) Int. Cl.
*C07C 211/00* (2006.01)
(52) U.S. Cl. .................... 564/460; 564/308; 564/426
(58) Field of Classification Search .................. 532/460, 532/308, 426
See application file for complete search history.

(56) References Cited

U.S. PATENT DOCUMENTS

| | | | |
|---|---|---|---|
| 3,892,722 A | 7/1975 | Babitsky et al. | |
| 4,022,652 A | 5/1977 | Hirano et al. | |
| 4,088,652 A | 5/1978 | Fanshawe et al. | |
| 4,118,393 A | 10/1978 | Fanshawe et al. | |
| 4,118,417 A | 10/1978 | Epstein | |
| 4,131,611 A | 12/1978 | Fanshawe et al. | |
| 4,196,120 A | 4/1980 | Fanshawe et al. | |
| 4,231,935 A | 11/1980 | Fanshawe et al. | |
| 4,336,268 A | 6/1982 | Bruderer et al. | |
| 4,435,419 A | 3/1984 | Epstein et al. | |
| 4,467,102 A | 8/1984 | Toda et al. | |
| 4,504,657 A | 3/1985 | Bouzard et al. | |
| 4,521,431 A | 6/1985 | Crookes | |
| 4,591,598 A | 5/1986 | Urbach et al. | |
| 5,039,680 A | 8/1991 | Imperato et al. | |
| 5,075,341 A | 12/1991 | Mendelson et al. | |
| 5,130,430 A | 7/1992 | Shaw | |
| 5,198,459 A | 3/1993 | Imperato et al. | |
| 5,232,934 A | 8/1993 | Downs | |
| 5,488,056 A | 1/1996 | Bodick et al. | |
| 5,556,837 A | 9/1996 | Nestler et al. | |
| 5,556,838 A | 9/1996 | Mayer et al. | |
| 5,574,052 A | 11/1996 | Rose et al. | |
| 5,672,360 A | 9/1997 | Sackler et al. | |
| 5,762,925 A | 6/1998 | Sagen | |
| 5,911,992 A | 6/1999 | Braswell et al. | |
| 5,916,920 A | 6/1999 | Fernandez et al. | |
| 5,969,156 A | 10/1999 | Briggs et al. | |
| 5,985,864 A | 11/1999 | Imai et al. | |
| 6,109,269 A | 8/2000 | Rise et al. | |
| 6,121,261 A | 9/2000 | Glatt et al. | |
| 6,194,000 B1 | 2/2001 | Smith et al. | |
| 6,204,284 B1 | 3/2001 | Beer et al. | |
| 6,245,357 B1 | 6/2001 | Edgren et al. | |
| 6,245,911 B1 | 6/2001 | Imai et al. | |
| 6,268,507 B1 | 7/2001 | Massey et al. | |
| 6,372,919 B1 | 4/2002 | Lippa et al. | |
| 6,569,887 B2 | 5/2003 | Lippa et al. | |
| 6,716,868 B2 | 4/2004 | Lippa et al. | |
| 7,041,835 B2 | 5/2006 | Lippa et al. | |
| 7,081,471 B2 | 7/2006 | Lippa et al. | |
| 7,094,799 B2 | 8/2006 | Russell et al. | |
| 7,098,229 B2 | 8/2006 | Lippa et al. | |
| 7,098,230 B2 | 8/2006 | Lippa et al. | |
| 2004/0122017 A1 | 6/2004 | Clader et al. | |
| 2004/0127541 A1 | 7/2004 | Codd et al. | |
| 2006/0223875 A1 | 10/2006 | Skolnick et al. | |
| 2008/0269348 A1 | 10/2008 | Skolnick et al. | |

FOREIGN PATENT DOCUMENTS

| | | |
|---|---|---|
| BE | 858683 | 3/1978 |
| BE | 893707 | 12/1982 |
| WO | WO-03/047568 A1 | 6/2003 |
| WO | WO2005080382 | 9/2005 |
| WO | WO2006108701 | 10/2005 |
| WO | WO-2006/023659 A2 | 3/2006 |
| WO | WO-2006/096810 A2 | 9/2006 |
| WO | WO-2007/016155 A2 | 2/2007 |
| WO | WO2007022933 | 3/2007 |
| WO | WO2007022934 | 3/2007 |
| WO | WO2007022980 | 3/2007 |

OTHER PUBLICATIONS

Richard Wang, et al, The Oral Analgesic Efficacy of Bicifadine Hydrochloride in Postoperative Pain, 22 J Clin. Pharmacol. 160 (1982).*

Baldessarini, R. *Drugs and The Treatment of Psychiatric Disorders.* Goodman & Gilman's The Pharmacological Basis of Therapeutics 9th Edition. Harman et al. eds. 1996. p. 399 and Ch 18:431-459, McGraw-Hill, New York.

Bayes, et al., *Gateways to Clinical Trial*. Methods Find Exp. Clin. Pharmacol. Apr. 2003; 25(3):225-248.

Beer, et al *DOV 216,303, a "Triple" Reupdate Inhibitor: Safety, Tolerability, and Pharmacokinetic Profile*, J. Clin. Pharmacol. 44:1360-1367, 2004.

Blum, et al., *Dopamine D2 Receptor Gene Variants; Association and Linkage Studies in Impulsive-Addictive-Compulsive Behavior.* Pharmacogenetics 5:121-141, 1996.

Bray, G. *A Concise Review on the Therapeutics of Obesity.* Nutrition 16:953-960, 2000.

Crown, W. *Economic Outcomes Associated With Tricyclic Antidepressant and Selective Serotonin Reuptate Inhibitor Treatments for Depression.* Acta Psychiatr. Supp. 2000; 403:62-6.

Czobor, P. *A Double-Blind, Placebo Controlled Randomized Study of DOV 220,075 (Bicifadine) SR and Codeine 60 mg in The Treatment of Post-Operative Dental Pain.* Abstract (915). American Pain Society (2003).

(Continued)

*Primary Examiner* — Karlheinz R Skowronek
*Assistant Examiner* — Sean Basquill
(74) *Attorney, Agent, or Firm* — Jeffrey J. King; Patent Networks Law Group PLLC

(57) ABSTRACT

The invention provides novel arylbicyclo[3.1.0]hexylamines, and related processes and intermediates for preparing these compounds, as well as compositions and methods employing these compounds for the treatment and/or prevention of central nervous system (CNS) disorders, including but not limited to depression and anxiety.

2 Claims, No Drawings

OTHER PUBLICATIONS

Czobor, P. *A Two Center Double-Blind, Placebo-Controlled Randomized Study of DOV 220,075 (Bicifadine) SR and Tramadol 100 mg in The Treatment of Post-Operative Dental Pain.* Abstract (801). American Pain Society (2004).

D'Aquila, et al, *The Role of Dopoamine in The Mechanism of Action of Antidepressant Drugs.* Eur. J. Pharmacol. 405:365-373, 2000.

Epstein, et al., *1-Aryl-3-Azabicyclo[3.1.0]Hexanes, A New Series of Non-Narcotic Analgesic Agents.* J. Med. Chem. 24(5):481-90, 1981.

Epstein, et al., *Bicifadine: Non-Narcotic Analgesic Activity of 1-Aryl-3-Azabicyclo[3.1.0]Hexanes.* NIDA Res. Monogr. 41:93-98, 1982.

Frazer, A. *Norepinephrine Involvement in Antidepressant Action.* J. Clin. Psychiatry. 61(10):25-30, 2000.

Fredman, et al., *Partial Response, Nonresponse, and Relapse With Selective Serotonin Reuptake Inhibitors in Major Depression: A Survey of Current "Next-Step" Practices.* J. Clin. Psychiatry 61(6):403-8, 2000.

Hackh's *Chemical Dictionary*, 4th Edition, 1969, Julius Grant, ed., McGraw-Hill Book Company, New York, pp. 474-75.

Harrison's *Principles of Internal Medicine* 2485-2503 (Fauci, et al., eds., 14th ed. 1998).

Hitri, et al., *Molecular, Functional and Bilchemical Characteristics of The Dopamine Transporter: Regional Differences and Clinical Relevance.* J. Clin. Pharmacol. 17:1-22, 1994.

Hoffman, et al., *Localization and Dynamic Regulation of Biogenic Amine Transporters in the Mammalian Central Nevous System.* Front. In Neuroendocrinol. 19(3): 187-213, 1998.

Kiyatkin, E. *Dopamine Mechanisms of Cocaine Addition.* Int. J. Neurosci. 78:75-101, 1994.

Kreek, M. *Cocaine, Dopamine and The Endogenous Opiod Systems.* J. Addict. Dis. 15:73-96, 1996.

Leonhardt, et al., *New Approaches in the Pharmacological Treatment of Obesity.* Eur. J. Nutr. 38:1-13, 1999.

McArdle, et al., "*A Method for the Prediction of the Crystal Structure of Ionic Compounds—The Crystal Structures of O-Toluidinium Chloride and Bromide and Polymorphism of Bicifadine Hydrochloride.*" Cryst.Enc.Comm. 2004; 6(53):303-309.

Meyerson, et al., *Allosteric Interation Between the Site Labeled by [3H]imipramine and the Serotonin Transporter in Human Platelets.* J. Neurochem. 48(2):560-65, 1987.

Nagatsu, et al., *changes in Cytokines and Neorotrophins in Parkinson's Disease.* J. Neural. Transm. Suppl. 60:277-290 2000.

Noble, E. *Polymorphisms of the D2 Dopamine Receptor Gene and Alcoholism and Other Substance Use Disorders.* Alcohol. Supp. 2:35-43, 1994.

Porter, et al., *Single Dose Comparison of Bicifadine, Codeine, and Placebo in Postoperative Pain.* Current Therapeutic Research. 30(3):156-160, Aug. 1981.

Scates, et al., *Reboxetine: A Selective Norepinephrine Reuptate Inhibitor for the Treatment of Depression.* Ann. Pharmacother. 34(11):1302-12, 2000.

Simon, et al., *TCAs or SSRIs As Initial Therapy for Depression?* J. of Family Practice. 48:845-46. 1999.

Skolnick, et al., "*Broad Spectrum" Antidepressants: Is More Better for the Treatment of Depression?* Life Sciences 73 (2003) 3175-3179.

Skolnick, P., *Beyond Monoamine-Based Therapies: Clues to New Approaches.* J. Clin Psychiatry 63:19-23, 2002.

Stacy, et al., *Treatment Options for Early Parkinson's Disease.* Am. Fam. Phys. 53:1281-87, 1996.

Sullivan, et al., *Mechanisms of Appetite Modulation by Drugs*, Federation Proceedings, vol. 44, No. 1, Part 1, pp. 139-144, 1985.

Wang, et al., *The Oral Analgesic Efficacy of Bicifadine Hydrochloride in Postoperative Pain.* J. Clin. Pharmacol. 22(4):160-164, Apr. 1982.

Wong, et al., *Reboxetine: A Pharmacologically Potent, Selective, and Specific Norepinephrine Reuptake Inhibitor.* Biol. Psychiatry. 47(9):818-29, 2000.

Skolnick, et al, (2003) Antidepressant-like Actions of DOV 21, 947, A "Triple" Uptake Inhibitor. European Journal of Pharmacology 461 (2003) 99-104.

Morissette, et al (2004) Advanced Drug Delivery Reviews. 56: 275-300.

Vippagunta, et al (2001) Advanced Drug Delivery Reviews. 48:3-26.

Stella, Valentino J., (2004) Expert Opinion of Therapeutic Patents, Prodrugs As Therapeutics. 14(3): 277-280.

Wolff, et al., (1994) Burger's Medicinal Chemistry, 5th Ed., vol. 1, pp. 975-977.

Testa, Bernard (2004) Biochemical Pharmacology, Prodrug Research : Futile or Fertile? 68: 2097-2106.

Ettmayer, Peter., (2004), Medicinal Chemistry, Lessons Learned From Merketed and Investigational Prodrugs. 47(10): 2394-2404.

Xu, et al, (2006), Stereocontrolled Syn. of Trisubstitited Cyclepropanes: Expedient, Atom-Economical, Asymmetric Syn. of (+)-Bicifadine & DOV21947. Org. Lett. 17:8(17):3885-8.

Caira, M. R.,Crystalline Polymorphism of Organic Compounds, Topics in Current Chemistry,1998, vol. 198:1998,163-208,DIO:10.1007/3-540-69178-2-5.

Casadio, et al, Acide Phenyl-1-Hydroxymethyl-2-Cyclopropane Carboxylique Et Derives, Boll. Chim. Farm., 117 1978.

Pain Therapies Take Different Path Improving Long-Term Pain Relief by Reducing Dependency and Tolerance, Genetic Engineering &Biotechnology News—vol. 26/12, 2006.

Drug Delivery Fuels Specialty Pharma-Rich Source of Innovation Now Significant Platform to Launch New Companies Genetic Engineering&Biotechnology News—vol. 27/10, 2007.

Lima, et al., Bioisosterism:A Useful Strategy for Molecular Modification and Drug Design, Current Medical Chemistry (2005) 12,23-49.

McBriar, et al., Discovery of Bicycloalkyl Jrea Melanin Concentrating Hormone Receptor Antagonists:Orally Efficacious Antiobesity Therapeutics, J. Med. Chem. 2005,48,2274-2277.

McBriar,et al.,Discovery of Orally Efficacious Melanin-Concentrating Hormone Receptor-1 Antagonists As Antiobesity Agents. J.Med. Chem. 2006,49,2294-2310.

McMillen, et al.,Effect of DOV 102677 on the Volitional Consumption of Ethanol by Myers' High Ethanol-Preferring Rat, Alcohol Clin.Exp.Res.vol. 31,No. 11,2007: pp. 1186-1871.

Micheli, et al., A New Series of Potent and Selective Triple Reuptake Inhibitors, J. Med. Chem. Dec. 9, 2009.

Shuto, et al., Synthesis of (+)-And(−)-Milnaciprans and Their Conformationally Restricted Analogs, Tetrahedon Letters, vol. 37, No. 5, pp. 641-644, 1996.

Taylor, et al., Scales for the Identification of Adults With ADHD: A Systematic Review, Research in Developmental Disabilities 32(2011)924-938.

Zhang, et al., Studies on the Structure-Activity Relationship of Bicifadine Analogs As Monoamine Transporter Inhibitors, Bioorganic & Chemistry Letters 18(208)3682-3686.

* cited by examiner

ARYLBICYCLO[3.1.0]HEXYLAMINES AND METHODS AND COMPOSITIONS FOR THEIR PREPARATION AND USE

TECHNICAL FIELD

The present invention relates to novel arylbicyclo[3.1.0]hexylamines, methods for their production and their use for treating disorders of the central nervous system (CNS), including neuropsychiatric disorders.

BACKGROUND OF THE INVENTION

Monoamine reuptake inhibitors increase the extracellular levels of monoamine neurotransmitter, i.e. norepinephrine, serotonin and dopamine, causing a cascade of intracellular neurochemical changes that eventually lead to the desired therapeutic CNS effect (Bymaster et al., *Neuropsychopharmacology* 27:699-711. (2002); Richelson, *J. Clin. Psychiatry.* 64:5-12. (2003)). These reuptake inhibitors have potential uses as medications in a wide variety of neuropsychiatric disorders ranging from anxiety and depression to eating disorders and drug or alcohol addiction. One potential use is as antidepressants. Selective serotonin reuptake inhibitors (SSRIs), e.g. fluoxetine (Prozac®) and sertraline (Zoloft®), and serotonin and norepinephrine reuptake inhibitors (SNRIs), e.g. venlafaxine (Effexor®), and duloxetine (Cymbalta®), have been widely applied to treat depression and anxiety disorders. There is increasing evidence from both preclinical and clinical studies showing that simultaneous blockage of reuptake of serotonin, norepinephrine, and dopamine may achieve better desired effects than using single or dual reuptake inhibitors. (Skolnick, *J. Clin. Psychiatry.* 63 (suppl. 2): 19-23. (2002)) In this context, compounds having "broad spectrum" inhibition of monoamine reuptake may yield a more rapid onset and/or higher efficacy of antidepressant activity than currently available antidepressants, including agents that inhibit single or dual reuptake of serotonin and/or norepinephrine (Skolnick et al., *Eur. J. Pharmacol.* 461:99 (2003); Skolnick, P., Popik, P., Janowsky, A., Beer, B., and Lippa, A. S.: "Broad spectrum" antidepressants: Is more better for the treatment of depression? *Life Sci.,* 73: 3175-3179, 2003).

In view of the limited availability and understanding of currently-known "broad spectrum antidepressants", there remains a compelling need in the art to identify additional drugs having multiple reuptake inhibitory potential for inhibiting reuptake of multiple biogenic amines linked to disorders of the central nervous system (CNS), including neuropsychiatric disorders, such as depression and anxiety.

It is therefore an object of the present invention to provide novel compounds having activity to inhibit reuptake of one or multiple biogenic amines linked to CNS disorders, and to provide related compositions, and methods for treating and managing CNS disorders, including depression and anxiety.

SUMMARY OF EXEMPLARY EMBODIMENTS OF THE INVENTION

It is therefore an object of the present invention to provide novel compounds capable of inhibiting the reuptake of multiple biogenic amines linked to CNS disorders, and to provide related compositions and methods for treating and managing CNS disorders, including depression and anxiety.

It is a further object of the present invention to produce and select novel arylbicyclo[3.1.0]hexylamines as therapeutic agents.

It is another object of the invention to provide new synthetic methods and compositions useful for producing arylbicyclo[3.1.0]hexylamines and related compounds.

It is an additional object of the invention to provide novel arylbicyclo[3.1.0]hexylamine compositions and methods useful to treat or manage CNS disorders by modulating transport of one or more biogenic amines, for example to simultaneously inhibit or block the reuptake of norepinephrine and/or serotonin and/or dopamine.

The invention achieves these objects and satisfies additional objects and advantages by providing novel arylbicyclo[3.1.0]hexylamines that possess unexpected activities for modulating biogenic amine transport.

In certain embodiments of the invention, novel arylbicyclo[3.1.0]hexylamines are provided that are substituted with a napthyl group.

In exemplary embodiments, novel arylbicyclo[3.1.0]hexylamines are provided that have the following formula I:

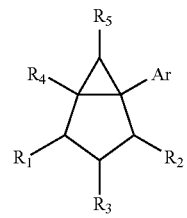

Formula I and enantiomers and pharmaceutically acceptable salts thereof, wherein:

Ar is a phenyl, a naphthyl or an aryl heterocycle group which is unsubstituted or substituted with one or more substituents selected from fluoro, chloro, bromo, iodo, $-NO_2$, $-CN$, $-NH_2$, $C_{1-8}$ alkyl, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxyl, $C_{1-3}$ alkoxy($C_{1-3}$)alkyl, carboxy($C_{1-3}$)alkyl, $C_{1-3}$ alkanoyl, halo($C_{1-3}$)alkoxyl, $C_{1-8}$ alkylamino, and di($C_{1-8}$) alkylamino; and $R_1$, $R_2$, $R_3$, $R_4$ and $R_5$ are independently hydrogen or

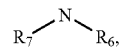

wherein $R_6$ and $R_7$ are independently selected from hydrogen, unsubstituted $C_{1-10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy;

with the proviso that one of $R_1$, $R_2$, $R_3$, $R_4$ and $R_5$ is and must be

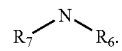

Useful arylbicyclo[3.1.0]hexylamines of the invention include the substituted arylbicyclo[3.1.0]hexylamines compounds described herein, as well as their pharmaceutically acceptable salts, enantiomers, polymorphs, solvates, hydrates, prodrugs, or combinations thereof.

The invention also provides novel methods of making arylbicyclo[3.1.0]hexylamines including synthetic methods that form novel intermediate compounds of the invention for producing arylbicyclo[3.1.0]hexylamines. In related embodiments, the invention provides novel processes for preparing arylbicyclo[3.1.0]hexylamines, to yield novel compounds useful in biologically active and/or therapeutic compositions.

In yet additional embodiments, the invention provides pharmaceutical compositions and methods for treating disorders of the central nervous system (CNS), including a wide array of serious neurological or psychiatric conditions, in mammals that are amenable to treatment using agents that inhibit or otherwise modulate biogenic amine transport.

The foregoing objects and additional objects, features, aspects and advantages of the present invention are further exemplified and described in the following detailed description.

DETAILED DESCRIPTION OF EXEMPLARY EMBODIMENTS OF THE INVENTION

The present invention fulfills these needs and satisfies additional objects and advantages by providing novel arylbicyclo[3.1.0]hexylamines as therapeutic agents to treat and manage a wide variety of disorders of the central nervous system (CNS), including neuropsychiatric disorders. CNS disorders for treatment using the compositions and methods of the invention are amenable to treatment, prophylaxis, and/or alleviation of the disorder and/or associated symptom(s) by inhibiting reuptake of multiple biogenic amines causally linked to the targeted CNS disorder, wherein the biogenic amines targeted for reuptake inhibition are selected from norepinephrine, and/or serotonin, and/or dopamine. In exemplary embodiments, the novel compounds of the invention are employed in effective compositions and methods for treating a neuropsychiatric disorder, such as depression or anxiety.

In one embodiment, the present invention provides compounds of the following formula I:

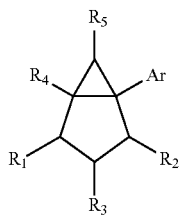

Formula I and enantiomers and pharmaceutically acceptable salts thereof, wherein:

Ar is a phenyl, a naphthyl or an aryl heterocycle group which is unsubstituted or substituted with one or more substituents selected from fluoro, chloro, bromo, iodo, —$NO_2$, —CN, —$NH_2$, $C_{1-8}$ alkyl, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxyl, $C_{1-3}$ alkoxy($C_{1-3}$)alkyl, carboxy($C_{1-3}$)alkyl, $C_{1-3}$ alkanoyl, halo($C_{1-3}$)alkoxyl, $C_{1-8}$ alkylamino, and di($C_{1-8}$) alkylamino; and $R_1$, $R_2$, $R_3$, $R_4$ and $R_5$ are independently hydrogen or

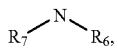

wherein $R_6$ and $R_7$ are independently selected from hydrogen, unsubstituted $C_{1-10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy;

with the proviso that one of $R_1$, $R_2$, $R_3$, $R_4$ and $R_5$ is and must be

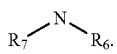

In certain embodiments, Ar is 4-methylphenyl or 3,4-dichlorophenyl, $R_4$ and $R_5$ are hydrogen and $R_1$, $R_2$ and $R_3$ are independently hydrogen or

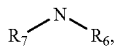

wherein $R_6$ and $R_7$ are independently selected from hydrogen and methyl, with the proviso that one of $R_1$, $R_2$ and $R_3$ is and must be

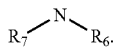

In additional embodiments, Ar is a napthyl group, $R_2$, $R_4$ and $R_5$ are hydrogen and $R_1$ and $R_3$ are independently hydrogen or

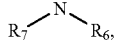

wherein $R_6$ and $R_7$ are independently selected from hydrogen and methyl, with the proviso that one of $R_1$ and $R_3$ is and must be

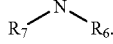

Within exemplary embodiments, the invention provides an assemblage of novel arylbicyclo[3.1.0]hexylamines with or without substitution(s) on the aryl ring. Novel arylbicyclo[3.1.0]hexylamines of the invention include the following, exemplary compounds, which have been made and characterized as illustrative embodiments of the invention (Table 1).

TABLE 1

Exemplary arylbicyclo[3.1.0]hexylamines 1-p-tolylbicyclo[3.1.0]hexan-2-amine

N-methyl-1-p-tolylbicyclo[3.1.0]hexan-2-amine

N,N-dimethyl-1-p-tolylbicyclo[3.1.0]hexan-2-amine 1-(3,4-dichlorophenyl)bicyclo[3.1.0]hexan-2-amine 1-(3,4-dichlorophenyl)-N-methylbicyclo[3.1.0]hexan-2-amine 1-(3,4-dichlorophenyl)-N,N-dimethylbicyclo[3.1.0]hexan-2-amine 1-p-tolylbicyclo[3.1.0]hexan-3-amine TABLE 1-continued Exemplary arylbicyclo[3.1.0]hexylamines N-methyl-1-p-tolylbicyclo[3.1.0]hexan-3-amine N,N-dimethyl-1-p-tolylbicyclo[3.1.0]hexan-3-amine 1-(3,4-dichlorophenyl)bicyclo[3.1.0]hexan-3-amine 1-(3,4-dichlorophenyl)-N-methylbicyclo[3.1.0]hexan-3-amine 1-(3,4-dichlorophenyl)-N,N-dimethylbicyclo[3.1.0]hexan-3-amine N-methyl-1-(naphthalen-1-yl)bicyclo[3.1.0]hexan-3-amine TABLE 1-continued Exemplary arylbicyclo[3.1.0]hexylamines

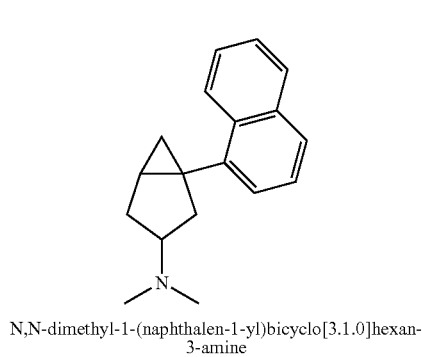

N,N-dimethyl-1-(naphthalen-1-yl)bicyclo[3.1.0]hexan-3-amine

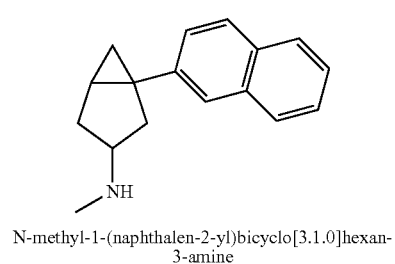

N-methyl-1-(naphthalen-2-yl)bicyclo[3.1.0]hexan-3-amine

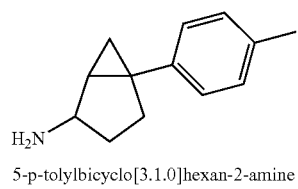

5-p-tolylbicyclo[3.1.0]hexan-2-amine

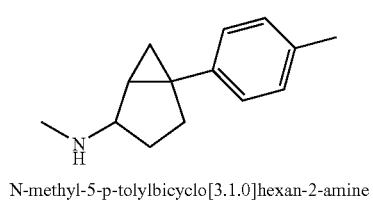

N-methyl-5-p-tolylbicyclo[3.1.0]hexan-2-amine

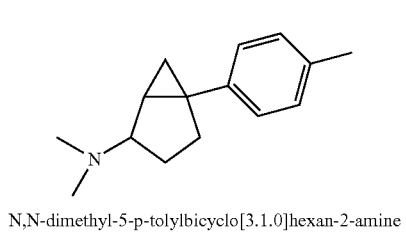

N,N-dimethyl-5-p-tolylbicyclo[3.1.0]hexan-2-amine

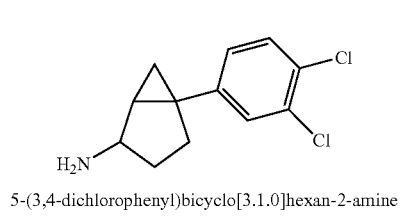

5-(3,4-dichlorophenyl)bicyclo[3.1.0]hexan-2-amine

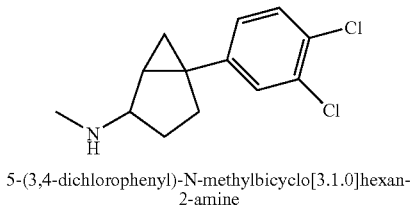

5-(3,4-dichlorophenyl)-N-methylbicyclo[3.1.0]hexan-2-amine

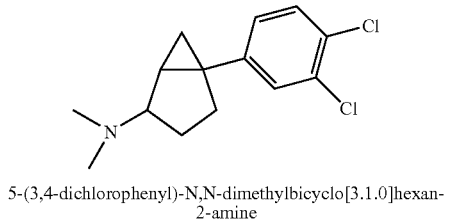

5-(3,4-dichlorophenyl)-N,N-dimethylbicyclo[3.1.0]hexan-2-amine

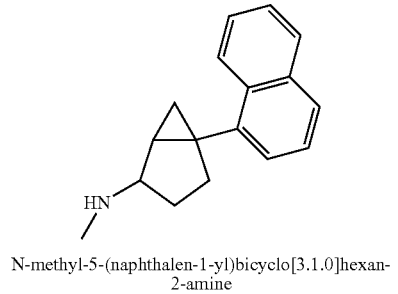

N-methyl-5-(naphthalen-1-yl)bicyclo[3.1.0]hexan-2-amine

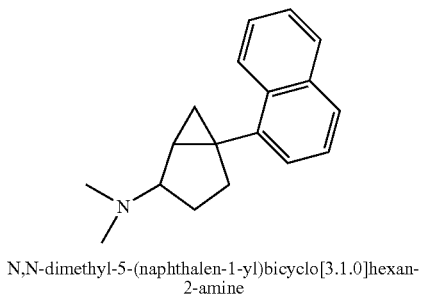

N,N-dimethyl-5-(naphthalen-1-yl)bicyclo[3.1.0]hexan-2-amine

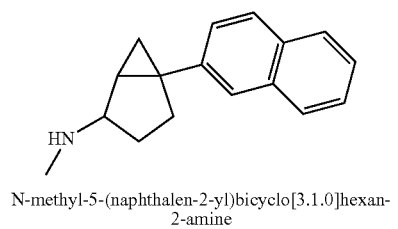

N-methyl-5-(naphthalen-2-yl)bicyclo[3.1.0]hexan-2-amine

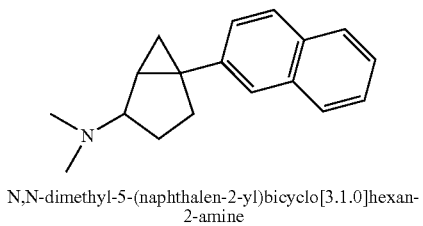

N,N-dimethyl-5-(naphthalen-2-yl)bicyclo[3.1.0]hexan-2-amine

TABLE 1-continued

Exemplary arylbicyclo[3.1.0]hexylamines

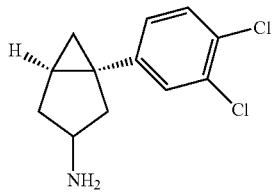

(1R,5R)-1-(3,4-dichlorophenyl)bicyclo[3.1.0]hexan-3-amine

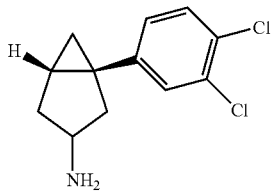

(1S,5S)-1-(3,4-dichlorophenyl)bicyclo[3.1.0]hexan-3-amine

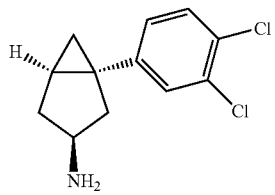

(1R,3S,5R)-1-(3,4-dichlorophenyl)bicyclo[3.1.0]hexan-3-amine

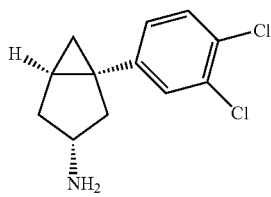

(1R,3R,5R)-1-(3,4-dichlorophenyl)bicyclo[3.1.0]hexan-3-amine

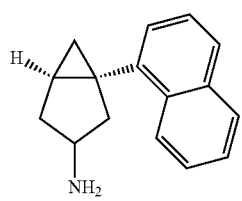

(1R,5R)-1-(naphthalen-1-yl)bicyclo[3.1.0]hexan-3-amine

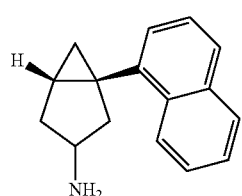

(1S,5S)-1-(naphthalen-1-yl)bicyclo[3.1.0]hexan-3-amine

TABLE 1-continued

Exemplary arylbicyclo[3.1.0]hexylamines

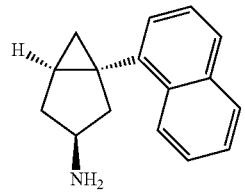

(1R,3S,5R)-1-(naphthalen-1-yl)bicyclo[3.1.0]hexan-3-amine

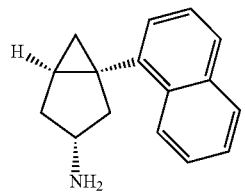

(1R,3R,5R)-1-(naphthalen-1-yl)bicyclo[3.1.0]hexan-3-amine

It will be understood that the exemplary compounds identified in Table 1 are illustrative, and that the subject modifications comprising aryl substitutions can be varied to comprise other substituents, can include yet additional substituents (i.e., three or more substitutions on the aryl ring), combined with one another, or additionally combined with or without substitutions on the nitrogen atom as described herein, to yield yet additional compounds within the invention for treating CNS disorders (including a range of neuropsychiatric disorders, such as depression and anxiety). For example, the invention provides an illustrative assemblage of novel 1-arylbicyclo[3.1.0]hexane-3-amines having multiple substitutions, (e.g., as illustrated by multiple chloro substitutions) on the aryl ring, combined with or without substitution(s) on the nitrogen atom. In another example, the invention provides an illustrative assemblage of novel 5-arylbicyclo[3.1.0]hexane-2-amines having multiple substitutions, (e.g., as illustrated by multiple chloro substitutions) on the aryl ring, combined with or without substitution(s) on the nitrogen atom. In a further example, the invention provides an illustrative assemblage of novel 1-arylbicyclo[3.1.0]hexane-2-amines having multiple substitutions, (e.g., as illustrated by multiple chloro substitutions) on the aryl ring, combined with or without substitution(s) on the nitrogen atom. Additionally, useful arylbicyclo[3.1.0]hexylamines of the invention include the substituted arylbicyclo[3.1.0]hexylamines compounds described herein, as well as their pharmaceutically acceptable salts, enantiomers, polymorphs, solvates, hydrate or prodrugs or combinations thereof.

Within related aspects of the invention, enantiomeric forms of the novel compounds described herein, having chiral symmetric structures, are provided, which provide yet additional drug candidates for treating CNS disorders. In certain embodiments, the invention provides enantiomers, diastereomers, and other stereoisomeric forms of the disclosed compounds, including racemic and resolved forms and mixtures thereof. The individual enantiomers may be separated according to methods that are well known to those of ordinary skill in the art. In other embodiments, the enantiomers, diastereomers and other stereoisomeric forms of the disclosed compounds contain no more than about 10%, about 5%, about 2% or about 1% of the corresponding enantiomers, diastereomers and stereoisomers. When the compounds described herein contain olefinic double bonds or other centers of geometric asymmetry, and unless specified otherwise, it is intended to include both E and Z geometric isomers. All tautomers are intended to be encompassed by the present invention as well.

As noted above, in certain embodiments, the invention provides pharmaceutically acceptable acid addition and base salts of the disclosed compounds. Suitable acid addition salts are formed from acids, which form non-toxic salts and include, for example, hydrochloride, hydrobromide, hydroiodide, sulphate, hydrogen sulphate, nitrate, phosphate, and hydrogen phosphate salts. Other examples of pharmaceutically acceptable addition salts include inorganic and organic acid addition salts. Additional pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; organic acid salts such as acetate, citrate, lactate, succinate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate, tartrate, gluconate and the like. Suitable base salts are formed from bases, which form non-toxic salts and include, for example, aluminum, calcium, lithium, magnesium, potassium, sodium, zinc and diethanolamine salts.

In other detailed embodiments, the invention provides prodrugs of the disclosed compounds. Prodrugs are considered to be any covalently bonded carriers which release the active parent drug in vivo. Examples of prodrugs include esters or amides of a compound of the present invention with hydroxyalkyl or aminoalkyl as a substituent. These may be prepared by reacting such compounds with anhydrides such as succinic anhydride.

The invention disclosed herein will also be understood to encompass in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein will also be understood to encompass the disclosed compounds isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

The compounds of the instant invention may be prepared using methods known to those skilled in the art, and in other embodiments by employing novel synthetic schemes as provided herein, which, along with the exemplified intermediate compounds, also fall within the scope of the invention.

Accordingly, the present invention also provided novel methods and compositions for producing the compounds of the present invention as well as other arylbicyclo[3.1.0]hexylamines.

In certain embodiments, the present invention provides methods of making an arylbicyclo[3.1.0]hexylamine of the following formula II,

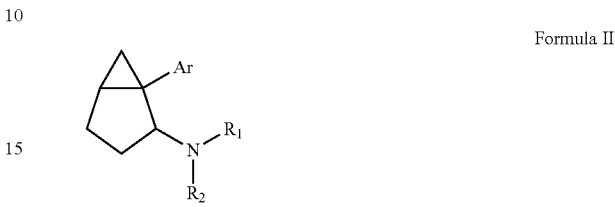

Formula II wherein Ar is a phenyl, a naphthyl or an aryl heterocycle group which is unsubstituted or substituted with one or more substituents selected from fluoro, chloro, bromo, iodo, —NO$_2$, —CN, —NH$_2$, C$_{1-8}$ alkyl, C$_{2-8}$ alkenyl, C$_{2-8}$ alkynyl, halo(C$_{1-8}$)alkyl, hydroxy, trifluoromethyl, C$_{3-8}$ cycloalkyl, C$_{1-3}$ alkoxyl, C$_{1-3}$ alkoxy(C$_{1-3}$)alkyl, carboxy(C$_{1-3}$)alkyl, C$_{1-3}$ alkanoyl, halo(C$_{1-3}$)alkoxyl, C$_{1-8}$ alkylamino, and di(C$_{1-8}$)alkylamino, and R$_1$ and R$_2$ are independently selected from hydrogen, unsubstituted C$_{1-10}$ alkyl, C$_{3-8}$ cycloalkyl, C$_{2-10}$ alkenyl, and C$_{3-10}$ alkynyl, and substituted C$_{1-10}$ alkyl, C$_{3-10}$ alkenyl and C$_{3-10}$ alkynyl wherein the substituent is one or more of hydroxy, cyano, halogen, C$_{1-6}$ alkoxy, aryl substituted C$_{1-6}$ alkoxy, aryloxy, aryloxy substituted with one or more halogens, C$_{1-6}$ alkyl, C$_{1-6}$ alkyl independently substituted with one or more of cyano and halogen, C$_{1-4}$ alkoxy, and C$_{1-4}$ haloalkoxy, comprising the steps of:

(a) coupling a compound of the following formula (i), Ar—I, wherein Ar is defined as above, with propargyl alcohol to produce a compound of the following formula (ii), Ar—≡—CH$_2$OH;

(b) oxidizing the compound of formula (ii) to produce a compound of the following formula (iii), Ar—≡—CHO;

(c) reacting the compound of formula (iii) with

⟋⟍MgBr to produce a compound of the following formula (iv),

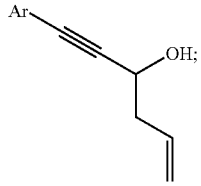

(d) causing acylation followed by cyclization and deprotection of the compound of formula (iv) to produce a compound of the following formula (v),

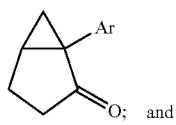

(e) causing reductive amination of the compound of formula (v) by reacting the compound of formula (v) with $NHR_1R_2$, wherein $R_1$ and $R_2$ are defined as above, to produce the arylbicyclo[3.1.0]hexylamine.

In other embodiments, the present invention provides methods of making an arylbicyclo[3.1.0]hexylamine of the following formula III,

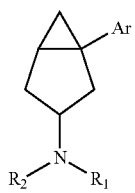

Formula III wherein Ar is a phenyl, a naphthyl or an aryl heterocycle group which is unsubstituted or substituted with one or more substituents selected from fluoro, chloro, bromo, iodo, $-NO_2$, $-CN$, $-NH_2$, $C_{1-8}$ alkyl, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxyl, $C_{1-3}$ alkoxy($C_{1-3}$)alkyl, carboxy($C_{1-3}$)alkyl, $C_{1-3}$ alkanoyl, halo($C_{1-3}$)alkoxyl, $C_{1-8}$ alkylamino, and di($C_{1-8}$)alkylamino, and $R_1$ and $R_2$ are independently selected from hydrogen, unsubstituted $C_{1-10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy, comprising the steps of:

(a) coupling a compound of the following formula (I), Ar—I, wherein Ar is defined as above, with propargyl alcohol to produce a compound of the following formula (ii),

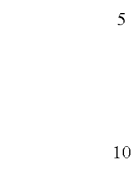

(b) oxidizing the compound of formula (ii) to produce a compound of the following formula (iii),

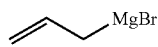

(c) reacting the compound of formula (iii) with

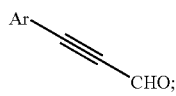

to produce a compound of the following formula (iv),

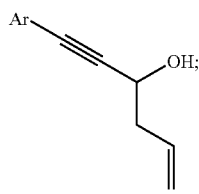

(d) causing cyclization of the compound of formula (iv) to produce a compound of the following formula (vi),

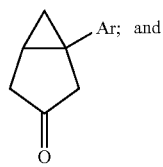

(e) causing reductive amination of the compound of formula (vi) by reacting the compound of formula (vi) with $NHR_1R_2$, wherein $R_1$ and $R_2$ are defined as above, to produce the arylbicyclo[3.1.0]hexylamine.

In additional embodiments, the present invention provides methods of making an arylbicyclo[3.1.0]hexylamine of the following formula IV,

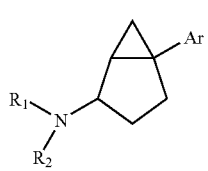

Formula IV wherein Ar is a phenyl, a naphthyl or an aryl heterocycle group which is unsubstituted or substituted with one or more substituents selected from fluoro, chloro, bromo, iodo, $-NO_2$, $-CN$, $-NH_2$, $C_{1-8}$ alkyl, $C_{2-8}$ alkenyl, $C_{2-8}$ alkynyl, halo($C_{1-8}$)alkyl, hydroxy, trifluoromethyl, $C_{3-8}$ cycloalkyl, $C_{1-3}$ alkoxyl, $C_{1-3}$ alkoxy$(C_{1-3})$alkyl, carboxy$(C_{1-3})$alkyl, $C_{1-3}$ alkanoyl, halo$(C_{1-3})$alkoxyl, $C_{1-8}$ alkylamino, and di$(C_{1-8})$alkylamino, and $R_1$ and $R_2$ are independently selected from hydrogen, unsubstituted $C_{10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy, comprising the steps of:

(a) coupling a compound of the following formula (I), Ar—X, wherein Ar is defined as above and X is Br or I, with 3-methoxy-2-cyclopenten-1-one to produce a compound of the following formula (vii),

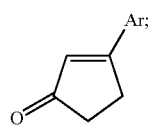

(b) reducing the compound of formula (vii) to produce a compound of the following formula (viii),

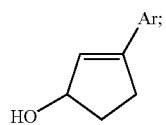

(c) causing cyclopropanation of the compound of formula (viii) to produce a compound of the following formula (ix),

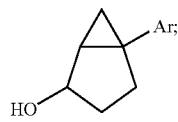

(d) oxidizing the compound of formula (ix) to produce a compound of the following formula (x),

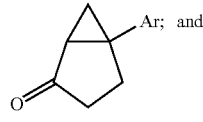

(e) causing reductive amination of the compound of formula (vi) by reacting the compound of formula (x) with $NHR_1R_2$, wherein $R_1$ and $R_2$ are defined as above, to produce the arylbicyclo[3.1.0]hexylamine.

In further embodiments, the present invention provides methods of making an arylbicyclo[3.1.0]hexylamine of the following formula III,

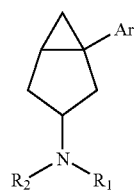

Formula III wherein Ar is a phenyl, a naphthyl or an aryl heterocycle group which is unsubstituted or substituted with one or more substituents selected from fluoro, chloro, bromo, iodo, —$NO_2$, —CN, —$NH_2$, $C_{1-8}$ alkyl, $C_{2-8}$ alkenyl, $C_{2-8}$ alkynyl, halo$(C_{1-8})$alkyl, hydroxy, trifluoromethyl, $C_{3-8}$ cycloalkyl, $C_{1-3}$ alkoxyl, $C_{1-3}$ alkoxy$(C_{1-3})$alkyl, carboxy$(C_{1-3})$alkyl, $C_{1-3}$ alkanoyl, halo$(C_{1-3})$alkoxyl, $C_{1-8}$ alkylamino, and di$(C_{1-8})$alkylamino, and $R_1$ and $R_2$ are independently selected from hydrogen, unsubstituted $C_{1-10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy, comprising the steps of:

(a) reacting a compound of the following formula (xi),

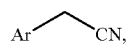

wherein Ar is defined as above, with epichlohydrin or an enantiomer thereof, to produce a compound of the following formula (xii),

or an enantiomer or diastereomer thereof, or a compound of the following formula (xiii),

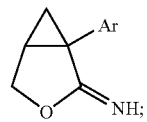

(b) hydrolyzing and causing cyclization of the compound of formula (xii), or an enantiomer or diastereomer thereof, or the compound of formula (xiii) to produce a compound of the following formula (xiv),

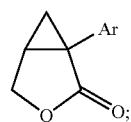

(c) reducing the compound of formula (xiv) to produce a compound of the following formula (xv),

(d) brominating the compound of formula (xv) to produce a compound of the following formula (xvi),

(e) reacting the compound of formula (xvi) with K₂Fe(CO)₄ to produce a compound of the following formula (vi),

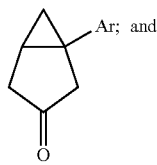

(f) causing reductive amination of the compound of formula (vi) by reacting the compound of formula (vi) with NHR₁R₂, wherein R₁ and R₂ are defined as above, to produce the arylbicyclo[3.1.0]hexylamine.

Although many of the novel arylbicyclo[3.1.0]hexylamines of the invention may be prepared according to methods known to those skilled in the art, they may also be generated, for example, according to the exemplary reaction schemes set forth below. While these novel schemes employ various intermediates and starting materials, it is to be understood that the illustrated processes are also applicable to compounds having alternative structure, substituent patterns, or stereochemistry depicted in these schemes.

Reaction Scheme 1 below generally sets forth an exemplary process for preparing 1-arylbicyclo[3.1.0]hexan-2-amines, from iodoaryl starting material.

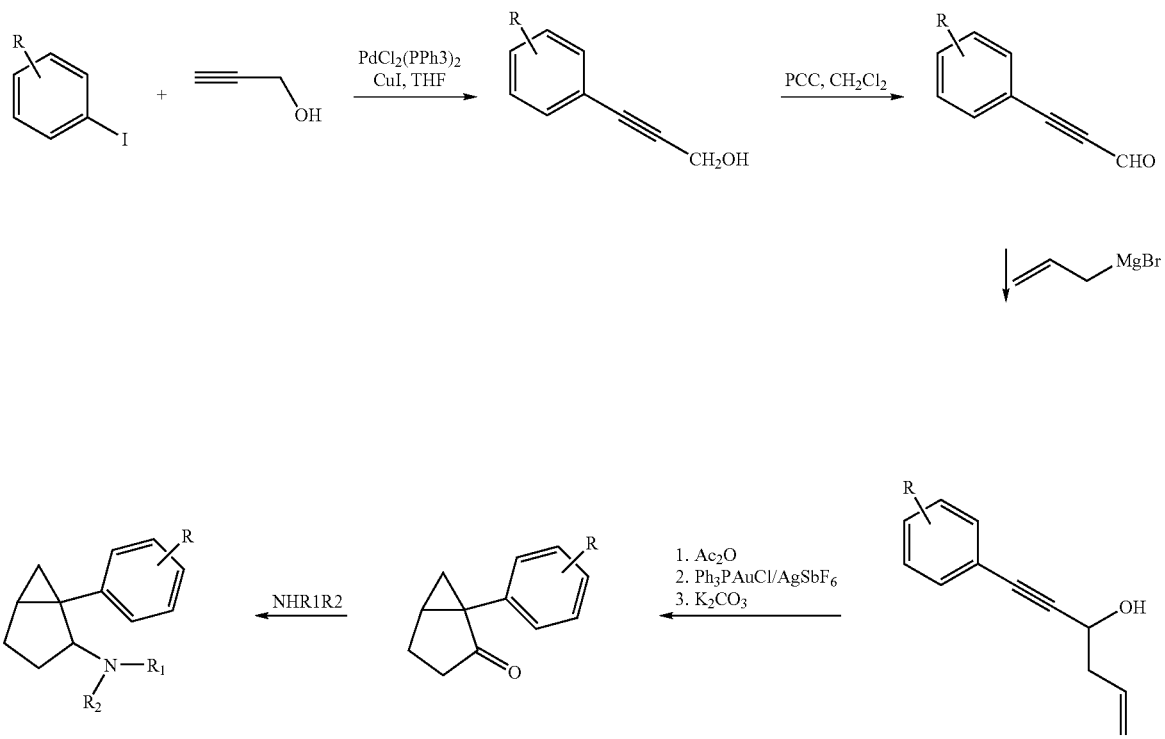

R = 4-Me, 3, 4-diCl, etc.
Ph-R could be naphthyl
R1 or R2 = H, Me, etc.

Reaction Scheme 2 below generally sets forth an exemplary process for preparing 1-arylbicyclo[3.1.0]hexan-3-amines from Iodoaryl starting material.

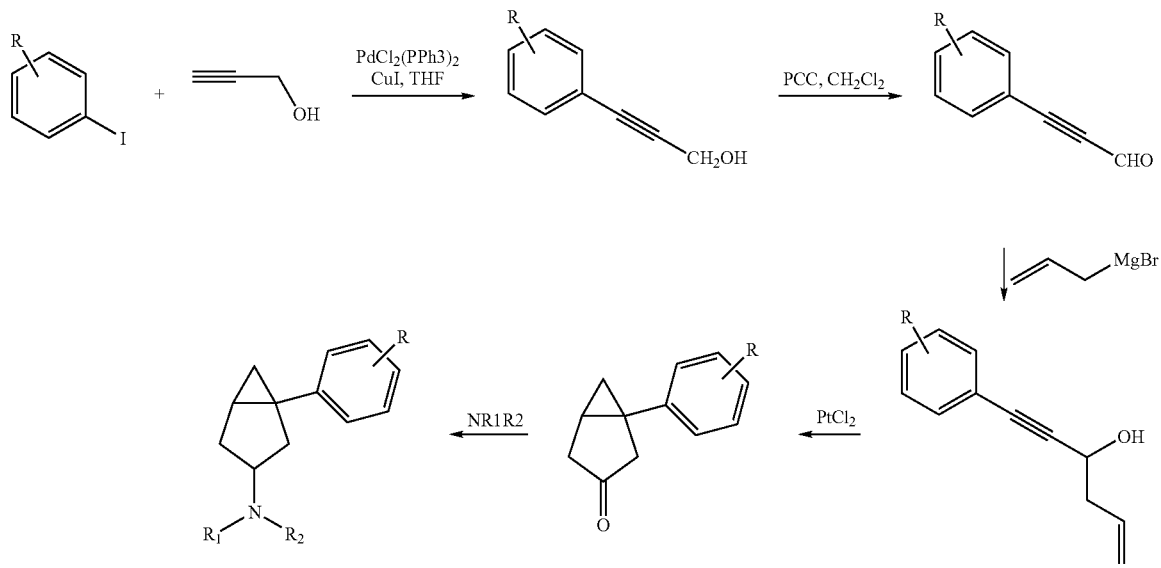

R = 4-Me, 3, 4-diCl, etc.
Ph-R could be naphthyl
R1 or R2 = H, Me, etc.

Reaction Scheme 3 below generally sets forth an exemplary process for preparing 5-arylbicyclo[3.1.0]hexan-2-amines from aryl halide starting material.

-continued

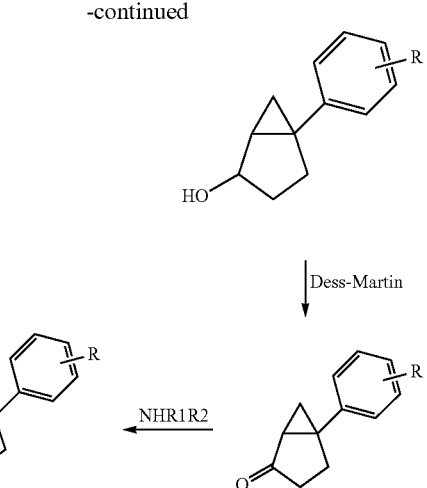

X = Br, I
R = 4-Me, 3, 4-diCl, etc.
Ph-R could be naphthyl
R1 or R2 = H, Me, etc.

Reaction Scheme 4 below illustrates another exemplary process for the preparation of 1-arylbicyclo[3.1.0]hexan-3-amines.

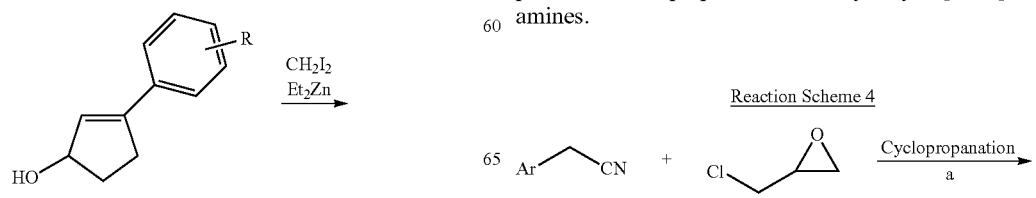

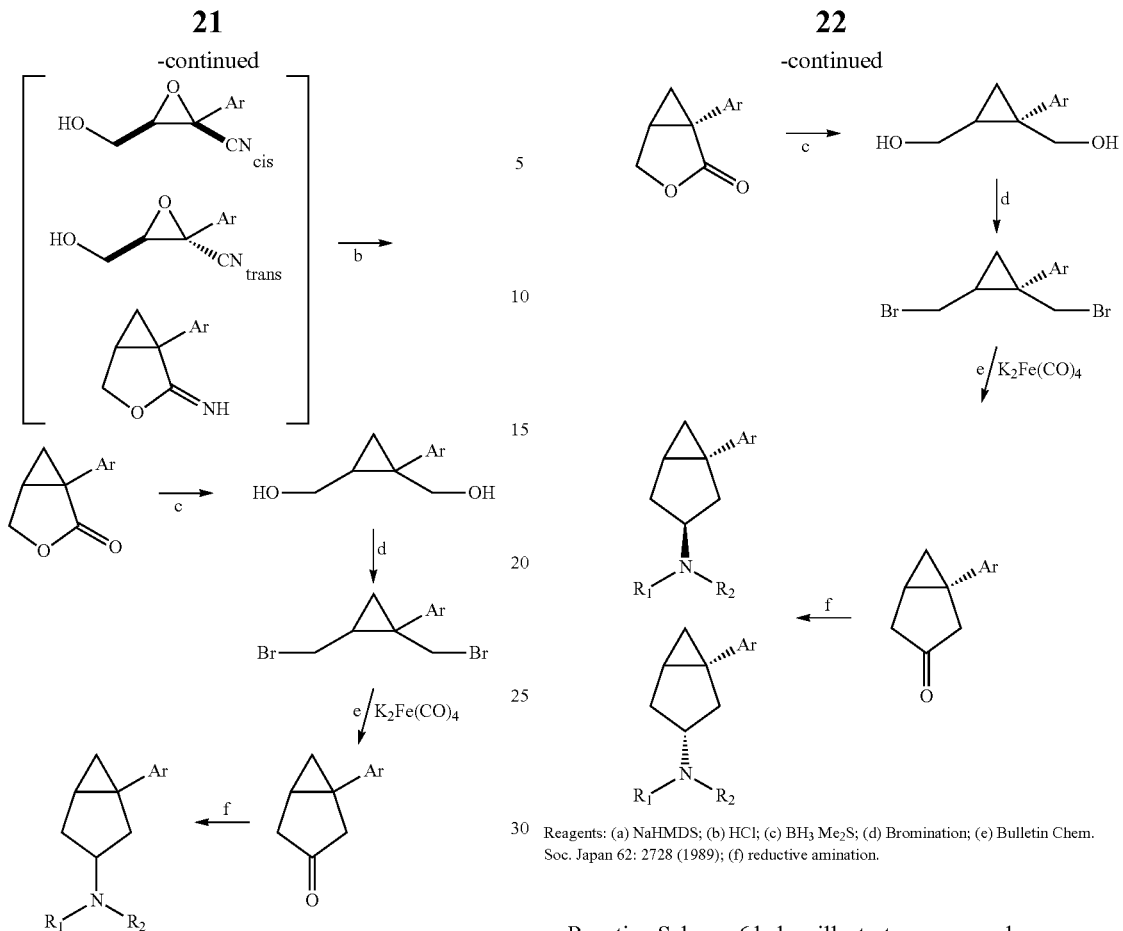

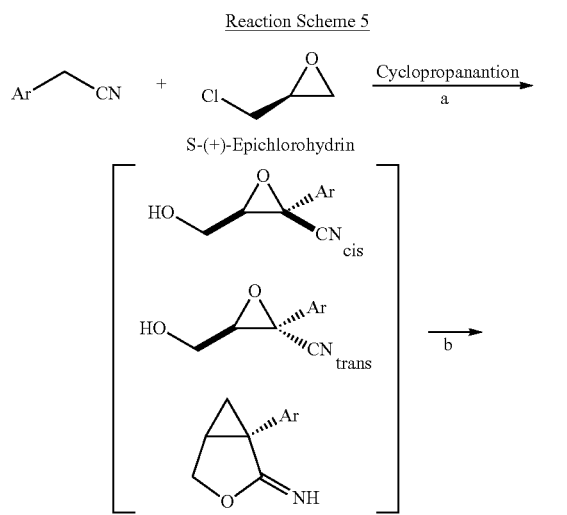

Reagents: (a) NaHMDS; (b) HCl; (c) BH$_3$ Me$_2$S; (d) Bromination; (e) Bulletin Chem. Soc. Japan 62: 2728 (1989); (f) reductive amination.

Reaction Scheme 5 below illustrates an exemplary process for the preparation of chiral 1-arylbicyclo[3.1.0]hexan-3-amines. Using (S)-(+)-epichlorohydrin as a starting material in the same process described in Scheme 5 will ensure a final product with 1-R chirality (Skolnick, P., Basile, A. and Chen, Z., International Patent Application, Pub. No. WO/2006/098101; Sep. 14, 2006).

Reagents: (a) NaHMDS; (b) HCl; (c) BH$_3$ Me$_2$S; (d) Bromination; (e) Bulletin Chem. Soc. Japan 62: 2728 (1989); (f) reductive amination.

Reaction Scheme 6 below illustrates an exemplary process for the preparation of chiral 1-arylbicyclo[3.1.0]hexan-3-amines. Using (R)-(−)-epichlorohydrin as a starting material in the same process described in Scheme 5 will ensure a final product with 1-S chirality (Skolnick, P., Basile, A. and Chen, Z., International Patent Application, Pub. No. WO/2006/098101; Sep. 14, 2006).

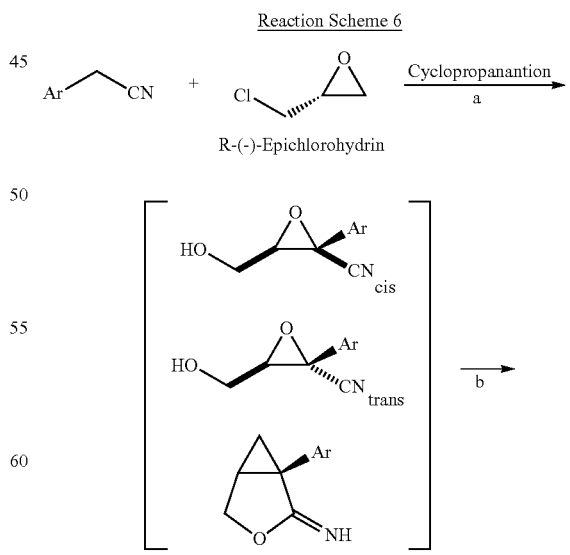

23
-continued

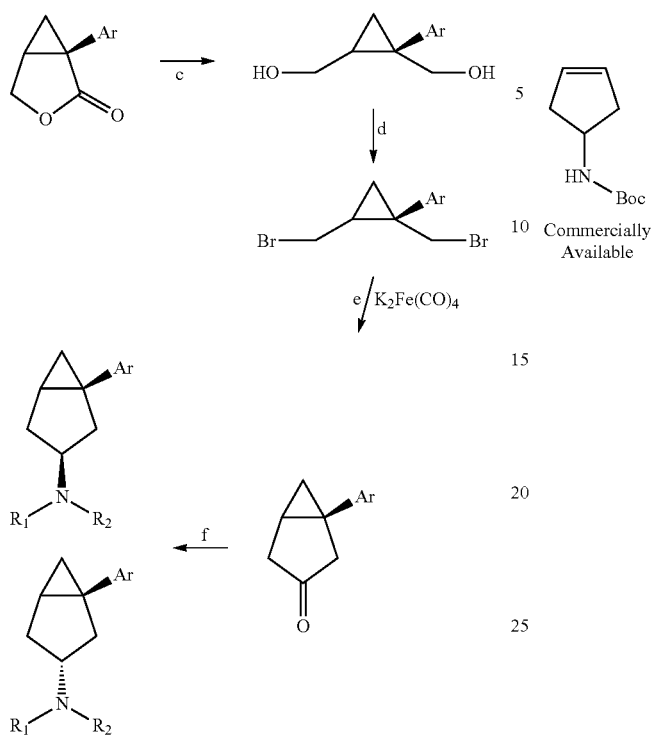

Reagents: (a) NaHMDS; (b) HCl; (c) BH$_3$ Me$_2$S; (d) Bromination; (e) Bulletin Chem. Soc. Japan 62: 2728 (1989); (f) reductive amination.

Reaction Scheme 7 below illustrates another exemplary process for 1-arylbicyclo[3.1.0]hexan-3-amines. The starting material, 3-bromocyclopent-3-enol, has been reported in literature [See, for example, Yong, W. et al., Synlett 9: 911-912 (1996)].

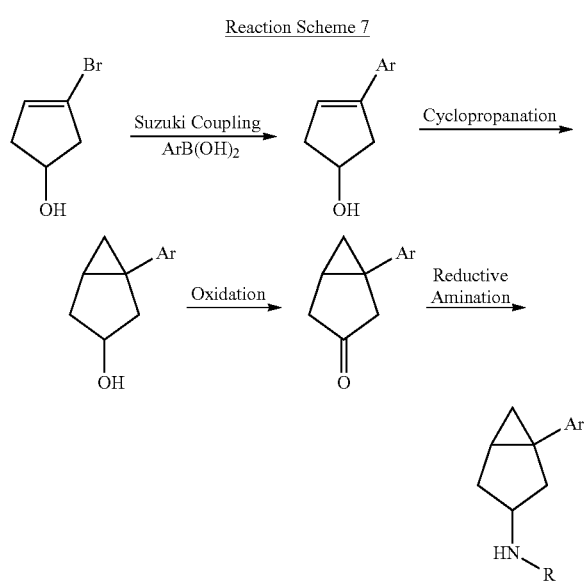

Reaction Scheme 8 below illustrates another exemplary process for 1-arylbicyclo[3.1.0]hexan-3-amines. The starting material is commercially available.

24

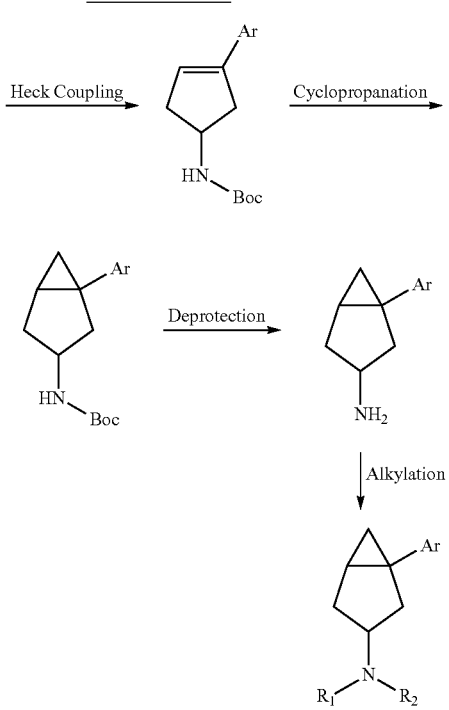

Reaction Scheme 9 below illustrates another exemplary process for 5-arylbicyclo[3.1.0]hexan-2-amines. The starting material, 3-bromocyclopent-2-enol, has been reported in the literature [See, for example, McBriar, M. D. et al., J. Med. Chem. 49: 2294-2310 (2006)].

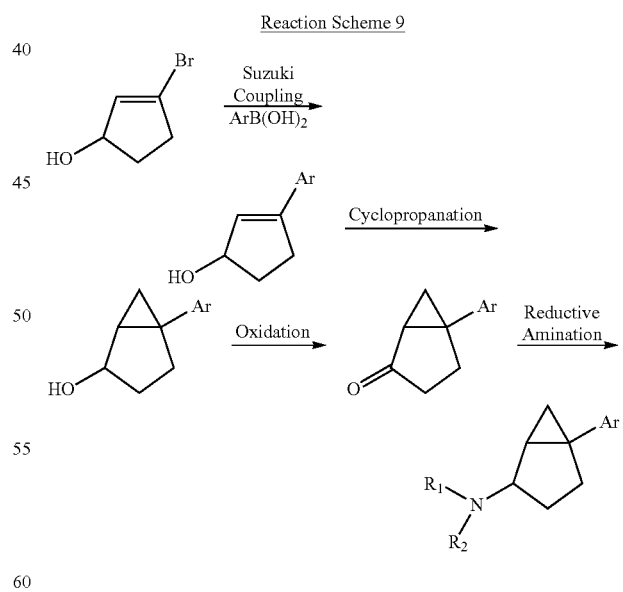

Enantiomers of the compounds of the present invention can be prepared by various methods, as exemplified above by Reaction Schemes 5 and 6.

Reaction Scheme 10 below illustrates another exemplary process for the preparation of 1-arylbicyclo[3.1.0]hexan-3-amines.

Reaction Scheme 10
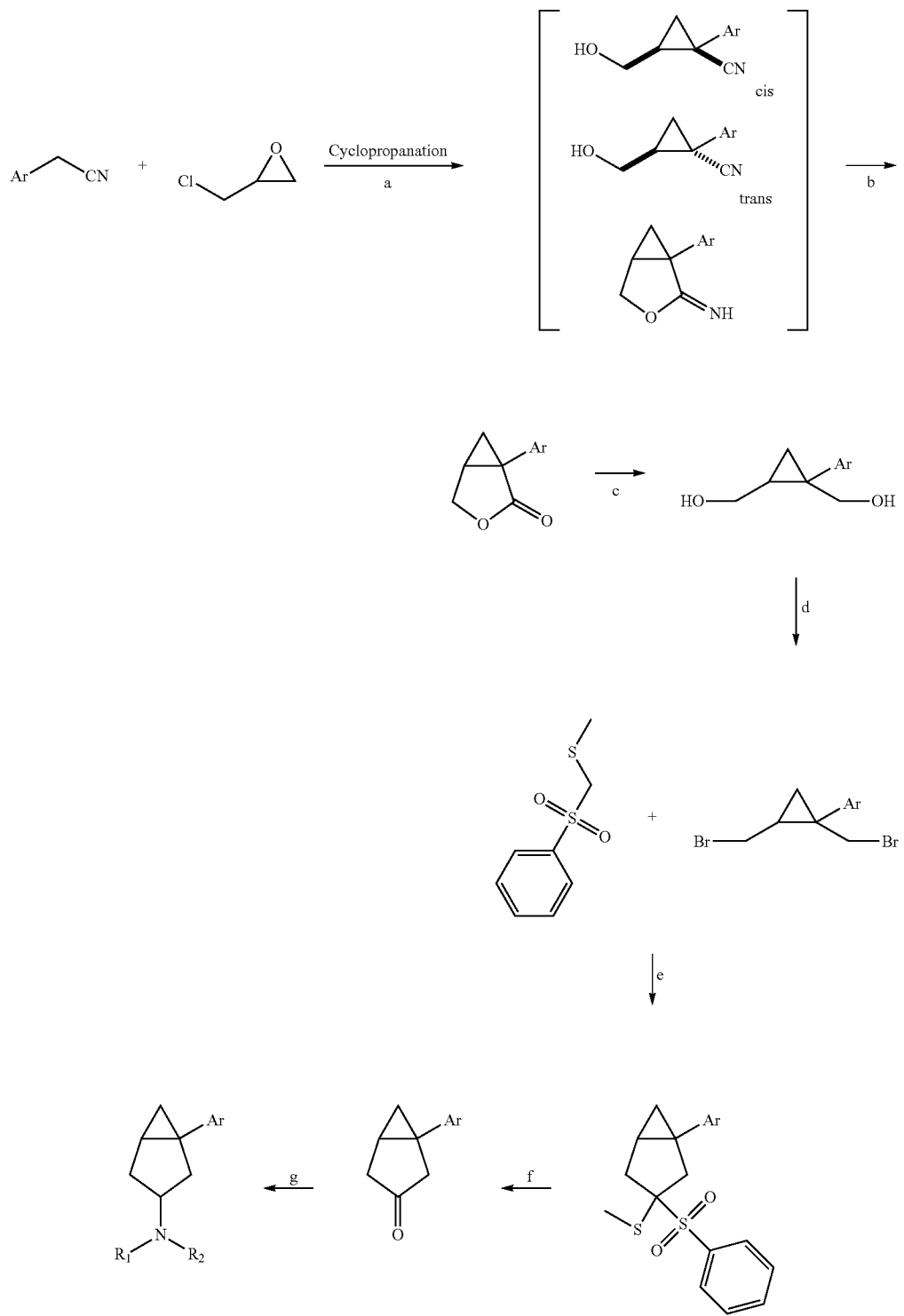
Reagents: (a) NaHMDS; (b) HCl; (c) BH₃ Me₂S; (d) CBr₄, PPh₃; (e) NaH; (f) HCl; (g) reductive amination Reaction Scheme 11 below illustrates an exemplary process for the preparation of chiral 1-arylbicyclo[3.1.0]hexan-3-amines. Using (S)-(+)-epichlorohydrin as a starting material in the same process described in Scheme 10 will ensure a final product with 1-R chirality (Cabadio et al., *Fr. Bollettino Chimico Farmaceutico* 117:331-42, 1978). Different diastereomers (3-R and 3-S) could be obtained by column separation.

Reaction Scheme 11

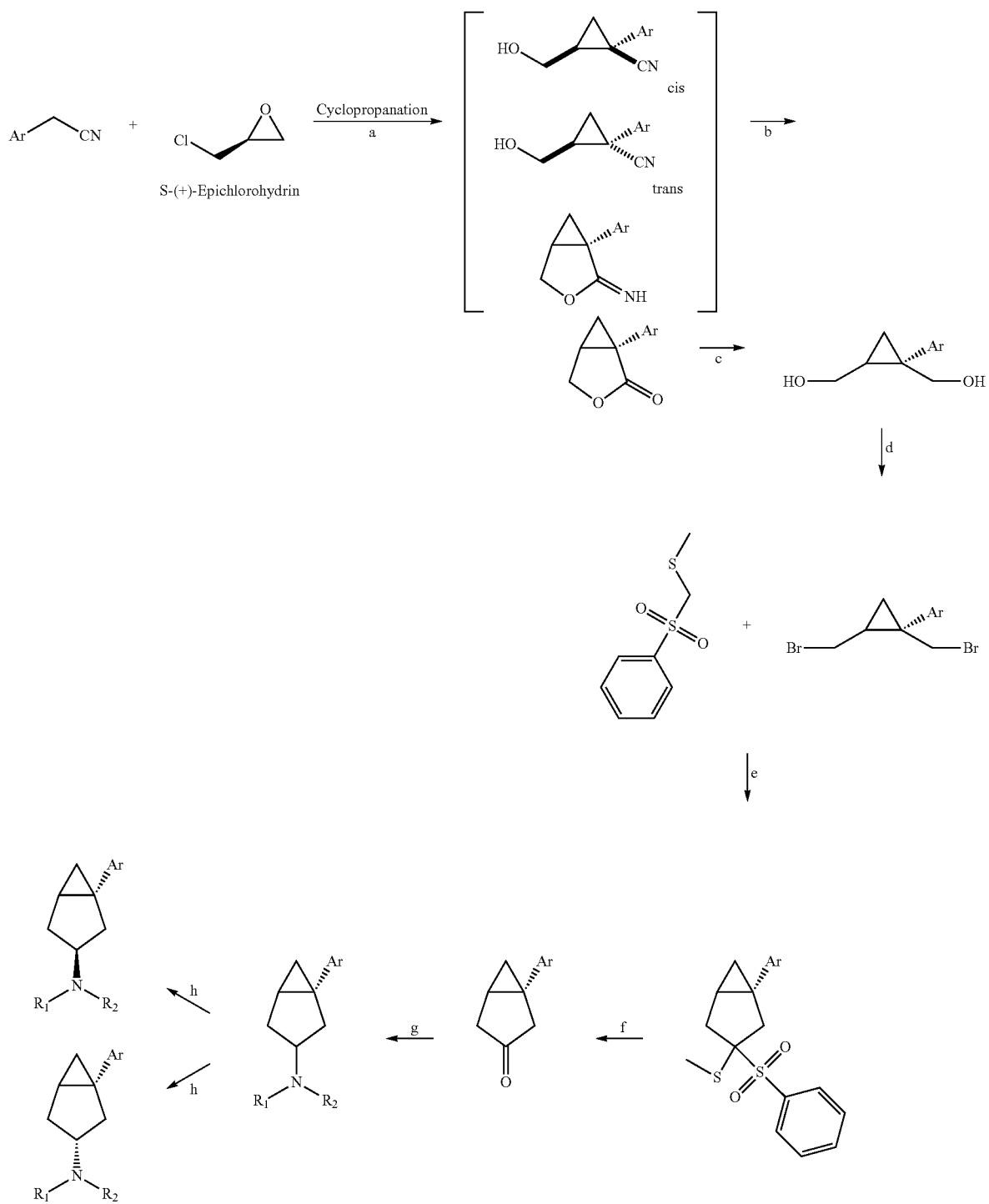

Reagents: (a) NaHMDS; (b) HCl; (c) BH$_3$ Me$_2$S; (d) CBr$_4$, PPh$_3$; (e) NaH; (f) HCl; (g) reductive amination; (h) resolution or chiral separation Reaction Scheme 12 below illustrates an exemplary process for the preparation of chiral 1-arylbicyclo[3.1.0]hexan-3-amines. Using (R)-(−)-epichlorohydrin as a starting material in the same process described in Scheme 10 will ensure a final product with 1-S chirality (Cabadio et al., *Fr. Bollettino Chimico Farmaceutico* 117:331-42, 1978). Different diastereomers (3-R and 3-S) could be obtained by column separation.

various novel starting materials, component steps, chemical intermediates, and end products, all of which are within the scope of the invention.

With regard to the foregoing synthetic schemes, and as otherwise used herein unless specified differently, Ar is a phenyl, a naphthyl or an aryl heterocycle group which is unsubstituted or substituted with one or more substituents selected from fluoro, chloro, bromo, iodo, —NO$_2$, —CN,

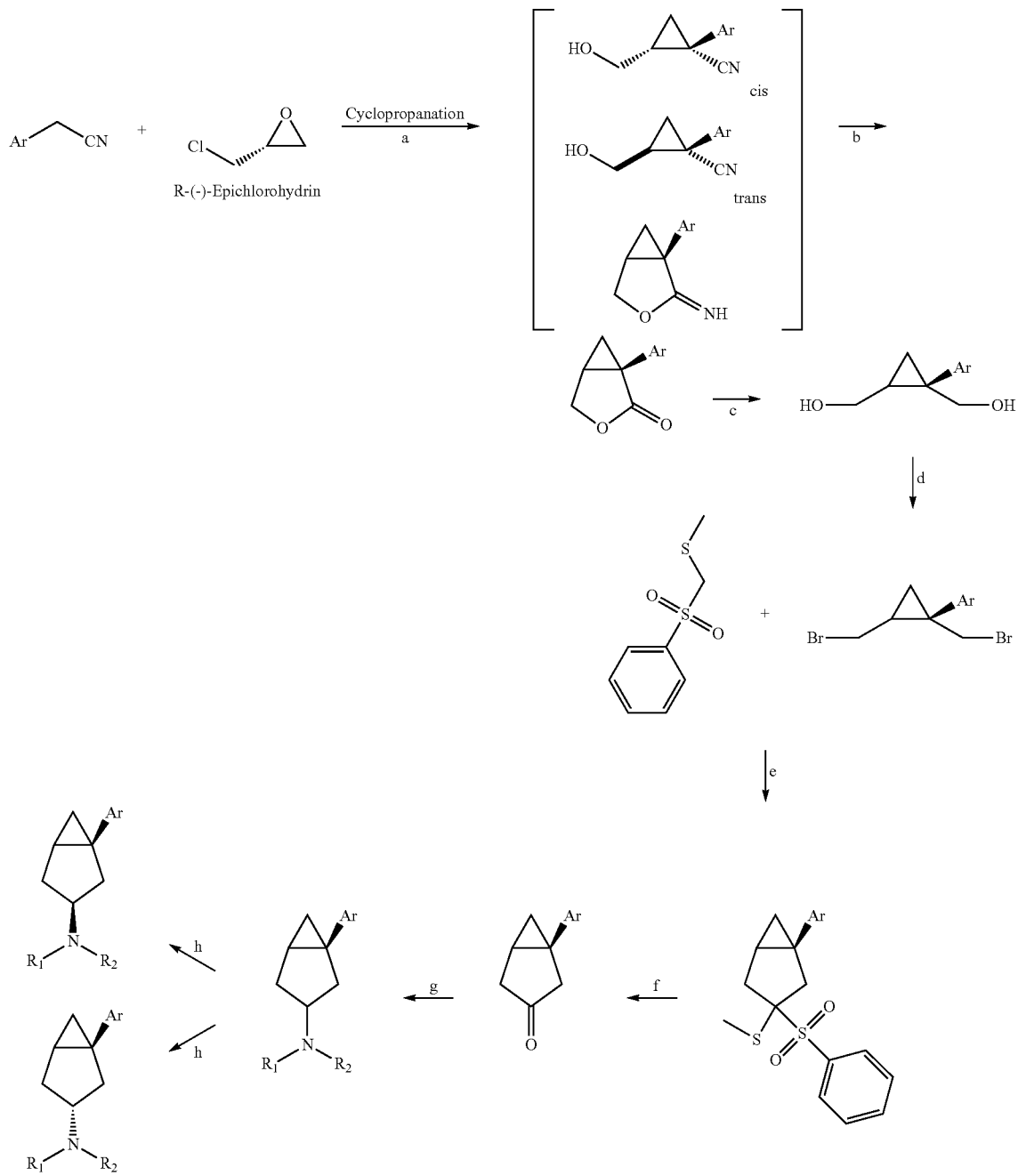

Reaction Scheme 12

Reagents: (a) NaHMDS; (b) HCl; (c) BH$_3$ Me$_2$S; (d) CBr$_4$, PPh$_3$; (e) NaH; (f) HCl; (g) reductive amination; (h) resolution or chiral separation The foregoing reaction schemes, and each of the exemplary processes described in Examples I-X below, set forth —NH$_2$, C$_{1-8}$ alkyl, C$_{2-8}$ alkenyl, C$_{2-8}$ alkynyl, halo(C$_{1-8}$) alkyl, hydroxy, trifluoromethyl, C$_{3-8}$ cycloalkyl, C$_{1-3}$ alkoxyl, $C_{1-3}$ alkoxy($C_{1-3}$)alkyl, carboxy($C_{1-3}$)alkyl, $C_{1-3}$ alkanoyl, halo($C_{1-3}$)alkoxyl, $C_{1-8}$ alkylamino, and di($C_{1-8}$)alkylamino; and $R_1$ and $R_2$ are independently selected from hydrogen, unsubstituted $C_{1-10}$ alkyl, $C_{3-8}$ cycloalkyl, $C_{2-10}$ alkenyl, and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy.

In practicing the methods of the present for methods for making arylbicyclo[3.1.0]hexylamines, various reagents may be utilized for the different reaction steps. In general, suitable reagents for the various reaction steps may be selected by one of ordinary skill in the art based on the present disclosure.

Suitable reducing agents and methodologies include, for example, lithium aluminum hydride (LAH), sodium aluminum hydride (SAH), $NaBH_4$ with $ZnCl_2$ and catalytic hydrogenation.

Suitable nitrogen protecting groups include, for example, benzyl, allyl, tert-butyl and 3,4-dimethoxy-benzyl groups. In general, nitrogen protecting groups are well known to those skilled in the art, see for example, "Nitrogen Protecting Groups in Organic Synthesis", John Wiley and Sons, New York, N.Y., 1981, Chapter 7; "Nitrogen Protecting Groups in Organic Chemistry", Plenum Press, New York, N.Y., 1973, Chapter 2; T. W. Green and P. G. M. Wuts in "Protective Groups in Organic Chemistry", 3rd edition, John Wiley & Sons, New York, N.Y., 1999.

When the nitrogen protecting group is no longer needed, it may be removed by methods well known in the art. For example, benzyl or 3,4-dimethoxy-benzyl groups may be removed by catalytic hydrogenation. In general, methods of removing nitrogen protecting groups are well known to those skilled in the art, see for example, "Nitrogen Protecting Groups in Organic Synthesis", John Wiley and Sons, New York, N.Y., 1981, Chapter 7; "Nitrogen Protecting Groups in Organic Chemistry", Plenum Press, New York, N.Y., 1973, Chapter 2; T. W. Green and P. G. M. Wuts in "Protective Groups in Organic Chemistry", 3rd edition, John Wiley & Sons, Inc. New York, N.Y., 1999.

Suitable reagents for causing cyclization include, for example, $SOCl_2$, $POCl_3$, oxalyl chloride, phosphorous tribromide, triphenylphosphorous dibromide and oxalyl bromide.

Exemplary synthetic methods, starting materials, and intermediates useful in various aspects of the invention for producing novel compounds of the present invention are described in the examples.

For the purposes of describing the invention, including the novel compounds and synthetic methods disclosed herein, the following terms and definitions are provided by way of example.

The term "halogen" as used herein refers to bromine, chlorine, fluorine or iodine. In one embodiment, the halogen is chlorine. In another embodiment, the halogen is bromine.

The term "hydroxy" as used herein refers to —OH or —O$^-$. The term "alkyl" as used herein refers to straight- or branched-chain aliphatic groups containing 1-20 carbon atoms, preferably 1-7 carbon atoms and most preferably 1-4 carbon atoms. This definition applies as well to the alkyl portion of alkoxy, alkanoyl and aralkyl groups. In one embodiment, the alkyl is a methyl group. The term "alkoxy" includes substituted and unsubstituted alkyl, alkenyl, and alkynyl groups covalently linked to an oxygen atom. In one embodiment, the alkoxy group contains 1 to 4 carbon atoms.

Embodiments of alkoxy groups include, but are not limited to, methoxy, ethoxy, isopropyloxy, propoxy, butoxy, and pentoxy groups. Embodiments of substituted alkoxy groups include halogenated alkoxy groups. In a further embodiment, the alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Exemplary halogen substituted alkoxy groups include, but are not limited to, fluoromethoxy, difluoromethoxy, trifluoromethoxy, chloromethoxy, dichloromethoxy, and trichloromethoxy.

The term "nitro", as used herein alone or in combination refers to a —$NO_2$ group.

The term "amino" as used herein refers to the group —NRR', where R and R' may independently be hydrogen, alkyl, aryl, alkoxy, or heteroaryl. The term "aminoalkyl" as used herein represents a more detailed selection as compared to "amino" and refers to the group —NRR', where R and R' may independently be hydrogen or ($C_1$-$C_4$)alkyl.

The term "trifluoromethyl" as used herein refers to —$CF_3$.

The term "trifluoromethoxy" as used herein refers to —$OCF_3$.

The term "cycloalkyl" as used herein refers to a saturated cyclic hydrocarbon ring system containing from 3 to 7 carbon atoms that may be optionally substituted. Exemplary embodiments include, but are not limited to, cyclopropyl, cyclobutyl, cyclopentyl and cyclohexyl. In certain embodiments, the cycloalkyl group is cyclopropyl. In another embodiment, the (cycloalkyl)alkyl groups contain from 3 to 7 carbon atoms in the cyclic portion and 1 to 4 carbon atoms in the alkyl portion. In certain embodiments, the (cycloalkyl)alkyl group is cyclopropylmethyl. The alkyl groups are optionally substituted with from one to three substituents selected from the group consisting of halogen, hydroxy and amino.

The terms "alkanoyl" and "alkanoyloxy" as used herein refer, respectively, to —C(O)-alkyl groups and —O—C(O)-alkyl groups, each optionally containing 2-5 carbon atoms. Specific embodiments of alkanoyl and alkanoyloxy groups are acetyl and acetoxy, respectively.

The term "aryl" as used herein refers to monocyclic or bicyclic aromatic hydrocarbon groups having from 6 to 12 carbon atoms in the ring portion, for example, phenyl, naphthyl, biphenyl and diphenyl groups, each of which may be substituted with, for example, one to four substituents such as alkyl, substituted alkyl as defined above, halogen, trifluoromethyl, trifluoromethoxy, hydroxy, alkoxy, cycloalkyloxy, alkanoyl, alkanoyloxy, amino, alkylamino, dialkylamino, nitro, cyano, carboxy, carboxyalkyl, carbamyl, carbamoyl and aryloxy. Specific embodiments of aryl groups in accordance with the present invention include phenyl, substituted phenyl, naphthyl, biphenyl, and diphenyl.

The term "aroyl," as used alone or in combination herein, refers to an aryl radical derived from an aromatic carboxylic acid, such as optionally substituted benzoic or naphthoic acids.

The term "aralkyl" as used herein refers to an aryl group bonded to the 4-pyridinyl ring through an alkyl group, preferably one containing 1-4 carbon atoms. A preferred aralkyl group is benzyl.

The term "nitrile" or "cyano" as used herein refers to the group —CN.

The term "dialkylamino" refers to an amino group having two attached alkyl groups that can be the same or different.

The term "alkenyl" refers to a straight or branched alkenyl group of 2 to 10 carbon atoms having 1 to 3 double bonds. Preferred embodiments include ethenyl, 1-propenyl, 2-propenyl, 1-methylethenyl, 1-butenyl, 2-butenyl, 3-butenyl, 2-methyl-2-propenyl, 1-pentenyl, 2-pentenyl, 4-pentenyl, 3-methyl-2-butenyl, 1-hexenyl, 2-hexenyl, 1-heptenyl, 2-heptenyl, 1-octenyl, 2-octenyl, 1,3-octadienyl, 2-nonenyl, 1,3-nonadienyl, 2-decenyl, etc.

The term "alkynyl" as used herein refers to a straight or branched alkynyl group of 2 to 10 carbon atoms having 1 to 3 triple bonds. Exemplary alkynyls include, but are not limited to, ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl, and 2-decynyl.

The term "hydroxyalkyl" alone or in combination, refers to an alkyl group as previously defined, wherein one or several hydrogen atoms, preferably one hydrogen atom has been replaced by a hydroxyl group. Examples include hydroxymethyl, hydroxyethyl and 2-hydroxyethyl.

The term "aminoalkyl" as used herein refers to the group —NRR', where R and R' may independently be hydrogen or $(C_1-C_4)$alkyl.

The term "alkylaminoalkyl" refers to an alkylamino group linked via an alkyl group (i.e., a group having the general structure -alkyl-NH-alkyl or -alkyl-N(alkyl)(alkyl)). Such groups include, but are not limited to, mono- and di-$(C_1-C_8$ alkyl)amino$C_1-C_8$ alkyl, in which each alkyl may be the same or different.

The term "dialkylaminoalkyl" refers to alkylamino groups attached to an alkyl group. Examples include, but are not limited to, N,N-dimethylaminomethyl, N,N-dimethylaminoethyl N,N-dimethylaminopropyl, and the like. The term dialkylaminoalkyl also includes groups where the bridging alkyl moiety is optionally substituted.

The term "haloalkyl" refers to an alkyl group substituted with one or more halo groups, for example chloromethyl, 2-bromoethyl, 3-iodopropyl, trifluoromethyl, perfluoropropyl, 8-chlorononyl and the like.

The term "carboxyalkyl" as used herein refers to the substituent —R'—COOH wherein R' is alkylene; and carbalkoxyalkyl refers to —R'—COOR wherein R' and R are alkylene and alkyl respectively. In certain embodiments, alkyl refers to a saturated straight- or branched-chain hydrocarbyl radical of 1-6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent.

The term "alkoxyalkyl" refers to a alkylene group substituted with an alkoxy group. For example, methoxyethyl $[CH_3OCH_2CH_2—]$ and ethoxymethyl $(CH_3CH_2OCH_2—]$ are both $C_3$ alkoxyalkyl groups.

The term "carboxy", as used herein, represents a group of the formula —COOH.

The term "alkanoylamino" refers to alkyl, alkenyl or alkynyl groups containing the group —C(O)— followed by —N(H)—, for example acetylamino, propanoylamino and butanoylamino and the like.

The term "carbonylamino" refers to the group —NR—CO—CH$_2$—R', where R and R' may be independently selected from hydrogen or $(C_1-C_4)$alkyl.

The term "carbamoyl" as used herein refers to —O—C(O)NH$_2$.

The term "carbamyl" as used herein refers to a functional group in which a nitrogen atom is directly bonded to a carbonyl, i.e., as in —NRC(=O)R' or —C(=O)NRR', wherein R and R' can be hydrogen, alkyl, substituted alkyl, alkenyl, substituted alkenyl, alkoxy, cycloalkyl, aryl, heterocyclo, or heteroaryl.

The term "heterocyclo" refers to an optionally substituted, unsaturated, partially saturated, or fully saturated, aromatic or nonaromatic cyclic group that is a 4 to 7 membered monocyclic, or 7 to 11 membered bicyclic ring system that has at least one heteroatom in at least one carbon atom-containing ring. The substituents on the heterocyclo rings may be selected from those given above for the aryl groups. Each ring of the heterocyclo group containing a heteroatom may have 1, 2 or 3 heteroatoms selected from nitrogen atoms, oxygen atoms and sulfur atoms. Plural heteroatoms in a given heterocyclo ring may be the same or different. The heterocyclo group may be attached to the 4-pyridinyl ring at any heteroatom or carbon atom. In one embodiment, two R groups form a fused ring with the carbons at position 2 and 3 of the pyridinyl ring, there is formed a 7-quinolin-4-yl moiety.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomelic" refers to a molecule that is nonsuperimposeable on its mirror image and hence optically active wherein the enantiomer rotates the plane of polarized light in one direction and its minor image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

In additional embodiments, the invention provides pharmaceutical compositions and methods for treating CNS disorders, including but not limited to neuropsychiatric conditions, such as depression and anxiety. Suitable forms of the compounds of the invention for use in biologically active compositions and methods of the invention include the compounds exemplified herein, as well as their pharmaceutically acceptable salts, polymorphs, solvates, hydrates, and prodrugs.

Within related embodiments, the invention provides methods for treating CNS disorders responsive to the inhibition of biogenic amine transporters, in particular one or more, or any combination of, the norepinephrine, serotonin and dopamine transporters, in mammalian subjects. In more detailed embodiments, the invention provides methods for using the novel compounds disclosed herein for treating CNS disorders, including a range of neuropsychiatric disorders, such as depression and anxiety. In various embodiments, the compositions and methods are formulated, and administered, effectively as anti-depressants, or as anxiolytic agents.

In accordance with the invention, compounds disclosed herein, optionally formulated with additional ingredients in a pharmaceutically acceptable composition, are administered to mammalian subjects, for example a human patient, to treat or prevent one or more symptom(s) of a CNS disorder alleviated by inhibiting dopamine reuptake, and/or norepinephrine reuptake, and/or serotonin reuptake. In certain embodiments, "treatment" or "treating" refers to amelioration of one or more symptom(s) of a CNS disorder, whereby the symptom(s) is/are alleviated by inhibiting dopamine and/or norepinephrine and/or serotonin reuptake. In other embodiments, "treatment" or "treating" refers to an amelioration of at least one measurable physical parameter associated with a CNS disorder. In yet another embodiment, "treatment" or "treating" refers to inhibiting or reducing the progression or severity of a CNS disorder (or one or more symptom(s) thereof) alleviated by inhibiting dopamine and/or norepinephrine and/or serotonin reuptake, e.g., as discerned based on physical, physiological, and/or psychological parameters. In additional embodiments, "treatment" or "treating" refers to delaying the onset of a CNS disorder (or one or more symptom(s) thereof) alleviated by inhibiting dopamine and/or norepinephrine and/or serotonin reuptake.

In certain embodiments, a compound of the present invention or a pharmaceutically acceptable salt thereof is administered to a mammalian subject, for example a human patient, as a preventative or prophylactic treatment against a CNS disorder (or one or more symptom(s) thereof) alleviated by inhibiting dopamine and/or norepinephrine and/or serotonin reuptake. As used herein, "prevention", "preventing", and prophylaxis refers to a reduction in the risk or likelihood that the subject will acquire a CNS disorder or one or more symptom(s) thereof, which risk or likelihood is reduced in the subject by inhibiting dopamine and/or norepinephrine and/or serotonin reuptake. Alternatively, prevention and prophylaxis may correlate with a reduced risk of recurrence of the CNS disorder or symptom(s) thereof in the subject once the subject has been cured, restored to a normal state, or placed in remission from the subject CNS disorder. In related embodiments, a compound or pharmaceutical composition of the invention is administered as a preventative measure to the subject. Exemplary subjects amenable to prophylactic treatment in this context may have a genetic predisposition to a CNS disorder amenable to treatment by inhibiting dopamine, and/or serotonin, and/or norepinephrine reuptake, such as a family history of a biochemical imbalance in the brain, or a non-genetic predisposition to a disorder alleviated by inhibiting dopamine and/or norepinephrine and/or serotonin reuptake.

A compound of the present invention and pharmaceutically acceptable salts thereof are useful for treating or preventing endogenous disorders alleviated by inhibiting dopamine and/or norepinephrine and/or serotonin reuptake. Such disorders include, but are not limited to, attention-deficit disorder, depression, anxiety, obesity, Parkinson's disease, tic disorders, and addictive disorders.

Disorders alleviated by inhibiting dopamine and/or norepinephrine and/or serotonin reuptake are not limited to the specific disorders described herein, and the compositions and methods of the invention will be understood or readily ascertained to provide effective treatment agents for treating and/or preventing a wide range of additional CNS disorders and associated symptoms. For example, the compounds of the invention will provide promising candidates for treatment and/or prevention of attention deficit hyperactivity disorder and related symtoms, as well as forms and symptoms of alcohol abuse, drug abuse, obsessive compulsive behaviors, learning disorders, reading problems, gambling addiction, manic symptoms, phobias, panic attacks, oppositional defiant behavior, conduct disorder, academic problems in school, smoking, abnormal sexual behaviors, schizoid behaviors, somatization, depression, sleep disorders, general anxiety, stuttering, and tic disorders (See, for example, U.S. Pat. No. 6,132,724). These and other symptoms, regardless of the underlying CNS disorder, are each prospective therapeutic targets for the novel compositions and methods of the invention that mediate therapeutic benefits by inhibiting dopamine and/or norepinephrine and/or serotonin reuptake. Additional CNS disorders contemplated for treatment employing the compositions and methods of the invention are described, for example, in the Quick Reference to the Diagnostic Criteria From DSM-IV (Diagnostic and Statistical Manual of Mental Disorders, Fourth Edition), The American Psychiatric Association, Washington, D.C., 1994, 358 pages. These target disorders for treatment and/or prevention according to the invention, include, but are not limited to, Attention-Deficit/Hyperactivity Disorder, Predominately Inattentive Type; Attention-Deficit/Hyperactivity Disorder, Predominately Hyperactivity-Impulsive Type; Attention-Deficit/Hyperactivity Disorder, Combined Type; Attention-Deficit/Hyperactivity Disorder not otherwise specified (NOS); Conduct Disorder; Oppositional Defiant Disorder; and Disruptive Behavior Disorder not otherwise specified (NOS).

Depressive disorders amenable for treatment and/or prevention according to the invention include, but are not limited to, Major Depressive Disorder, Recurrent; Dysthymic Disorder; Depressive Disorder not otherwise specified (NOS); and Major Depressive Disorder, Single Episode.

Addictive disorders amenable for treatment and/or prevention employing the methods and compositions of the invention include, but are not limited to, eating disorders, impulse control disorders, alcohol-related disorders, nicotine-related disorders, amphetamine-related disorders, cannabis-related disorders, cocaine-related disorders, hallucinogen use disorders, inhalant-related disorders, and opioid-related disorders, all of which are further sub-classified as listed below.

Eating disorders include, but are not limited to, Bulimia Nervosa, Nonpurging Type; Bulimia Nervosa, Purging Type; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder, with delusions; Alcohol Abuse; Alcohol Intoxication; Alcohol Withdrawal; Alcohol Intoxication Delirium; Alcohol Withdrawal Delirium; Alcohol-Induced Persisting Dementia; Alcohol-Induced Persisting Amnestic Disorder; Alcohol Dependence; Alcohol-Induced Psychotic Disorder, with hallucinations; Alcohol-Induced Mood Disorder; Alcohol-Induced Anxiety Disorder; Alcohol-Induced Sexual Dysfunction; Alcohol-Induced Sleep Disorders; Alcohol-Related Disorders not otherwise specified (NOS); Alcohol Intoxication; and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

Cannabis-related disorders include, but are not limited to, Cannabis Dependence; Cannabis Abuse; Cannabis Intoxication; Cannabis Intoxication Delirium; Cannabis-Induced Psychotic Disorder, with delusions; Cannabis-Induced Psychotic Disorder with hallucinations; Cannabis-Induced Anxiety Disorder; Cannabis Related Disorder not otherwise specified (NOS); and Cannabis Intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-use disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence; Inhalant Abuse; Inhalant Intoxication; Inhalant Intoxication Delirium; Inhalant-Induced Psychotic Disorder, with delusions; Inhalant-Induced Psychotic Disorder with hallucinations; Inhalant-Induced Anxiety Disorder; Inhalant Related Disorder not otherwise specified (NOS); and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder, with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

Tic disorders include, but are not limited to, Tourette's Disorder, Chronic Motor or Vocal Tic Disorder, Transient Tic Disorder, Tic Disorder not otherwise specified (NOS), Stuttering, Autistic Disorder, and Somatization Disorder.

By virtue of their multiple reuptake inhibitory activity, the novel compounds of the present invention are thus useful in a wide range of veterinary and human medical applications, in particular for treating and/or preventing a wide array of CNS disorders and/or associated symptom(s) alleviated by inhibiting dopamine and/or norepinephrine and/or serotonin reuptake.

Within additional aspects of the invention, combinatorial formulations and coordinate administration methods are provided which employ an effective amount of a compound of the invention (or a pharmaceutically effective enantiomer, salt, solvate, hydrate, polymorph, or prodrug thereof), and one or more additional active agent(s) that is/are combinatorially formulated or coordinately administered with the compound of the invention—yielding a combinatorial formulation or coordinate administration method that is effective to modulate, alleviate, treat or prevent a targeted CNS disorder, or one or more symptom(s) thereof, in a mammalian subject. Exemplary combinatorial formulations and coordinate treatment methods in this context a therapeutic compound of the invention in combination with one or more additional or adjunctive treatment agents or methods for treating the targeted CNS disorder or symptom(s), for example one or more antidepressant or anxiolytic agent(s) and/or therapeutic method(s).

In related embodiments of the invention, the compounds disclosed herein can be used in combination therapy with at least one other therapeutic agent or method. In this context, compounds of the invention can be administered concurrently or sequentially with administration of a second therapeutic agent, for example a second agent that acts to treat or prevent the same, or different, CNS disorder or symptom(s) for which the compound of the invention is administered. The compound of the invention and the second therapeutic agent can be combined in a single composition or adminstered in different compositions. The second therapeutic agent may also be effective for treating and/or preventing a CNS disorder or associated symptom(s) by inhibiting dopamine and/or norepinephrine and/or serotonin reuptake. The coordinate administration may be done simultaneously or sequentially in either order, and there may be a time period while only one or both (or all) active therapeutic agents, individually and/or collectively, exert their biological activities and therapeutic effects. A distinguishing aspect of all such coordinate treatment methods is that the compound of the invention exerts at least some detectable therapeutic activity toward alleviating or preventing the targeted CNS disorder or symptom(s), as described herein, and/or elicit a favorable clinical response, which may or may not be in conjunction with a secondary clinical response provided by the secondary therapeutic agent. Often, the coordinate administration of a compound of the invention with a secondary therapeutic agent as contemplated herein will yield an enhanced therapeutic response beyond the therapeutic response elicited by either or both the compound of the invention and/or secondary therapeutic agent alone.

As many of the CNS disorders and symptoms treatable or preventable using compounds of the present invention are chronic, in one embodiment combination therapy involves alternating between administering a compound of the present invention and a second therapeutic agent (i.e., alternating therapy regimens between the two drugs, e.g., at one week, one month, three month, six month, or one year intervals). Alternating drug regimens in this context will often reduce or even eliminate adverse side effects, such as toxicity, that may attend long-term administration of one or both drugs alone.

In certain embodiments of combinatorial formulations and coordinate treatment methods of the invention, the secondary therapeutic is a norepinephrine reuptake inhibitor. Examples of norepinephrine reuptake inhibitors useful in this context include tertiary amine tricyclics such as amitriptyline, clomipramine, doxepin, imipramine, (+)-trimipramine, and secondary amine tricyclics including amoxapine, atomoxetine, desipramine, maprotiline, nortriptyline, and protriptyline.

In certain embodiments of combinatorial formulations and coordinate treatment methods of the invention, the secondary therapeutic is a serotonin reuptake inhibitor. Examples of other serotonin reuptake inhibitors useful in this context include citalopram, fluoxetine, fluvoxamine, (−)-paroxetine, sertraline, and venlafaxine.

In other embodiments of combinatorial formulations and coordinate treatment methods provided herein, the secondary therapeutic agent is an anti-attention-deficit-disorder treatment agent. Examples of useful anti-attention-deficit-disorder agents for use in these embodiments include, but are not limited to, methylphenidate; dextroamphetamine; tricyclic antidepressants, such as imipramine, desipramine, and nortriptyline; and psychostimulants, such as pemoline and deanol.

In additional embodiments of combinatorial formulations and coordinate treatment methods provided herein, the secondary therapeutic agent is an anti-addictive-disorder agent. Examples of useful anti-addictive-disorder agents include, but are not limited to, tricyclic antidepressants; glutamate antagonists, such as ketamine HCl, dextromethorphan, dextrorphan tartrate and dizocilpine (MK801); degrading enzymes, such as anesthetics and aspartate antagonists; GABA agonists, such as baclofen and muscimol HBr; reuptake blockers; degrading enzyme blockers; glutamate agonists, such as D-cycloserine, carboxyphenylglycine, L-glutamic acid, and cis-piperidine-2,3-dicarboxylic acid; aspartate agonists; GABA antagonists such as gabazine (SR-95531), saclofen, bicuculline, picrotoxin, and (+) apomorphine HCl; and dopamine antagonists, such as spiperone HCl, haloperidol, and (−) sulpiride.

In other embodiments of combinatorial formulations and coordinate treatment methods provided herein, the secondary therapeutic agent is an anti-alcohol agent. Examples of useful anti-alcohol agents include, but are not limited to, disulfuram and naltrexone.

In other embodiments of combinatorial formulations and coordinate treatment methods provided herein, the secondary therapeutic agent is an anti-nicotine agent. Examples of useful anti-nicotine agents include, but are not limited to, clonidine.

In other embodiments of combinatorial formulations and coordinate treatment methods provided herein, the secondary therapeutic agent is an anti-opiate agent. Examples of useful anti-opiate agents include, but are not limited to, methadone, clonidine, lofexidine, levomethadyl acetate HCl, naltrexone, and buprenorphine.

In other embodiments of combinatorial formulations and coordinate treatment methods provided herein, the secondary therapeutic agent is anti-cocaine agent. Examples of useful anti-cocaine agents include, but are not limited to, desipramine, amantadine, fluoxidine, and buprenorphine.

In other embodiments of combinatorial formulations and coordinate treatment methods provided herein, the secondary therapeutic agent is an anti-lysergic acid diethylamide ("anti-LSD") agent. Examples of useful anti-LSD agents include, but are not limited to, diazepam.

In other embodiments of combinatorial formulations and coordinate treatment methods provided herein, the secondary therapeutic agent is an anti-phencyclidine ("anti-PCP") agent. Examples of useful anti-PCP agents include, but are not limited to, haloperidol.

In other embodiments of combinatorial formulations and coordinate treatment methods provided herein, the secondary therapeutic agent is an appetite suppressant. Examples of useful appetite suppressants include, but are not limited to, fenfluramine, phenylpropanolamine, and mazindol.

In yet additional embodiments of combinatorial formulations and coordinate treatment methods provided herein, the secondary therapeutic agent is an anti-Parkinson's-disease agent. Examples of useful anti-Parkinson's-disease agents include, but are not limited to dopamine precursors, such as levodopa, L-phenylalanine, and L-tyrosine; neuroprotective agents; dopamine agonists; dopamine reuptake inhibitors; anticholinergics such as amantadine and memantine; and 1,3,5-trisubstituted adamantanes, such as 1-amino-3,5-dimethyl-adamantane. (See, U.S. Pat. No. 4,122,193)

Mammalian subjects amenable for treatment according to the methods of the invention include, but are not limited to, human and other mammalian subjects suffering from a CNS disorder that is amenable to treatment or beneficial intervention using an active agent capable of inhibiting reuptake of norepinephrine, serotonin, and/or dopamine by interfering with the CNS conditions that are subject to treatment according to the methods and compositions of the invention include depression, as well as a variety of other neuropsychiatric conditions and disorders. Other disorders for which the compounds of the present invention may be useful include irritable bowel syndrome; inflammatory bowel disease; bulimia; anorexia; obesity and related eating disorders; urinary tract disorders, such as stress urinary incontinence; addictive disorders (including addiction to nicotine, stimulants, alcohol, and opiates); degenerative diseases, including Alzheimers disease, amyotrophic lateral sclerosis, and Parkinson's disease; and pyretic conditions (including fevers, and post- and peri-menopausal hot flashes). For each of the foregoing disorders, combinatorial formulations and coordinate treatment methods are provided within the scope of the invention comprising compounds of the invention coordinately administered or combinatorially formulated with a second therapeutic agent or method known for treating the subject disorder, and/or one or more symptom(s) associated therewith.

Subjects are effectively treated prophylactically and/or therapeutically by administering to the subject an effective amount of a compound of the invention, which is effective to treat, alleviate, prevent or eliminate a targeted CNS disorder in the subject, and/or one or more symptom(s) associated therewith, for example depression.

Administration of an effective amount of a compound of the present invention to a mammalian subject presenting with one or more of the foregoing CNS disorders and/or symptom(s) will detectably decrease, eliminate, or prevent the targeted CNS disorder and/or associated symptom(s). In exemplary embodiments, administration of a compound of the present invention to a suitable test subject will yield a reduction in the targeted CNS disorder, or one or more targeted symptom(s) associated therewith, such as depression, by at least 10%, 20%, 30%, 50% or greater, up to a 75-90%, or 95% or greater, reduction in the one or more target symptom(s), compared to placebo-treated or other suitable control subjects. Comparable levels of efficacy are contemplated for the entire range of CNS disorders described herein, including all contemplated neurological and psychiatric disorders, as well as all other CNS conditions and symptoms identified herein for treatment or prevention using the compositions and methods of the invention.

The active compounds of the invention may be optionally formulated with a pharmaceutically acceptable carrier and/or various excipients, vehicles, stabilizers, buffers, preservatives, etc. An "effective amount," "therapeutic amount," "therapeutically effective amount," or "effective dose" is an effective amount or dose of an active compound as described herein sufficient to elicit a desired pharmacological or therapeutic effect in a mammalian subject—typically resulting in a measurable reduction in an occurrence, frequency, or severity of one or more symptom(s) associated with or caused by a CNS disorder, including a neurological or psychological disease, condition, or disorder in the subject. In certain embodiments, when a compound of the invention is administered to treat a CNS disorder, for example depression, an effective amount of the compound will be an amount sufficient in vivo to delay or eliminate onset of symptoms of the targeted condition or disorder. Therapeutic efficacy can alternatively be demonstrated by a decrease in the frequency or severity of symptoms associated with the treated condition or disorder, or by altering the nature, recurrence, or duration of symptoms associated with the treated condition or disorder. Therapeutically effective amounts, and dosage regimens, of the compositions of the invention, including pharmaceutically effective salts, solvates, hydrates, polymorphs or prodrugs thereof, will be readily determinable by those of ordinary skill in the art, often based on routine clinical or patient-specific factors.

Suitable routes of administration for a compound of the present invention include, but are not limited to, oral, buccal, nasal, aerosol, topical, transdermal, mucosal, injectable, slow release, controlled release, iontophoresis, sonophoresis, and other conventional delivery routes, devices and methods. Injectable delivery methods are also contemplated, including but not limited to, intravenous, intramuscular, intraperitoneal, intraspinal, intrathecal, intracerebroventricular, intraarterial, and subcutaneous injection.

Suitable effective unit dosage amounts of arylbicyclo[3.1.0]hexylamines for mammalian subjects may range from about 1 to 1200 mg, 50 to 1000 mg, 75 to 900 mg, 100 to 800 mg, or 150 to 600 mg. In certain embodiments, the effective unit dosage will be selected within narrower ranges of, for example, 10 to 25 mg, 30 to 50 mg, 75 to 100 mg, 100 to 150 mg, 150 to 250 mg or 250 to 500 mg. These and other effective unit dosage amounts may be administered in a single dose, or in the form of multiple daily, weekly or monthly doses, for example in a dosing regimen comprising from 1 to 5, or 2-3, doses administered per day, per week, or per month. In exemplary embodiments, dosages of 10 to 25 mg, 30 to 50 mg, 75 to 100 mg, 100 to 200 (anticipated dosage strength) mg, or 250 to 500 mg, are administered one, two, three, or four times per day. In more detailed embodiments, dosages of 50-75 mg, 100-150 mg, 150-200 mg, 250-400 mg, or 400-600 mg are administered once, twice daily or three times daily. In alternate embodiments, dosages are calculated based on body weight, and may be administered, for example, in amounts from about 0.5 mg/kg to about 30 mg/kg per day, 1 mg/kg to about 15 mg/kg per day, 1 mg/kg to about 10 mg/kg per day, 2 mg/kg to about 20 mg/kg per day, 2 mg/kg to about 10 mg/kg per day or 3 mg/kg to about 15 mg/kg per day.

The amount, timing and mode of delivery of compositions of the invention comprising an effective amount of a compound of the present invention will be routinely adjusted on an individual basis, depending on such factors as weight, age, gender, and condition of the individual, the acuteness of the targeted CNS disorder and/or related symptoms, whether the administration is prophylactic or therapeutic, and on the basis of other factors known to effect drug delivery, absorption, pharmacokinetics, including half-life, and efficacy. An effective dose or multi-dose treatment regimen for the compounds of the invention will ordinarily be selected to approximate a minimal dosing regimen that is necessary and sufficient to substantially prevent or alleviate one or more symptom(s) of a neurological or psychiatric condition in the subject, as described herein. Thus, following administration of a compound of the present invention, test subjects will exhibit a 10%, 20%, 30%, 50% or greater reduction, up to a 75-90%, or 95% or greater, reduction, in one or more symptoms associated with a targeted CNS disorder, including any targeted neuropsychiatric disorder, such as depression, compared to placebo-treated or other suitable control subjects.

Within additional aspects of the invention, combinatorial formulations and coordinate administration methods are provided which employ an effective amount of a compound of the present invention—yielding an effective formulation or method to alleviate or prevent one or more symptom(s) of a CNS disorder in a mammalian subject.

Pharmaceutical dosage forms of a compound of the present invention may optionally include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives.

The compositions of the invention for treating CNS disorders, including depression, can thus include any one or combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to patients without causing deleterious side effects or interactions with the active agent.

If desired, a compound of the present invention can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps.

A compound of the present invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets, which may be prepared by any conventional method of preparing pharmaceutical oral unit dosage forms can be utilized in preparing oral unit dosage forms. Oral unit dosage forms, such as tablets, may contain one or more conventional additional formulation ingredients, including, but are not limited to, release modifying agents, glidants, compression aides, disintegrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants. The aforementioned effervescent agents and disintegrants are useful in the formulation of rapidly disintegrating tablets known to those skilled in the art. These typically disintegrate in the mouth in less than one minute, and preferably in less than thirty seconds. By effervescent agent is meant a couple, typically an organic acid and a carbonate or bicarbonate. Such rapidly acting dosage forms would be useful, for example, in the prevention or treatment of acute attacks of panic disorder.

The compounds and compositions of the invention can be prepared and administered in any of a variety of inhalation or nasal delivery forms known in the art. Devices capable of depositing aerosolized formulations of a compound of the present invention in the sinus cavity or pulmonary alveoli of a patient include metered dose inhalers, nebulizers, dry powder generators, sprayers, and the like. Pulmonary delivery to the lungs for rapid transit across the alveolar epithelium into the blood stream may be particularly useful in treating impending episodes of seizures or panic disorder. Methods and compositions suitable for pulmonary delivery of drugs for systemic effect are well known in the art. Suitable formulations, wherein the carrier is a liquid, for administration, as for example, a nasal spray or as nasal drops, may include aqueous or oily solutions of a compound of the present invention, and any additional active or inactive ingredient(s).

Intranasal delivery permits the passage of active compounds of the invention into the blood stream directly after administering an effective amount of the compound to the nose, without requiring the product to be deposited in the lung. In addition, intranasal delivery can achieve direct, or enhanced, delivery of the active compound to the CNS. In these and other embodiments, intranasal administration of the compounds of the invention may be advantageous for treating a variety of CNS disorders, including depression, by providing for rapid absorption and CNS delivery.

For intranasal and pulmonary administration, a liquid aerosol formulation will often contain an active compound of the invention combined with a dispersing agent and/or a physiologically acceptable diluent. Alternative, dry powder aerosol formulations may contain a finely divided solid form of the subject compound and a dispersing agent allowing for the ready dispersal of the dry powder particles. With either liquid or dry powder aerosol formulations, the formulation must be aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter, e.g., in a range of from about 2-5 microns, for nasal or pulmonary distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

Yet additional compositions and methods of the invention are provided for topical administration of a compound of the present invention for treating CNS disorders, including depression. Topical compositions may comprise a compound of the present invention and any other active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise a compound of the present invention dissolved or dispersed in a portion of a water or other solvent or liquid to be incorporated in the topical composition or delivery device. It can be readily appreciated that the transdermal route of administration may be enhanced by the use of a dermal penetration enhancer known to those skilled in the art. Formulations suitable for such dosage forms incorporate excipients commonly utilized therein, particularly means, e.g. structure or matrix, for sustaining the absorption of the drug over an extended period of time, for example 24 hours. A once-daily transdermal patch is particularly useful for a patient suffering from generalized anxiety disorder.

Yet additional formulations of a compound of the present invention are provided for parenteral administration, including aqueous and non-aqueous sterile injection solutions which may optionally contain anti-oxidants, buffers, bacteriostats and/or solutes which render the formulation isotonic with the blood of the mammalian subject; and aqueous and non-aqueous sterile suspensions which may include suspending agents and/or thickening agents. The formulations may be presented in unit-dose or multi-dose containers.

Formulations may also include polymers for extended release following parenteral administration. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In more detailed embodiments, a compound of the present invention may be encapsulated for delivery in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules) or in macroemulsions.

The pharmaceutical agents of the invention may be administered parenterally, e.g. intravenously, intramuscularly, subcutaneously or intraperitoneally. The parenteral preparations may be solutions, dispersions or emulsions suitable for such administration. The subject agents may also be formulated into polymers for extended release following parenteral administration. Pharmaceutically acceptable formulations and ingredients will typically be sterile or readily sterilizable, biologically inert, and easily administered. Such polymeric materials are well known to those of ordinary skill in the pharmaceutical compounding arts. Parenteral preparations typically contain buffering agents and preservatives, and may be lyophilized to be re-constituted at the time of administration.

The following examples illustrate certain embodiments of the present invention, and are not to be construed as limiting the present disclosure.

EXAMPLE I

Preparation of 1-(4-methylphenyl)-bicyclo[3.1.0] hexan-2-amines and 1-(4-methylphenyl)-bicyclo [3.1.0]hexan-3-amines using Reaction Schemes 1 and 2

A. Synthesis of 3-p-tolylprop-2-yn-1-ol

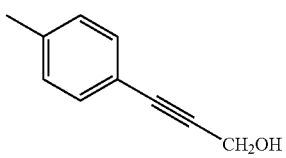

Bis(triphenylphosphine)palladium(II) chloride (120 mg; 0.171 mmol) was added to a stirred solution of propargyl alcohol (5.38 g; 95.88 mmol, 1.02 eq), 1-iodo-4-methylbenzene (20.50 g; 94.0 mmol, 1 eq), triethylamine (18.99 g; 188 mmol, 2 eq), and copper iodide (60 mg; 0.32 mmol) in THF (50 mL). The mixture was stirred at 35° C. for 12 h under a nitrogen atmosphere. The mixture was then filtered through a bed of celite and the filtrate was washed with ethyl acetate. The filtrate was then concentrated at 35° C. (vac.=28 in Hg) using a rotary evaporator. The residue was purified using a silica gel column (4:1 heptane/ethyl acetate→2:1 heptane/ethyl acetate) to give the desired product as a light yellow oil (9.62 g; 65.8 mmol; 70%). ¹H NMR (400 MHz, CHLOROFORM-d) δ ppm 2.34 (s, 3 H) 4.48 (s, 2H) 7.11 (d, 2H) 7.33 (d, 2H).

B. Synthesis of 3-p-tolylprop-2-yn-1-al

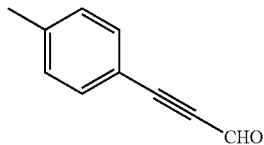

Pyridinium chlorochromate (22.1 g; 102.6 mmol; 2 eq) was added to a stirred solution of 3-p-tolylprop-2-yn-1-ol (7.5 g; 51.3 mmol) in dichloromethane (200 mL) at room temperature under nitrogen. The mixture was stirred for 4 h until TLC (2:1 heptane/ethyl acetate) indicated the disappearance of the starting propargyl alcohol. The mixture was then filtered through a bed of celite, and the filter cake was rinsed with dichloromethane (100 mL). The dichloromethane was concentrated using a rotary evaporator to give the desired product (4.22 g; 29.3 mmol; 57%) which was used in the next step without further purification. ¹H NMR (400 MHz, CHLOROFORM-d) δ ppm 2.39 (s, 3 H) 7.20 (d, 2H) 7.50 (d, 2H) 9.41 (s, 1H).

C. Synthesis of 1-p-tolyl-hex-5-en-1-yn-3-ol

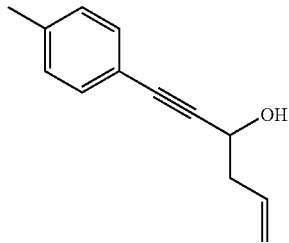

A solution of 3-p-tolylprop-2-yn-1-al (4.69 g; 32.5 mmol; 1 eq) in THF (40 mL) was added to a solution of allylmagnesium bromide (49 mL; 1M in $Et_{2O}$, 1.5 eq) at 0° C. over 25 minutes. Stirring was continued for an additional 2 h, and the reaction was carefully quenched with water (50 mL) at 0° C. MTBE (100 mL) was added, the layers were stirred, and then allowed to separate. The aqueous phase was re-extracted with MTBE (50 mL) and the combined organic layers were dried over sodium sulfate and filtered. The filtrate was concentrated using a rotary evaporator, and purification of the residue by flash chromatography (4:1→2:1 heptane/EtOAc) afforded the desired homoallylic alcohol (4.9 g; 26.3 mmol; 81%). ¹H NMR (400 MHz, CHLOROFORM-d) δ ppm 2.34 ((s, 3 H)) 2.56 (t, 2 H) 4.64 (t, 1H) 5.19-5.26 (m, 2H) 5.88-5.99 (m, 1H) 7.10 (d, 2H) 7.31 (d, 2H).

D. Synthesis of 1-p-tolyl-bicyclo[3.1.0]hexan-3-one

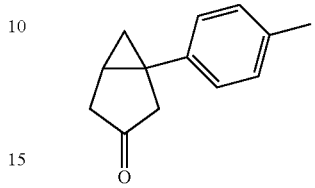

$PtCl_2$ (157 mg; 5 mol %) was added to a solution of 1-p-tolyl-hex-5-en-1-yn-3-ol (2.20 g; 11.8 mmol) in toluene (60 mL) and the resulting mixture was stirred at 80° C. for 24 h until the reaction was complete as shown by TLC. The toluene was concentrated at 45-50° C. using a rotary evaporator, and the residue was purified by flash chromatography (9:1→3:1 heptane/EtOAc) to give the desired product (880 mg; 40%). ¹H NMR (400 MHz, CHLOROFORM-d) δ ppm 0.68 (t, 1 H) 1.26-1.30 (m, 1 H) 1.92-1.97 (m, 1 H) 2.33 (s, 3 H) 2.39 (d, 1 H) 2.60-2.65 (d, 1H) 2.75-2.86 (m, 1 H) 2.88-2.93 (m, 1H) 7.07-7.14 (m, 4H).

E. Synthesis of 1-p-tolylhex-5-en-1-yn-3-yl acetate

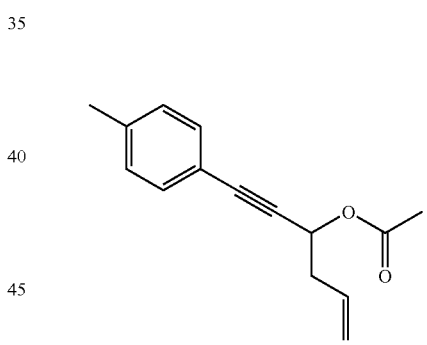

To a solution of 1-p-tolyl-hex-5-en-1-yn-3-ol (2.72 g; 14.6 mmol) in dichloromethane (20 mL) was added triethylamine (2 mL) and dimethylaminopyridine (178 mg; 1.46 mmol). The solution was cooled to 0° C. using an ice bath, and acetic anhydride (2.9 mL; 29.2 mmol) was slowly added to the solution. The mixture was allowed to warm to room temperature, and the reaction was stirred for an additional 2 h until TLC indicated that the reaction was complete. The mixture was then poured over ice (10 g), and the aqueous phase was re-extracted with dichloromethane (2×30 mL). The combined organic layers were dried, filtered, and concentrated using a rotary evaporator. The crude product was purified by flash chromatography (95:5 heptane/ethyl aceate) to give the desired acetate as a yellow oil (2.67 g; 80% yield). ¹H NMR (400 MHz, CHLOROFORM-d) δ ppm 2.10 (s, 3 H) 2.33 (s, 3 H) 2.61 (t, 2 H) 5.15-5.22 (m, 1 H) 5.59-5.68 (m, 1H) 5.80-5.96 (m, 1H) 7.10 (d, 2H) 7.32 (d, 2 H).

F. Synthesis of 1-p-tolyl-bicyclo[3.1.0]hexan-2-one

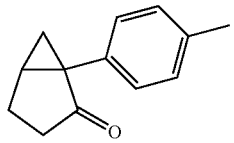

A solution of 1-p-tolylhex-5-en-1-yn-3-yl acetate (2.1 g; 9.2 mmol) in dichloromethane (30 mL) was added to a suspension of $(Ph_3P)AuCl$ (91 mg, 0.18 mmol) and $AgSbF_6$ (64 mg; 0.184 mmol) in dichloromethane (160 mL). After stirring at room temperature for 30 min, the solvent was evaporated and the crude product was dissolved in methanol (60 mL). Potassium carbonate (600 mg) was added and the suspension was stirred for 4 h before the reaction was quenched with water (40 mL). The methanol was removed by using a rotary evaporator. The aqueous phase was then extracted with MTBE (2×100 mL). The combined organic layers were then dried over magnesium sulfate and filtered. The filtrate was concentrated and the residue was purified by flash chromatography (heptane/ethyl acetate, 4:1) to give the desired ketone as a yellow liquid (616 mg; 36%). $^1$H NMR (400 MHz, CHLOROFORM-d) δ ppm 1.38 (t, 1 H) 1.54-1.57 (m, 1 H) 2.07-2.10 (m, 1 H) 2.25-2.28 (m, 2 H) 2.32 (s, 3 H) 2.34-2.38 (m, 2H) 7.12 (d, 2H) 7.19 (d, 2H).

G. Synthesis of 1-p-tolyl-bicyclo[3.1.0]hexan-3-amine hydrochloride

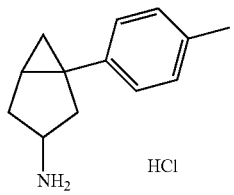

To a solution of 1-p-tolyl-bicyclo[3.1.0]hexan-3-one (140 mg; 0.75 mmol) in methanol (30 mL) was added ammonium acetate (5.7 g; 100 equivalent) and $NaCNBH_3$ (472 mg; 7.5 mmol). The mixture was heated to 60° C. and stirred for 2 hours. The reaction mixture was cooled to 10° C., and acidified with 1 N HCl (6 mL) taking care that the flask was vented into a bleach solution due to HCN evolution. The reaction mixture was concentrated at 30° C., and the resulting aqueous layer was diluted with $H_2O$ (10 mL). The aqueous layer was then extracted with ethyl acetate (15 mL) to remove nonpolar impurities. The aqueous layer was then adjusted to pH 9 with 1N NaOH, and the aqueous layer was extracted with ethyl acetate (2×20 mL). The combined organic layers were dried over $MgSO_4$, filtered, and concentrated to an oily residue. The oil was then dissolved in diethyl ether (5 mL), and the HCl salt was formed by slowly adding HCl/diethyl ether solution (0.5 mL). The slurry was stirred for 30 minutes before filtration. The solids were rinsed with diethyl ether (5 mL) and the compound was quickly transferred to a vacuum dessicator and dried under vacuum for 12 hours to afford a white solid (120 mg; 0.54 mmol; 72%). $^1$H NMR (400 MHz, CHLOROFORM-d) δ ppm 0.66-0.69 (m, 1 H) 0.76-0.79 (m, 1H) 1.10-1.20 (m, 1H) 1.52-1.57 (m, 1 H) 1.68-1.73 (dd, 1 H) 1.90-2.05 (m, 1 H) 2.11 (s, 3H) 2.19-2.29 (m, 1 H) 2.36-2.71 (m, 2 H) 3.08-3.29 (m, 1 H) 3.44-3.89 (m, 1 H) 6.71-7.01 (m, 4 H)). $^{13}$C NMR (100 MHz, CHLOROFORM-d) δ ppm 17.10 (s, 1 C) 21.16 (s, 1 C) 24.33 (s, 1 C) 24.70 (s, 1 C) 26.84 (s, 1 C) 30.53 (s, 1 C) 33.10 (s, 1C) 33.92 (s, 1 C) 35.52 (s, 1C) 37.80 (s, 1C) 40.27 (s, 1 C) 49.20 (s, 1 C) 53.23 (s, 1 C) 126.50 (s, 1 C) 126.58 (s, 1 C) 129.26 (s, 1 C) 135.74 (s, 1 C) 140.22 (s, 1 C) 140.58 (s, 1 C). MS (M+1) 188, HPLC purity 99% (AUC).

H. Synthesis of N-methyl-1-p-tolylbicyclo[3.1.0]hexan-3-amine hydrochloride

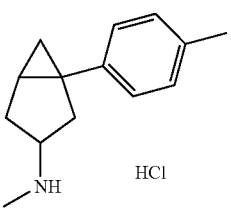

To a solution of 1-p-tolyl-bicyclo[3.1.0]hexan-3-one (90 mg; 0.48 mmol) in methanol (3 mL) was added methylamine (33% in ethanol; 1 mL) and $NaCNBH_3$ (39.2 mg; 0.62 mmol; 1.3 eq). The mixture was stirred at room temperature overnight. The reaction mixture was cooled to 10° C., and acidified with 1 N HCl (6 mL). The reaction mixture was concentrated at 30° C., and the resulting aqueous layer was diluted with $H_2O$ (10 mL). The aqueous layer was then extracted with ethyl acetate (15 mL) to remove nonpolar impurities. The aqueous layer was then adjusted to pH 9 with 1N NaOH, and the aqueous layer was extracted with ethyl acetate (2×20 mL). The combined organic layers were dried over $MgSO_4$, filtered, and concentrated to an oily residue. The oil was then dissolved in diethyl ether (5 mL), and the HCl salt was formed by slowly adding HCl/diethyl ether solution (0.5 mL). The slurry was stirred for 30 minutes before filtration. The solids were rinsed with diethyl ether (5 mL) and the compound was quickly transferred to a vacuum dessicator and dried under vacuum for 12 hours to give the title compound as a beige solid (65 mg; 57%). $^1$H NMR (400 MHz, CHLOROFORM-d) δ ppm 0.71-0.91 (m, 1 H) 1.20-1.29 (m, 1 H) 1.34-1.42 (m, 1 H) 1.64-1.75 (m, 1H) 2.01-2.14 (m, 1 H) 2.24-2.34 (m, 4 H) 2.35-2.51 (m, 2 H) 2.59-2.84 (m, 6 H) 3.70-3.86 (m, 1 H) 6.96-7.14 (m, 4 H) 9.23-9.68 (m, 1 H). $^{13}$C NMR (100 MHz, CHLOROFORM-d) δ ppm 16.90 (s, 1 C) 21.15 (s, 1 C) 24.06 (s, 1 C) 26.15 (s, 1 C) 26.73 (s, 1 C) 30.34 (s, 1 C) 31.52 (s, 1 C) 32.18 (s, 1 C) 32.54 (s, 1C) 33.93 (s, 1C) 36.22 (s, 1C) 38.99 (s, 1 C) 57.07 (s, 1C) 63.61 (s, 1C) 126.60 (s, 2 C) 129.30 (s, 2 C) 135.83 (s, 1 C) 140.61 (s, 1 C). MS (M+1) 202, HPLC Purity 98% (AUC).

I. Synthesis of N,N-dimethyl-1-p-tolyl-bicyclo[3.1.0]hexan-3-amine hydrochloride

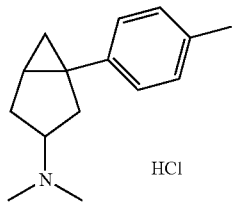

To a solution of 1-p-tolyl-bicyclo[3.1.0]hexan-3-one (147 mg; 0.79 mmol) in methanol (4 mL) was added dimethylamine (2M in THF; 1.6 mL) and NaCNBH$_3$ (64.5 mg; 1.03 mmol; 1.3 eq). The mixture was stirred at room temperature overnight. The reaction mixture was cooled to 10° C., and acidified with 1 N HCl (5 mL). The reaction mixture was concentrated at 30° C., and the resulting aqueous layer was diluted with H$_2$O (9 mL). The aqueous layer was then extracted with ethyl acetate (10 mL) to remove nonpolar impurities. The aqueous layer was then adjusted to pH 9 with 1N NaOH, and the aqueous layer was extracted with ethyl acetate (2×30 mL). The combined organic layers were dried over MgSO$_4$, filtered, and concentrated to an oily residue. The oil was then dissolved in diethyl ether (5 mL), and the HCl salt was formed by slowly adding HCl/diethyl ether solution (0.5 mL). The slurry was stirred for 30 minutes before filtration. The solids were rinsed with diethyl ether (5 mL) and the compound was quickly transferred to a vacuum dessicator and dried under vacuum for 12 hours to give the title compound as a pale yellow solid (68 mg; 34%). $^1$H NMR (400 MHz, CHLOROFORM-d) δ ppm 0.76-0.96 (m, 1H) 1.25-1.39 (m, 1 H) 1.66-1.77 (m, 1 H) 2.26-2.36 (m, 4 H) 2.42-2.56 (m, 1 H) 2.62 (m, 2 H) 2.69-2.84 (m, 6 H) 3.70-3.86 (m, 1 H) 6.99-7.13 (m, 4 H). $^{13}$C NMR (100 MHz, CHLOROFORM-d) d ppm 16.47 (s, 1 C) 21.18 (s, 1 C) 24.09 (s, 1 C) 24.95 (s, 1 C) 29.58 (s, 1 C) 30.90 (s, 1 C) 33.39 (s, 1C) 35.72 (s, 1C) 38.92 (s, 1C) 42.61 (s, 1 C) 65.18 (s, 1 C) 72.36 (s, 1 C) 126.79 (s, 2 C) 129.90 (s, 2 C) 129.33 (s, 1 C) 136.17 (s, 1 C) 139.36 (s, 1C). MS (M+1) 216, HPLC Purity 99% (AUC).

J. Synthesis of 1-p-tolyl-bicyclo[3.1.0]hexan-2-amine hydrochloride

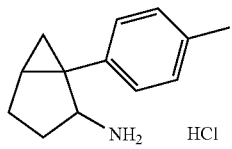

To a solution of 1-p-tolyl-bicyclo[3.1.0]hexan-2-one (178 mg; 0.96 mmol) in methanol (21 mL) was added ammonium acetate (5.7 g; 100 equivalents) and NaCNBH$_3$ (603 mg; 9.6 mmol). The mixture was heated to 60° C. and stirred for 3 hours. The reaction mixture was cooled to 10° C., and acidified with 1 N HCl (5 mL) taking care that the flask was vented into a bleach solution due to HCN evolution. The reaction mixture was concentrated at 30° C., and the resulting aqueous layer was diluted with H$_2$O (8 mL). The aqueous layer was then extracted with ethyl acetate (15 mL) to remove nonpolar impurities. The aqueous layer was then adjusted to pH 9 with 1N NaOH, and the aqueous layer was extracted with ethyl acetate (2×20 mL). The combined organic layers were dried over MgSO$_4$, filtered, and concentrated to an oily residue. The oil was then dissolved in diethyl ether (5 mL), and the HCl salt was formed by slowly adding HCl/diethyl ether solution (0.5 mL). The slurry was stirred for 30 minutes before filtration. The solids were rinsed with diethyl ether (5 mL) and the compound was quickly transferred to a vacuum dessicator and dried under vacuum for 12 hours to afford a white solid (135 mg; 76%). $^1$H NMR (400 MHz, Methanol-d4) δ ppm 0.64-0.91 (m, 1H) 1.07-1.22 (m, 1 H) 1.47-1.57 (m, 1H) 1.79-1.95 (m, 2 H) 2.02-2.25 (m, 2 H) 2.29-2.34 (m, 3 H) 3.28 (m, 1 H) 3.95-4.03 (m, 1 H) 7.13-7.30 (m, 4 H). $^{13}$C NMR (100 MHz, Methanol-d4) δ ppm 10.04 (s, 1 C) 16.02 (s, 1 C) 19.98 (s, 1 C) 22.57 (s, 1 C) 24.22 (s, 1 C) 25.31 (s, 1 C) 26.29 (s, 1 C) 26.76 (s, 1 C) 27.41 (s, 1 C) 34.30 (s, 1 C) 35.70 (s, 1 C) 56.40 (s, 1 C) 58.49 (s, 1 C) 128.44 (s, 1 C) 129.27 (s, 2 C) 129.49 (s, 1 C) 136.88 (s, 1 C) 138.01 (s, 1 C). MS (M+1) 188, HPLC purity 96% (AUC).

K. Synthesis of N-methyl-1-p-tolyl-bicyclo[3.1.0]hexan-2-amine tartrate

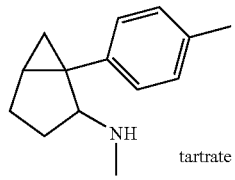

To a solution of 1-p-tolyl-bicyclo[3.1.0]hexan-2-one (113 mg; 0.61 mmol) in ethanol (3 mL) was added methylamine (33% in ethanol; 2 mL) and NaCNBH$_3$ (50 mg; 0.79 mmol; 1.3 eq). The mixture was stirred at room temperature overnight. The reaction mixture was cooled to 10° C., and acidified with 1 N HCl (3 mL). The reaction mixture was concentrated at 30° C., and the resulting aqueous layer was diluted with H$_2$O (10 mL). The aqueous layer was then extracted with ethyl acetate (15 mL) to remove nonpolar impurities. The aqueous layer was then adjusted to pH 9 with 1N NaOH, and the aqueous layer was extracted with ethyl acetate (2×20 mL). The combined organic layers were dried over MgSO$_4$, filtered, and concentrated to an oily residue. The oil was then dissolved in ethyl acetate/methanol (1:1, 5 mL), and the tartrate salt was formed by slowly adding L-tartaric acid (0.6 eq) to the solution. The slurry was stirred for 30 minutes before filtration. The solids were rinsed with diethyl ether (5 mL) and the compound was quickly transferred to a vacuum dessicator and dried under vacuum for 12 hours to give the title compound as a beige solid (98 mg; 46%). $^1$H NMR (400 MHz, CHLOROFORM-d) δ ppm 0.77-0.86 (m, 1 H) 1.21-1.46 (m, 2 H) 1.54-1.98 (m, 2 H) 1.96-2.48 (m, 8 H) 3.76-3.87 (m, 1 H) 6.98-7.11 (m, 4 H) 8.82-9.08 (bs, 1 H). $^{13}$C NMR (100 MHz, CHLOROFORM-d) d ppm 11.40 (s, 1 C) 21.25 (s, 1 C) 21.41 (s, 1 C) 25.67 (s, 1 C) 29.40 (s, 1 C) 33.18 (s, 1 C) 33.48 (s, 1

L. Synthesis of N,N-dimethyl-1-p-tolyl-bicyclo[3.1.0]hexan-2-amine hydrochloride

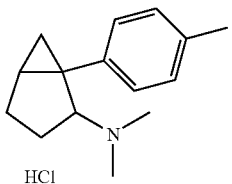

A mixture of 1-p-tolyl-bicyclo[3.1.0]hexan-2-one (139 mg, 0.75 mmol) in dichloromethane (6 mL) was cooled to 0° C. and dimethylamine (2M solution in THF, 1.1 mL, 2.2 mmol) and TiCl$_4$ (71 mg; 0.37 mmol) were added sequentially. After stirring at 0° C. for 45 min, the mixture was warmed to reflux and was stirred overnight. The reaction was then cooled to room temperature, and treated with sodium triacetoxyborohydride (226 mg, 1.06 mmol) at room temperature. The reaction mixture was stirred for 5 h, the reaction mixture was quenched with water (10 mL). The layers were filtered, and the pH was adjusted to 9 using saturated NaHCO$_3$. The layers were then separated, and the aqueous layer was re-extracted with CH$_2$Cl$_2$ (2×), dried over sodium sulfate, filtered and concentrated in vacuo. The oily crude residue was converted to HCl salt using HCl/diethyl ether to give the desired compound (79 mg; 42%). $^1$H NMR (400 MHz, CHLOROFORM-d) δ ppm 1.36 (m, 1 H) 1.50-1.66 (m, 1 H) 1.83-1.92 (m, 1 H) 2.01-2.21 (m, 4 H) 2.39-2.44 (m, 1 H) 2.55-2.90 (m, 6 H) 3.89-4.02 (m, 1 H) 7.01-7.33 (m, 4 H) 11.99 (bs, 1H). $^{13}$C NMR (100 MHz, CHLOROFORM-d) d ppm 11.54 (s, 1 C) 21.18 (s, 1 C) 25.78 (s, 1 C) 26.25 (s, 1 C) 30.67 (s, 1 C) 32.84 (s, 1 C) 43.01 (s, 1 C) 44.82 (s, 1 C) 75.27 (s, 1 C) 128.06 (s, 2 C) 130.02 (s, 2 C) 137.04 (s, 1 C) 138.76 (s, 1 C). MS (M+1) 216, HPLC Purity 95% (AUC).

EXAMPLE II

Preparation of 5-(4-methylphenyl)bicyclo[3.1.0]hexan-2-amines Using Reaction Scheme 3

A. Synthesis of 3-p-tolyl-cyclopent-2-en-1-one

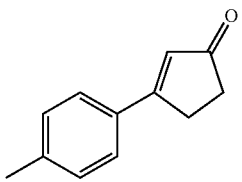

A solution of 4-iodotoluene (10 g, 45 mmol) in THF (300 mL) at −78° C. was treated with a solution of n-butyllithium (2.5 M in hexanes; 20 mL, 50 mmol) such that the reaction temperature remained ≦−78° C. After 15 minutes, a solution of 3-methoxy-2-cyclopenten-1-one (5.78 g, 52 mmol) in THF (50 mL) was added such that the reaction temperature remained ≦−78° C. The reaction mixture was warmed to −20° C. over 2 h, quenched with a solution of 1N HCl and concentrated in vacuo to remove THF. A solution of 1N HCl (40 mL) was added, the solution was stirred for 30 min and extracted with EtOAc (3×). The combined organic extracts were washed with saturated aqueous NaHCO$_3$, brine, dried over MgSO$_4$, filtered and concentrated in vacuo. The residue was purified by silica gel chromatography using heptane/EtOAc as the eluting solvent to afford 4.92 g of 3-p-tolyl-cyclopent-2-enone as a white powder (Yield 63.5%). $^1$H NMR (400 MHz, CHLOROFORM-d) δ ppm 2.42 (s, 3 H) 2.59 (ddd, J=4.83, 2.64, 2.49 Hz, 2 H) 3.05 (td, J=4.98, 1.76 Hz, 2 H) 6.55 (t, J=1.66 Hz, 1 H) 7.27 (d, J=8.00 Hz, 2 H) 7.57 (dt, J=8.30, 1.90 Hz, 2 H).

B. Synthesis of 3-p-tolyl-cyclopent-2-en-1-ol

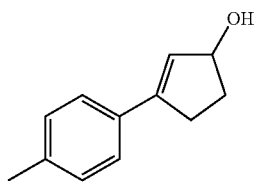

A solution of 3-p-tolyl-cyclopent-2-en-1-one (5.0 g, 29.07 mmol) in ethanol (100 mL) was treated with CeCl$_3$ (7.15 g, 29.07 mmol) followed portionwise by NaBH$_4$ (1.32 g, 34.9 mmol) at room temperature. The reaction mixture was stirred for 0.5 h, then quenched with saturated aqueous NH$_4$Cl and concentrated to remove ethanol. The concentrate was diluted with H$_2$O and extracted with DCM (3×). The combined organic extracts were dried over MgSO$_4$, filtered, concentrated in vacuo and purified by silica gel chromatography using 10-30% EtOAc/Heptane as the eluting solvent to afford 3.8 g (Yield 75%) of 3-p-tolyl-cyclopent-2-en-1-ol. $^1$H NMR (400 MHz, DMSO-d$_6$) δ ppm 1.15-1.31 (m, 1 H) 1.55-1.73 (m, 1 H) 2.17-2.26 (m, 1 H) 2.22-2.32 (m, 3 H) 2.41-2.54 (m, 1 H) 2.66-2.78 (m, 1 H) 4.72 (d, 1 H) 4.74-4.80 (m, 1 H) 6.12-6.17 (m, 1 H) 7.13 (d, 2 H) 7.36 (d, 2 H)

C. Synthesis of 5-p-tolyl-bicyclo[3.1.0]hexan-2-ol

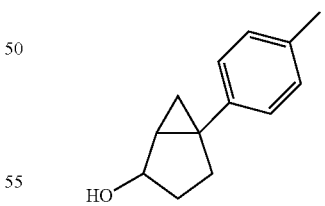

A solution of allylic alcohol 3-p-tolyl-cyclopent-2-en-1-ol (0.6 g, 3.44 mmol) in CH$_2$Cl$_2$ (50 mL) was treated with Et$_2$Zn (1.0M in hexane; 17 mL, 17 mmol). After 10 min, the reaction mixture was cooled to 0° C., treated with a solution of CH$_2$I$_2$ (1.4 mL, 17.3 mmol) in CH$_2$Cl$_2$ (10 mL) dropwise over 10 min and allowed to warm to ambient temperature. After 2 h, the reaction mixture was quenched with saturated aqueous NH$_4$Cl. The reaction mixture was extracted with CH$_2$Cl$_2$ (3×). The combined organic phases were dried over MgSO$_4$ and concentrated in vacuo. Purification of the crude material by silica gel chromatography using 10-30% EtOAc/Heptane as the eluting solvent provided the target compound (500 mg, 77%). $^1$H NMR (400 MHz, CHLOROFORM-d) δ ppm 0.77-0.86 (m, 1 H) 1.18-1.34 (m, 2 H) 1.52-1.57 (m, 1 H) 1.81-1.87 (m, 1 H) 1.97-2.19 (m, 2 H) 2.29-2.33 (m, 3 H) 4.61-4.75 (m, 1 H) 7.00-7.13 (m, 4 H).

D. Synthesis of 5-p-tolyl-bicyclo[3.1.0]hexan-2-one

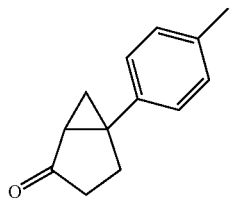

A solution of 5-p-tolyl-bicyclo[3.1.0]hexan-2-ol (1 g, 5.3 mmol) in CH$_2$Cl$_2$ (20 mL) was treated with pyridine (0.6 mL, 7.4 mmol) followed by Dess-Martin periodinane (2.7 g, 6.3 mmol) and warmed to ambient temperature. After 2 h, 3 drops of H$_2$O were added. After 0.5 h, the reaction was quenched with saturated NaHCO$_3$, saturated Na$_2$SO$_3$ and extracted with CH$_2$Cl$_2$ (3×). The combined organic extracts were dried and concentrated in vacuo. Purification by silica gel chromatography gave the target compound (760 mg, 77%). $^1$H NMR (400 MHz, CHLOROFORM-d) δ ppm 1.42-1.47 (m, 1 H) 1.53-1.61 (m, 1 H) 2.06-2.11 (m, 1 H) 2.20-2.29 (m, 2 H) 2.30-2.36 (m, 1 H) 2.32-2.34 (m, 3 H) 2.37-2.45 (m, 1 H) 7.08-7.18 (m, 4 H).

E. Synthesis of 5-p-tolyl-bicyclo[3.1.0]hexan-2-amine hydrochloride

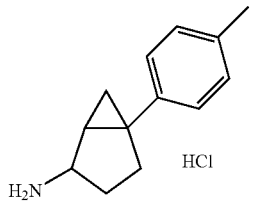

To a solution of 5-p-tolyl-bicyclo[3.1.0]hexan-2-one (100 mg, 0.54 mmol) and anhydrous NaOAc (87.5 mg, 1.1 mmol) in anhydrous MeOH (10 mL) was added with stirring NH$_2$OH.HCl (69.5 mg, 1 mmol). The resulting mixture was stirred at room temperature for 18 h. The reaction mixture was filtered and the filtrate was concentrated in vacuo. The residue, dioxime [IS THIS CORRECT?] was reconstituted in anhydrous MeOH (5 ml) and anhydrous NiCl$_2$ (194 mg, 1.5 mmol) was added with stirring. The reaction mixture was cooled to −30° C. and NaBH$_4$ (567 mg, 15 mmol) was added in small portions. After completion of the addition the mixture was allowed to warm to room temperature and concentrated in vacuo. This was then basified with aqueous solution of NaOH and extracted with CH$_2$Cl$_2$ (3×). Organic phases were concentrated and purified by silica gel chromatography. The oily product was converted to HCl salt (62 mg, 51%).

$^1$H NMR (500 MHz, DMSO-d$_6$) δ ppm 0.84-0.91 (m, 1 H) 1.27-1.37 (m, 1 H) 1.68-1.74 (m, 1 H) 1.76-1.81 (m, 1 H) 1.94-2.03 (m, 1 H) 2.04-2.12 (m, 1 H) 2.19-2.25 (m, 3 H) 2.26-2.36 (m, 1 H) 3.56-3.62 (m, 1 H) 3.80-3.91 (m, 1 H) 6.95-7.19 (m, 4 H) 8.07-8.25 (broad, 1 H). $^{13}$C NMR (500 MHz, DMSO-d$_6$) d ppm 13.77 (s, 1 C) 15.98 (s, 1 C) 20.33 (s, 1 C) 25.11 (s, 1 C) 26.28 (s, 1 C) 26.96 (s, 1 C) 28.46 (s, 1 C) 28.50 (s, 1 C) 30.22 (s, 1 C) 31.68 (s, 1 C) 32.07 (s, 1 C) 51.86 (s, 1 C) 52.86 (s, 1 C) 125.93 (s, 1 C) 126.21 (s, 1 C) 128.53 (s, 1 C) 128.68 (s, 1 C) 134.63 (s, 1 C) 134.77 (s, 1 C) 139.98 (s, 1 C) 140.13 (s, 1 C). MS (M+1) 188.

F. Synthesis of N-methyl-5-p-tolyl-bicyclo[3.1.0]hexan-2-amine hydrochloride

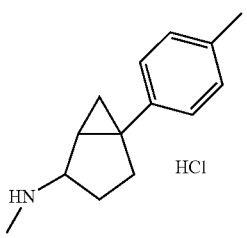

A solution of ketone 5-p-tolyl-bicyclo[3.1.0]hexan-2-one (140 mg, 0.75 mmol) was treated with a solution of methylamine (33% in absolute ethanol, 30 ml), followed by the addition of titanium (IV) isopropoxide (427 mg, 1.5 mmol). The reaction mixture was stirred for 5 h, then sodium borohydride (55 mg, 1.5 mmol) was added. After 1 h, the reaction mixture was concentrated, aqueous solutions of sodium bicarbonate and sodium sulfate were added and this was extracted with CH$_2$Cl$_2$ (3×), dried over K$_2$CO$_3$, filtered and concentrated in vacuo. The oily crude residue was converted to HCl salt (134 mg, 75%). $^1$H NMR (400 MHz, DMSO-d$_6$) δ ppm 0.78-0.86 (m, 1 H) 1.31-1.46 (m, 2 H) 1.84-1.91 (m, 1 H) 1.96-2.08 (m, 2 H) 2.08-2.15 (m, 1 H) 2.08-2.15 (m, 1 H) 2.21-2.25 (m, 3 H) 2.55 (t, 3 H) 3.76-3.87 (m, 1 H) 7.02-7.11 (m, 4 H) 8.82-9.08 (m, 1 H). $^{13}$C NMR (400 MHz, METHANOL-d$_4$) d ppm 11.82 (s, 1 C) 18.38 (s, 1 C) 23.03 (s, 1 C) 23.91 (s, 1 C) 29.42 (s, 1 C) 30.04 (s, 1 C) 31.22 (s, 1 C) 60.14 (s, 1 C) 124.84 (s, 2 C) 127.36 (s, 2 C) 134.28 (s, 1 C) 138.33 (s, 1 C). MS (M+1) 202.

G. Synthesis of N,N-dimethyl-5-p-tolyl-bicyclo[3.1.0]hexan-2-amine hydrochloride

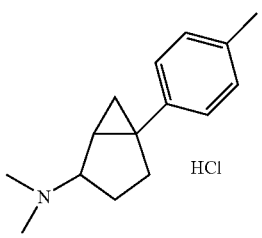

The mixture of 5-p-tolyl-bicyclo[3.1.0]hexan-2-one (100 mg, 0.535 mmol) in DCE (3 mL) and dimethylamine (2M solution in THF, 6 mL, 5.3 mmol) was treated with sodium triacetoxyborohydride (113 mg, 0.53 mmol) at room temperature. The reaction mixture was stirred for 5 h, then the reaction mixture was concentrated, diluted with saturated NaHCO$_3$, extracted with CH$_2$Cl$_2$ (3×), dried over K$_2$CO$_3$, filtered and concentrated in vacuo. The oily crude residue was converted to HCl salt (124 mg, 91.7%). $^1$H NMR (400 MHz, CHLOROFORM-d) δ ppm 1.16 (t, 1 H) 1.73-1.80 (m, 1 H) 1.90-1.95 (m, 1 H) 2.01-2.21 (m, 3 H) 2.33-2.38 (m, 1 H) 2.81 (d, 2 H) 2.91 (d, 3 H) 3.70-3.84 (m, 1 H) 7.01-7.13 (m, 4 H). $^{13}$C NMR (400 MHz, CHLOROFORM-d) d ppm 15.70 (s, 1 C) 21.20 (s, 1 C) 24.79 (s, 1 C) 25.82 (s, 1 C) 31.66 (s, 1 C) 33.81 (s, 1 C) 43.55 (s, 1 C) 43.69 (s, 1 C) 70.51 (s, 1 C) 126.70 (s, 2C) 129.38 (s, 2C) 136.31 (s, 1C) 139.58 (s, 1 C). MS (M+1) 216.

EXAMPLE III

Preparation of 1-(3,4-dichlorophenyl)-bicyclo[3.1.0]hexan-2-amines and 1-(3,4-dichlorophenyl)-bicyclo[3.1.0]hexan-3-amines Using Reaction Schemes 1 and 2

A. Synthesis of 3-(3,4-dichlorophenyl)prop-2-yn-1-ol

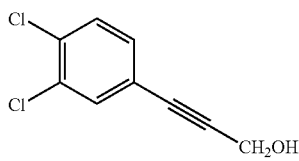

Bis(triphenylphosphine)palladium(II) chloride (120 mg; 0.171 mmol) was added to a stirred solution of propargyl alcohol (5.24 g; 93.4 mmol; 1.02 eq), 1-iodo-3,4-dichlorobenzene (25.0 g; 91.6 mmol, 1 eq), triethylamine (18.5 g; 183.2 mmol, 2 eq), and copper iodide (60 mg; 0.32 mmol) in THF (50 mL). The mixture was stirred at 35° C. for 12 h under a nitrogen atmosphere. The mixture was then filtered through a bed of celite and the filtrate was washed with ethyl acetate. The filtrate was then concentrated at 35° C. (vac.=28 in Hg) using a rotary evaporator. The residue was purified using a silica gel column (4:1 heptane/ethyl acetate→2:1 heptane/ethyl acetate) to give the desired product as a light yellow solid (17.10 g; 85.2 mmol; 93%). $^1$H NMR (400 MHz, CHLOROFORM-d) δ ppm 4.53 (s, 2H) 7.19 (d, 1H) 7.29 (d, 1H) 7.49 (s, 1H).

B. Synthesis of 3-(3,4-dichlorophenyl)prop-2-yn-1-al

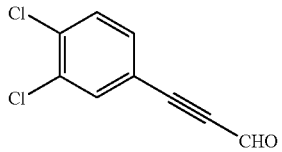

Pyridinium chlorochromate (24.23 g; 112.4 mmol; 2 eq) was added to a stirred solution of 3-(3,4-dichlorophenyl)prop-2-yn-1-ol (11.3 g; 56.2 mmol) in dichloromethane (225 mL) at room temperature. The mixture was stirred for 3.5 h until TLC (2:1 heptane/ethyl acetate) indicated the disappearance of the starting propargyl alcohol. The mixture was then filtered through a bed of celite, and the filter cake was rinsed with dichloromethane (150 mL). The dichloromethane was concentrated using a rotary evaporator to give the desired product (5.48 g; 27.5 mmol; 49%) which was used in the next step without further purification. $^1$H NMR (400 MHz, CHLOROFORM-d) δ ppm 7.20 (d, 1H) 7.31 (d, 1H) 7.51 (s, 1H) 9.43 (s, 1H).

C. Synthesis of 1-(3,4-dichlorophenyl)hex-5-en-1-yn-3-ol

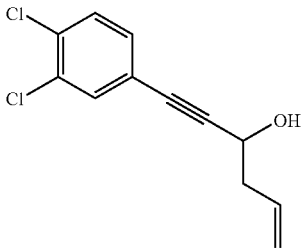

A solution of 3-(3,4-dichlorophenyl)prop-2-yn-1-al (6.46 g; 32.4 mmol; 1 eq) in THF was added to a solution of allylmagnesium bromide (48.5 mL; 1M in Et$_{2O}$, 1.5 eq) at 0° C. over 25 minutes. Stirring was continued for an additional 2 h, and the reaction was carefully quenched with water (50 mL) at 0° C. MTBE (100 mL) was added, and the layers were stirred and allowed to separate. The aqueous phase was re-extracted with MTBE (50 mL) and the combined organic layers were dried over sodium sulfate and filtered. The filtrate was concentrated using a rotary evaporator, and purification of the residue by flash chromatography (4:1→1:1 heptane/EtOAc) afforded the desired homoallylic alcohol (5.86 g; 24.3 mmol; 75%). $^1$H NMR (400 MHz, CHLOROFORM-d) δ ppm 2.56 (t, 2 H) 4.63 (t, 1H) 5.21-5.29 (m, 2H) 5.85-5.97 (m, 1H) 7.21 (d, 1H) 7.37 (d, 1H) 7.51 (s, 1H).

D. Synthesis of 1-(3,4-dichlorophenyl)bicyclo[3.1.0]hexan-3-one

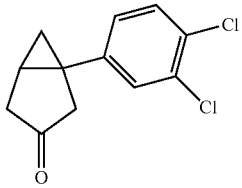

PtCl$_2$ (5 mol %) was added to a solution of 1-(3,4-dichlorophenyl)hex-5-en-1-yn-3-ol (2.98 g; 12.36 mmol) in toluene (65 mL) and the resulting mixture was stirred at 80° C. for 30 h until the reaction was complete by TLC. The toluene was concentrated at 45-50° C. using a rotary evaporator, and the residue was purified by flash chromatography (9:1→2:1 heptane/EtOAc) to give the desired product (895 mg; 30%). $^1$H NMR (400 MHz, CHLOROFORM-d) δ ppm 0.68 (t, 1 H) 1.25-1.30 (m, 1 H) 1.90-1.99 (m, 1 H) 2.36-2.41 (d, 1 H) 2.59-2.64 (d, 1 H) 2.80-2.89 (m, 2 H) 7.00 (d, 1H) 7.25 (s, 1H) 7.37 (d, 1 H).

E. Synthesis of 1-(3,4-dichlorophenyl)hex-5-en-1-yn-3-yl acetate

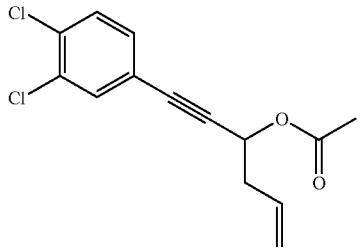

To a solution of alcohol 1-(3,4-dichlorophenyl)hex-5-en-1-yn-3-ol (3.12 g; 12.9 mmol) in dichloromethane (20 mL) was added triethylamine (2 mL) and dimethylaminopyridine (315 mg; 2.58 mmol). The solution was cooled to 0° C. using an ice bath, and acetic anhydride (3 mL; 30.7 mmol) was slowly added to the solution. The mixture was allowed to warm to room temperature, and the reaction was stirred for an additional 2 h until TLC indicated that the reaction was complete. The mixture was then poured over ice (10 g), and the aqueous phase was re-extracted with dichloromethane (2×30 mL). The combined organic layers were dried, filtered, and concentrated using a rotary evaporator. The crude product was purified by flash chromatography (95:5 heptane/ethyl aceate) to give the desired acetate as a yellow oil (3.03 g; 83% yield). $^1$H NMR (400 MHz, CHLOROFORM-d) δ ppm 2.10 (s, 3H) 2.58 (t, 2 H) 5.20 (m, 2H) 5.60 (t, 1H) 5.80-5.92 (m, 1H) 7.25 (d, 1H) 7.38 (d, 1H) 7.52 (s, 1H).

F. Synthesis of 1-(3,4-dichlorophenyl)bicyclo[3.1.0]hexan-2-one

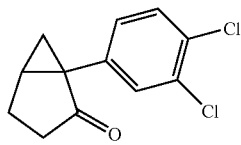

A solution of 1-(3,4-dichlorophenyl)hex-5-en-1-yn-3-yl acetate (2.6 g; 9.18 mmol) in dichloromethane (30 mL) was added to a suspension of (Ph$_3$P)AuCl (91 mg, 0.18 mmol) and AgSbF$_6$ (64 mg; 0.18 mol) in dichloromethane (150 mL). After stirring at room temperature for 50 min, the solvent was evaporated and the crude product was dissolved in methanol (80 mL). Potassium carbonate (800 mg) was added and the suspension was stirred for 4 h before the reaction was quenched with water (50 mL). The methanol was removed by using a rotary evaporator. The aqueous phase was then extracted with MTBE (2×100 mL). The combined organic layers were then dried over magnesium sulfate and filtered. The filtrate was concentrated and the residue was purified by flash chromatography (heptane/ethyl acetate 4:1) to give the desired ketone as a yellow liquid (553 mg; 25%). $^1$H NMR (400 MHz, CHLOROFORM-d) δ ppm 1.45 (t, 1 H) 1.51-1.56 (m, 1 H) 2.09-2.13 (m, 1 H) 2.27-2.31 (m, 3 H) 2.40-2.43 (m, 1 H) 7.16 (d, 1H) 7.36 7.41 (m, 2H).

G. Synthesis of 1-(3,4-dichlorophenyl)bicyclo[3.1.0]hexan-3-amine hydrochloride

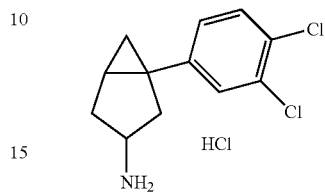

To a solution of 1-(3,4-dichlorophenyl)bicyclo[3.1.0] hexan-3-one (160 mg; 0.66 mmol) in methanol (20 mL) was added ammonium acetate (5.08 g; 100 equivalent) and NaCNBH$_3$ (332 mg; 5.28 mmol). The mixture was heated to 60° C. and stirred for 2 hours. The reaction mixture was cooled to 10° C., and acidified with 1 N HCl (6 mL) taking care that the flask was vented into a bleach solution due to HCN evolution. The reaction mixture was concentrated at 30° C., and the resulting aqueous layer was diluted with H$_2$O (10 mL). The aqueous layer was then extracted with ethyl acetate (15 mL) to remove nonpolar impurities. The aqueous layer was then adjusted to pH 9 with 1N NaOH, and the aqueous layer was extracted with ethyl acetate (2×20 mL). The combined organic layers were dried over MgSO$_4$, filtered, and concentrated to an oily residue. The oil was then dissolved in diethyl ether (5 mL), and the HCl salt was formed by slowly adding HCl/diethyl ether solution (0.5 mL). The slurry was stirred for 30 minutes before filtration. The solids were rinsed with diethyl ether (5 mL) and the compound was quickly transferred to a vacuum dessicator and dried under vacuum for 12 hours to afford a white solid (146 mg; 80%). $^1$H NMR (400 MHz, Methanol-d4) δ ppm 0.99-1.04 (t, 2 H) 1.24-1.30 (m, 1 H) 1.77-1.89 (m, 3 H) 2.08-2.19 (m, 2H) 2.58-2.78 (m, 3H) 3.97-4.03 (m, 1H) 7.08-7.17 (m, 1 H) 7.32-7.45 (m, 2 H). $^{13}$C NMR (100 MHz, Methanol-d4) δ ppm 17.34 (s, 1 C) 24.74 (s, 1 C) 24.92 (s, 1 C) 27.10 (s, 1 C) 32.34 (s, 1 C) 33.18 (s, 1 C) 34.55 (s, 1 C) 36.46 (s, 1 C) 39.32 (s, 1 C) 53.20 (s, 1 C) 125.92 (s, 1 C) 126.41 (s, 1 C) 128.58 (s, 1 C) 130.31 (s, 1 C) 132.01 (s, 1 C) 144.75 (s, 1 C). MS (M+1) 242, HPLC purity 99% (AUC).

H. Synthesis of N-methyl-1-(3,4-dichlorophenyl) bicyclo[3.1.0]hexan-3-amine hydrochloride

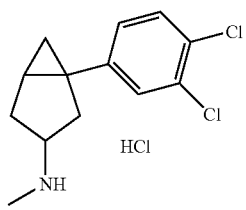

To a solution of 1-(3,4-dichlorophenyl)bicyclo[3.1.0] hexan-3-one (100 mg; 0.41 mmol) in methanol (3 mL) was added methylamine (33% in ethanol; 1 mL) and NaCNBH$_3$ (33 mg; 0.53 mmol; 1.3 eq). The mixture was stirred at room temperature overnight. The reaction mixture was cooled to 10° C., and acidified with 1 N HCl (4 mL). The reaction mixture was concentrated at 30° C., and the resulting aqueous layer was diluted with H₂O (10 mL). The aqueous layer was then extracted with ethyl acetate (15 mL) to remove nonpolar impurities. The aqueous layer was then adjusted to pH 9 with 1N NaOH, and the aqueous layer was extracted with ethyl acetate (2×20 mL). The combined organic layers were dried over MgSO₄, filtered, and concentrated to an oily residue. The oil was then dissolved in diethyl ether (5 mL), and the HCl salt was formed by slowly adding HCl/diethyl ether solution (0.5 mL). The slurry was stirred for 30 minutes before filtration. The solids were rinsed with diethyl ether (5 mL) and the compound was quickly transferred to a vacuum dessicator and dried under vacuum for 12 hours to give the title compound as a beige solid (76 mg; 64%). ¹H NMR (400 MHz, CHLOROFORM-d) δ ppm 0.78-0.93 (m, 1 H) 1.19-1.27 (m, 1 H) 1.44-1.50 (m, 1H) 1.67-1.80 (m, 1H) 2.03-2.13 (m, 1 H) 2.35-2.50 (m, 3 H) 2.55-2.73 (m, 7 H) 3.11-3.35 (m, 1 H) 3.74-3.88 (m, 1 H) 7.16 (dd, 1 H) 7.23-7.41 (m, 2 H). ¹³C NMR (100 MHz, CHLOROFORM-d) δ ppm 17.41 (s, 1 C) 24.68 (s, 1 C) 26.81 (s, 1 C) 27.02 (s, 1 C) 30.08 (s, 1 C) 31.31 (s, 1 C) 32.24 (s, 1 C) 32.58 (s, 1C) 33.62 (s, 1C) 35.90 (s, 1C) 38.455 (s, 1C) 59.96 (s, 1 C) 63.08 (s, 1 C) 126.08 (s, 1 C) 128.75 (s, 1 C) 130.53 (s, 1 C) 132.59 (s, 1 C) 143.92 (s, 1 C). MS (M+1) 256.0, HPLC Purity 99% (AUC).

I. Synthesis of N,N-dimethyl-1-(3,4-dichlorophenyl) bicyclo[3.1.0]hexan-3-amine hydrochloride

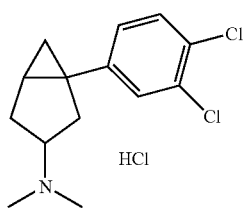

To a solution of 1-(3,4-dichlorophenyl)bicyclo[3.1.0] hexan-3-one (112 mg; 0.46 mmol) in methanol (4 mL) was added dimethylamine (2M in THF; 2 mL) and NaCNBH₃ (37.5 mg; 0.60 mmol; 1.3 eq). The mixture was stirred at room temperature overnight. The reaction mixture was cooled to 10° C., and acidified with 1 N HCl (4 mL). The reaction mixture was concentrated at 30° C., and the resulting aqueous layer was diluted with H₂O (8 mL). The aqueous layer was then extracted with ethyl acetate (15 mL) to remove nonpolar impurities. The aqueous layer was then adjusted to pH 9 with 1N NaOH, and the aqueous layer was extracted with ethyl acetate (2×20 mL). The combined organic layers were dried over MgSO₄, filtered, and concentrated to an oily residue. The oil was then dissolved in diethyl ether (5 mL), and the HCl salt was formed by slowly adding HCl/diethyl ether solution (0.5 mL). The slurry was stirred for 30 minutes before filtration. The solids were rinsed with diethyl ether (5 mL) and the compound was quickly transferred to a vacuum dessicator and dried under vacuum for 12 hours to give the title compound as a beige solid (84 mg; 73%). ¹H NMR (400 MHz, CHLOROFORM-d) δ ppm 0.68-0.77 (m, 1H) 1.11 (t, 1 H) 1.67-1.79 (m, 1 H) 2.03-2.14 (m, 2 H) 2.36-2.55 (m, 2 H) 2.57-2.72 (m, 6 H) 3.09-3.17 (m, 1 H) 6.88 (dd, 1 H) 7.08 (dd, 2 H) 12.07-12.30 (broad, 1 H). ¹³C NMR (100 MHz, CHLOROFORM-d) δ ppm 16.91 (s, 1 C) 24.47 (s, 1 C) 25.70 (s, 1 C) 29.40 (s, 1 C) 30.84 (s, 1 C) 33.16 (s, 1 C) 35.32 (s, 1 C) 38.37 (s, 1 C) 64.80 (s, 1 C) 71.70 (s, 1 C) 126.13 (s, 1 C) 128.64 (s, 1 C) 128.93 (s, 1 C) 130.44 (s, 1 C) 132.44 (s, 1 C) 143.75 (s, 1 C). MS (M+1) 270.1, HPLC Purity 95% (AUC).

J. Synthesis of 1-(3,4-dichlorophenyl)bicyclo[3.1.0]hexan-2-amine hydrochloride

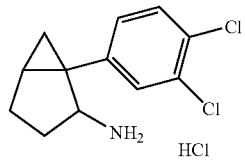

To a solution of 1-(3,4-dichlorophenyl)bicyclo[3.1.0] hexan-2-one (160 mg; 0.66 mmol) in methanol (5 mL) was added ammonium acetate (5.2 g; 100 equivalent) and NaCNBH₃ (415 mg; 6.6 mmol; 10 eq). The mixture was heated to 60° C. and stirred for 3 hours. The reaction mixture was cooled to 10° C., and acidified with 1 N HCl (5 mL) taking care that the flask was vented into a bleach solution due to HCN evolution. The reaction mixture was concentrated at 30° C., and the resulting aqueous layer was diluted with H₂O (10 mL). The aqueous layer was then extracted with ethyl acetate (15 mL) to remove nonpolar impurities. The aqueous layer was then adjusted to pH 9 with 1N NaOH, and the aqueous layer was extracted with ethyl acetate (2×20 mL). The combined organic layers were dried over MgSO₄, filtered, and concentrated to an oily residue. The oil was then dissolved in diethyl ether (5 mL), and the HCl salt was formed by slowly adding HCl/diethyl ether solution (0.5 mL). The slurry was stirred for 30 minutes before filtration. The solids were rinsed with diethyl ether (5 mL) and the compound was quickly transferred to a vacuum dessicator and dried under vacuum for 12 hours to give a white solid (111 mg; 61%). ¹H NMR (400 MHz, Methanol-d4) δ ppm 0.68-0.76 (m, 1 H) 1.04-1.11 (m, 1 H) 1.14-1.22 (m, 1 H) 1.25-1.32 (m, 1 H) 1.37-1.51 (m, 1 H) 1.58-1.67 (m, 1 H) 1.78-1.98 (m, 4H) 2.04-2.13 (m, 1H) 2.20-2.33 (m, 3H) 3.97-4.03 (m, 1H) 4.08-4.19 (m, 1H) 7.30-7.42 (m, 1 H) 7.46-7.54 (m, 2 H). ¹³C NMR (100 MHz, Methanol-d4) δ ppm 10.50 (s, 1 C) 16.30 (s, 1 C) 23.03 (s, 1 C) 24.13 (s, 1 C) 25.20 (s, 1 C) 26.30 (s, 1 C) 26.74 (s, 1 C) 28.33 (s, 1 C) 33.88 (s, 1 C) 35.27 (s, 1 C) 56.08 (s, 1 C) 57.95 (s, 1 C) 128.54 (s, 1 C) 129.49 (s, 1 C) 130.73 (s, 1 C) 130.90 (s, 1 C) 131.63 (s, 1 C) 132.47 (s, 1 C) 138.91 (s, 1 C) 141.04 (s, 1 C). MS (M+1) 242, HPLC purity 95% (AUC).

K. Synthesis of N-methyl-1-(3,4-dichlorophenyl) bicyclo[3.1.0]hexan-2-amine tartrate

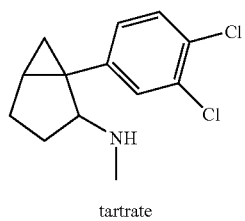

To a solution of 1-(3,4-dichlorophenyl)bicyclo[3.1.0]hexan-2-one (169 mg; 0.70 mmol) in ethanol (3.5 mL) was added methylamine (33% in ethanol; 2 mL) and NaCNBH$_3$ (57 mg; 0.91 mmol; 1.3 eq). The mixture was stirred at room temperature overnight. The reaction mixture was cooled to 10° C., and acidified with 1 N HCl (4 mL). The reaction mixture was concentrated at 30° C., and the resulting aqueous layer was diluted with H$_2$O (14 mL). The aqueous layer was then extracted with ethyl acetate (10 mL) to remove nonpolar impurities. The aqueous layer was then adjusted to pH 9 with 1N NaOH, and the aqueous layer was extracted with ethyl acetate (2×30 mL). The combined organic layers were dried over MgSO$_4$, filtered, and concentrated to an oily residue. The oil was then dissolved in ethyl acetate/methanol (1:1; 5 mL), and the tartrate salt was formed by slowly adding L-tartaric acid (0.5 eq) to the solution. The slurry was stirred for 30 minutes before filtration. The solids were rinsed with diethyl ether (5 mL) and the compound was quickly transferred to a vacuum dessicator and dried under vacuum for 12 hours to give the title compound as a white solid (100 mg; 35%). $^1$H NMR (400 MHz, CHLOROFORM) δ ppm 0.89-0.97 (m, 1 H) 1.34-1.50 (m, 2 H) 1.93-2.09 (m, 3 H) 2.09-2.19 (m, 1 H) 2.28-2.36 (m, 3 H) 3.25-3.35 (m, 1 H) 3.76-3.85 (m, 1 H) 7.17 (dd, 1 H) 7.42 (d, 1 H) 7.52 (d, 1 H) 7.90-8.42 (broad, 1 H). $^{13}$C NMR (100 MHz, CHLOROFORM-d) d ppm 25.48 (s, 1 C) 28.69 (s, 1 C) 34.16 (s, 1 C) 36.57 (s, 1 C) 40.06 (s, 1 C) 44.55 (s, 1 C) 53.36 (s, 1 C) 128.56 (s, 1 C) 130.31 (s, 1 C) 131.18 (s, 1 C) 131.41 (s, 1 C) 133.07 (s, 1 C) 136.75 (s, 1 C). MS (M+1) 256.0, HPLC Purity 99% (AUC).

L. Synthesis of N,N-dimethyl-1-(3,4-dichlorophenyl)bicyclo[3.1.0]hexan-2-amine hydrochloride

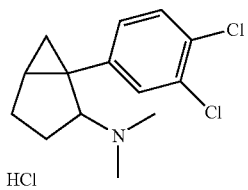

A mixture of 1-(3,4-dichlorophenyl)bicyclo[3.1.0]hexan-2-one (170 mg, 0.70 mmol) in dichloromethane (6 mL) was cooled to 0° C. and dimethylamine (2M solution in THF, 1.1 mL, 2.2 mmol) and TiCl$_4$ (66 mg; 0.35 mmol; 0.5 eq) were added sequentially. After stirring at 0° C. for 45 min, the mixture was warmed to reflux and was stirred overnight. The reaction was then treated with sodium triacetoxyborohydride (339 mg, 1.6 mmol) at room temperature. The reaction mixture was stirred for 5 h, and then the reaction mixture was quenched with water (10 mL). The layers were filtered, and the pH was adjusted to 9 using saturated NaHCO$_3$. The layers were then separated, and the aqueous layer was re-extracted with CH$_2$Cl$_2$ (2×), dried over sodium sulfate, filtered and concentrated in vacuo. The oily crude residue was converted to HCl salt using HCl/diethyl ether to provide the title compound as a beige solid (81 mg; 38%). $^1$H NMR (400 MHz, CHLOROFORM-d) δ ppm 1.36-1.42 (m, 1 H) 1.51-1.59 (t, 1H) 1.91-2.20 (m, 4H) 2.22-2.34 (m, 1H) 2.62 (d, 3H) 2.74 (d, 3H) 4.03-4.13 (m, 1H) 7.15 (d, 1 H) 7.37-7.46 (m, 2 H) 12.07-12.28 (bs, 1 H). $^{13}$C NMR (100 MHz, CHLOROFORM-d) d ppm 12.10 (s, 1 C) 25.73 (s, 1 C) 26.34 (s, 1 C) 31.69 (s, 1 C) 32.70 (s, 1 C) 43.47 (s, 1 C) 44.49 (s, 1 C) 74.93 (s, 1 C) 127.47 (s, 1 C) 130.12 (s, 1 C) 131.31 (s, 1 C) 131.47 (s, 1C) 133.44 (s, 1 C) 142.35 (s, 1 C). MS (M+1) 270.1, HPLC Purity 99% (AUC).

EXAMPLE IV

Preparation of 5-(3,4-dichlorophenyl)bicyclo[3.1.0]hexan-2-amines Using Reaction Scheme 3

A. Synthesis of 3-(3,4-dichlorophenyl)cyclopent-2-en-1-one

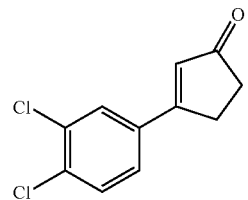

A solution of 1,2-dichloro-4-iodobenzene (1.0 g, 3.66 mmol) in THF (50 mL) at −78° C. was treated with a solution of n-butyllithium (2.5 M in hexanes; 1.5 mL, 3.8 mmol) such that the reaction temperature remained ≦−78° C. After 15 min, a solution of 3-methoxy-2-cyclopenten-1-one (0.452 g, 3.96 mmol) in THF (20 mL) was added such that the reaction temperature remained ≦−78° C. The reaction mixture was warmed to −20° C. over 2 h, quenched with a solution of 1N HCl and concentrated in vacuo to remove THF. A solution of 1N HCl (5 mL) was added, the solution was stirred for 30 min and extracted with EtOAc (2×). The combined organic extracts were washed with saturated aqueous NaHCO$_3$, brine, dried over MgSO$_4$, filtered and concentrated in vacuo. The residue was purified by silica gel chromatography using EtOAc/Heptanes as the eluting solvent to afford 0.3 g of target compound as a white powder (Yield 36%). $^1$H NMR (400 MHz, CHLOROFORM-d) δ ppm 2.58-2.62 (m, 2 H) 2.97-3.03 (m, 2 H) 6.56 (t, 1 H) 7.45-7.55 (m, 2 H) 7.71 (d, 1 H).

B. Synthesis of 3-(3,4-dichlorophenyl)cyclopent-2-en-1-ol

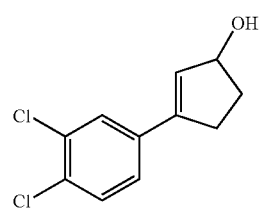

A solution of 3-(3,4-dichlorophenyl)cyclopent-2-en-1-one (2 g, 8.8 mmol) in methanol (40 mL) at 0° C. was treated with CeCl$_3$ 7H$_2$O (4.26 g, 11.4 mmol) followed portionwise by NaBH$_4$ (0.43 g, 11.4 mmol). The reaction was warmed to room temperature. The reaction mixture was stirred for 4 h, then quenched with saturated aqueous NH$_4$Cl and concentrated to remove methanol. The concentrate was diluted with H$_2$O and extracted with EtOAc (3×). The combined organic extracts were washed with brine, dried over MgSO$_4$, filtered, concentrated in vacuo and purified by silica gel chromatography using CH$_2$Cl$_2$/Methanol as the eluting solvent to afford 2 g (Yield 99%) of the target compound. $^1$H NMR (400 MHz, CHLOROFORM-d) δ ppm 1.82-1.92 (m, 1 H) 2.40-2.52 (m, 1 H) 2.54-2.65 (m, 1 H) 2.79-2.91 (m, 1 H) 4.96-5.04 (m, 1 H) 6.20-6.26 (m, 1 H) 7.27-7.31 (m, 1 H) 7.37-7.42 (m, 1 H) 7.51 (d, 1 H).

C. Synthesis of 5-(3,4-dichlorophenyl)bicyclo[3.1.0]hexan-2-ol

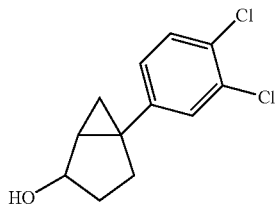

To an Et$_2$Zn solution (1.0M in hexane; 14 mL, 14 mmol) cooled to 0° C., a solution of CH$_2$I$_2$ (1.13 mL, 14 mmol) in CH$_2$Cl$_2$ (10 mL) was added. This was stirred for 5 min, then a solution of 3-(3,4-dichlorophenyl)cyclopent-2-en-1-ol (0.5 g, 2.19 mmol) in CH$_2$Cl$_2$ (50 mL) was added dropwise. The reaction mixture was stirred overnight then quenched with saturated aqueous NH$_4$Cl. The reaction mixture was extracted with CH$_2$Cl$_2$ (3×). The combined organic phases were dried over MgSO$_4$ and concentrated in vacuo. Purification of the crude material by silica gel chromatography using 10-30% EtOAc/Heptane as the eluting solvent gave the target compound (0.3 g, 64%). $^1$H NMR (400 MHz, CHLOROFORM-d) δ ppm 0.76-0.85 (m, 1 H) 1.20-1.33 (m, 2 H) 1.65-1.77 (broad, 1 H) 1.83-1.90 (m, 1 H) 1.93-2.17 (m, 3 H) 4.64-4.73 (m, 1 H) 6.93-6.97 (m, 1 H) 7.22 (d, 1 H) 7.29-7.34 (m, 1 H).

D. Synthesis of 5-(3,4-dichlorophenyl)bicyclo[3.1.0]hexan-2-one

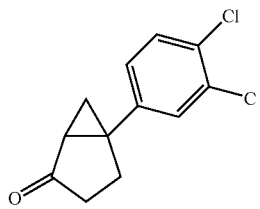

A solution of 5-(3,4-dichlorophenyl)bicyclo[3.1.0]hexan-2-ol (455 mg, 1.88 mmol) in CH$_2$Cl$_2$ (10 mL) at 0° C. was treated with pyridine (0.38 mL, 4.6 mmol), followed by Dess-Martin periodinane (1.95 g, 4.6 mmol) and warmed to ambient temperature. After 2 h, 3 drops of H$_2$O were added. After 0.5 h, the reaction was quenched with saturated NaHCO$_3$, saturated Na$_2$SO$_3$ and extracted with CH$_2$Cl$_2$ (3×). The combined organic extracts were dried and concentrated in vacuo. Purification by silica gel chromatography gave the target compound (200 mg, 44%). $^1$H NMR (400 MHz, CHLOROFORM-d) δ ppm 1.45-1.50 (m, 1 H) 1.51-1.58 (m, 1 H) 2.11 (dd, 1 H) 2.21-2.37 (m, 3 H) 2.37-2.45 (m, 1 H) 7.04 (dd, 1H) 7.32 (d, 1 H) 7.37 (d, 1 H).

E. Synthesis of 5-(3,4-dichlorophenyl)bicyclo[3.1.0]hexan-2-amine hydrochloride

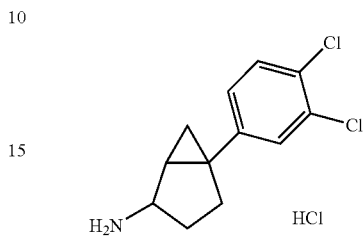

To a solution of 5-(3,4-dichlorophenyl)bicyclo[3.1.0] hexan-2-one (100 mg, 0.41 mmol) and anhydrous NaOAc (84 mg, 1.03 mmol) in anhydrous MeOH (5 mL) was added with stirring NH$_2$OH.HCl (152.9 mg, 2.2 mmol). The resulting mixture was stirred at room temperature for 18 h. The reaction mixture was filtered and the filtrate was concentrated in vacuo. The residue, dioxime [IS THIS CORRECT?] was reconstituted in anhydrous MeOH (5 ml) and added to a suspension of anhydrous NiCl$_2$ (116.94 mg, 0.9 mmol) in 5 ml of anhydrous MeOH with stirring. The reaction mixture was cooled to −30° C. and NaBH$_4$ (340.5 mg, 9 mmol) was added in small portions. After completion of the addition the mixture was allowed to warm to room temperature and concentrated in vacuo. This was then basified with aqueous solution of NaOH and extracted with CH$_2$Cl$_2$ (3×). Organic phases were concentrated and the crude was purified by prep. HPLC. The oily product (mixture of isomers) was converted to HCl salt (50 mg, 50.4%). $^1$H NMR (500 MHz, DMSO-d$_6$) δ ppm 0.79-0.95 (m, 2 H) 1.18-1.34 (m, 2 H) 1.38-1.45 (m, 1 H) 1.65-1.81 (m, 1 H) 1.83-1.92 (m, 1 H) 1.95-2.05 (m, 1 H) 6.32 (s, 2 H) 7.11-7.22 (m, 1 H) 7.23-7.38 (m, 2 H) 8.50 (broad, 1 H). $^{13}$C NMR (500 MHz, DMSO-d$_6$) δ ppm 13.85 (s, 1 C) 14.52 (s, 1 C) 16.03 (s, 1 C) 18.45 (s, 1 C) 22.38 (s, 1 C) 23.24 (s, 1 C) 25.02 (s, 1 C) 26.22 (s, 1 C) 26.22 (s, 1 C) 27.48 (s, 1 C) 28.31 (s, 1 C) 28.51 (s, 1 C) 29.79 (s, 1 C) 29.89 (s, 1 C) 31.39 (s, 1 C) 31.99 (s, 1 C) 51.62 (s, 1 C) 52.72 (s, 1 C) 55.87 (s, 1 C) 127.88 (s, 1 C) 127.95 (s, 1 C) 128.06 (s, 1 C) 128.38 (s, 1 C) 128.60 (s, 1C) 130.15 (s, 1 C) 130.24 (s, 1 C) 131.54 (s, 1 C) 131.70 (s, 1 C) 142.26 (s, 1 C) 142.44 (s, 1 C). MS (M+1) 242.1.

F. Synthesis of N-methyl-5-(3,4-dichlorophenyl) bicyclo[3.1.0]hexan-2-amine hydrochloride

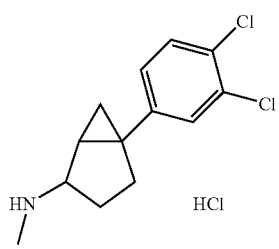

A solution of ketone 5-(3,4-dichlorophenyl)bicyclo[3.1.0]hexan-2-one (100 mg, 0.41 mmol) was treated with a solution of methylamine (33% in absolute ethanol, 30 ml) followed by the addition of titanium (IV) isopropoxide (233 mg, 0.82 mmol). The reaction mixture was stirred for 5 h, and then sodium borohydride (31 mg, 0.82 mmol) was added. After 1 h the reaction mixture was concentrated, aqueous solutions of sodium bicarbonate and sodium sulfate were added and this was extracted with $CH_2Cl_2$ (3×), dried over $K_2CO_3$, filtered and concentrated in vacuo. The oily crude residue was converted to HCl salt (113 mg, 75%). $^1$H NMR (400 MHz, DMSO-$d_6$) δ ppm 0.89-0.97 (m, 1 H) 1.34-1.50 (m, 2 H) 1.93-2.09 (m, 3 H) 2.09-2.19 (m, 1 H) 2.28-2.36 (m, 3 H) 3.25-3.35 (m, 1 H) 3.76-3.85 (m, 1 H) 7.17 (dd, 1H) 7.42 (d, 1 H) 7.52 (d, 1 H) 7.90-8.42 (broad, 1 H). $^{13}$C NMR (400 MHz, DMSO-$d_6$) d ppm 15.14 (s, 1 C) 23.58 (s, 1 C) 24.06 (s, 1 C) 26.17 (s, 1 C) 29.51 (s, 1 C) 31.23 (s, 1 C) 31.36 (s, 1 C) 59.81 (s, 1C) 126.56 (s, 1 C) 128.16 (s, 1 C) 128.28 (s, 1 C) 130.24 (s, 1 C) 130.90 (s, 1 C) 144.68 (s, 1 C). MS (M+1) 256.0.

G. Synthesis of N,N-dimethyl-5-(3,4-dichlorophenyl)bicyclo[3.1.0]hexan-2-amine hydrochloride

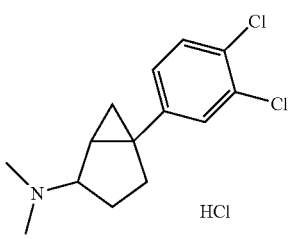

The mixture of 5-(3,4-dichlorophenyl)bicyclo[3.1.0]hexan-2-one (110 mg, 0.45 mmol) in DCE (3 mL) and dimethylamine (2M solution in THF, 5 mL, 4.5 mmol) was treated with sodium triacetoxyborohydride (95 mg, 0.45 mmol) at room temperature. The reaction mixture was stirred for 0.5 h, then the reaction mixture was diluted with saturated $NaHCO_3$, extracted with $CH_2Cl_2$(3×), dried over $K_2CO_3$, filtered and concentrated in vacuo to afford the target compound. The oily crude residue (96 mg, 79%) was converted to HCl salt. $^1$H NMR (400 MHz, CHLOROFORM-d) δ ppm 1.11 (t, 1 H) 1.77-1.87 (m, 1 H) 1.96-2.02 (m, 1 H) 2.03-2.22 (m, 3 H) 2.25-2.37 (m, 1 H) 2.81 (d, 3 H) 2.92 (d, 3 H) 3.72-3.90 (m, 1 H) 6.96 (dd, 7 H) 7.21 (d, 7 H) 7.33 (d, 7 H) 12.07-12.30 (broad, 1 H), $^{13}$C NMR (126 MHz, CHLOROFORM-d) δ ppm 15.96 (s, 1 C) 24.22 (s, 1 C) 25.84 (s, 1 C) 31.02 (s, 1 C) 33.20 (s, 1 C) 42.65 (s, 1 C) 42.69 (s, 1 C) 69.75 (s, 1 C) 125.96 (s, 1 C) 128.61 (s, 1 C) 130.52 (s, 1 C) 130.57 (s, 1 C) 132.58 (s, 1C) 142.82 (s, 1 C). $^{13}$C NMR (400 MHz, CHLOROFORM-d) d ppm 15.96 (s, 1 C) 24.22 (s, 1 C) 25.84 (s, 1 C) 31.02 (s, 1 C) 33.20 (s, 1 C) 42.65 (s, 1 C) 42.69 (s, 1 C) 69.75 (s, 1 C) 125.96 (s, 1 C) 128.61 (s, 1 C) 130.52 (s, 1 C) 130.57 (s, 1 C) 132.58 (s, 1C) 142.82 (s, 1 C). MS (M+1) 270.

EXAMPLE V

Preparation of 1-(naphthalene-1-yl)-bicyclo[3.1.0]hexan-3-amines Using Reaction Scheme 3

A. Synthesis of 3-naphthalen-1-yl-prop-2-yn-1-ol

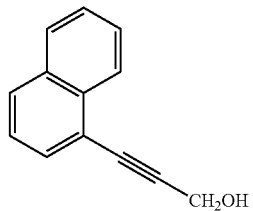

To a stirred solution of de-gassed 1-iodonaphthalene (10.00 g, 39.36 mmol), propargyl alcohol (2.25 g, 40.15 mmol, 1.02 eq.), triethylamine (7.97 g, 78.72 mmol, 2 eq.) and copper iodide (0.02 g, 0.12 mmol, 0.3 mol %) in tetrahydrofuran (30 mL) was added bis(triphenylphosphine)palladium(II) chloride (0.05 g, 0.07 mmol, 0.18 mol %). The mixture was stirred at 35° C. under an atmosphere of nitrogen for 19 h. The mixture was concentrated in vacuo to afford a black tar residue. The residue was purified by flash chromatography ($SiO_2$, ethyl acetate:petroleum ether 40-60; 30%: 70%) to afford the desired compound as a yellow oil (3.51 g, 49%). $^1$H NMR (400 MHz, $CDCl_3$) δ ppm 4.64 (2H, s, $CH_2$), 7.38-7.40 (3H, m, ArH), 7.64 (1H, m, ArH), 7.79 (1H, d, J=8.0 Hz, ArH), 7.81 (1H, d, J 8.0 Hz, ArH), 8.32 (1H, d, J 8.0 Hz, ArH).

B. Synthesis of naphthalen-1-yl-propynal

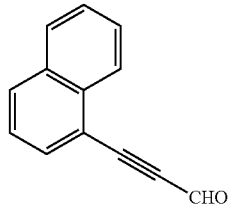

A solution of 3-naphthalen-1-yl-prop-2-yn-1-ol (3.51 g, 19.26 mmol) in dichloromethane (60 mL) and tetrapropylammonium perruthenate (0.14 g, 0.39 mmol, 2 mol %) was stirred at 0° C. under an atmosphere of nitrogen. N-methyl-morpholin-N-oxide (4.06 g, 34.67 mmol, 1.8 eq.) was divided into 4 portions and the first portion (1.01 g, 8.67 mmol) was added to the reaction mixture and the resulting black mixture was stirred at room temperature for an hour. The remaining portions were added sequentially at hourly intervals and the mixture was left to stir for a further 19 hours. The TLC of the reaction mixture indicated that the starting material had been consumed and the reaction was quenched by the addition of saturated aqueous sodium bicarbonate (50 mL) and the reaction mixture was extracted with dichloromethane (3×50 mL), dried over sodium sulphate and concentrated in vacuo to afford a black residue. The crude material was purified by flash chromatography (SiO₂, ethyl acetate:petroleum ether 40-60; 30%:70%) to afford the desired compound as a yellow oil (2.85 g, 82%). ¹H NMR (400 MHz, CDCl₃) δ ppm 7.49-7.65 (4H, m, ArH), 7.89 (1H, d, J 8.0 Hz, ArH), 7.99-8.01 (1H, d, J 8.0 Hz, ArH), 8.32-8.34 (1H, d, J 8.4 Hz, ArH), 9.57 (1H, s, CHO).

C. Synthesis of 1-naphthalen-1-yl-hex-5-en-1-yn-3-ol

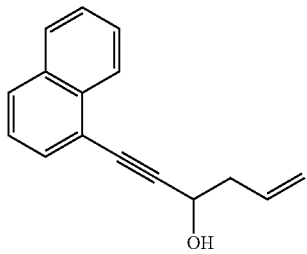

A solution of naphthalen-1-yl-propynal (2.50 g, 13.88 mmol) in tetrahydrofuran (50 mL) was added to a stirred solution of allylmagnesium bromide (1M in diethyl ether, 20.81 mL, 20.81 mmol, 1.5 eq.) at 0° C. over 0.5 h under an atmosphere of nitrogen. Stirring was continued for a further 2 h at 0° C. The reaction was quenched with water (50 mL) at 0° C. To the reaction mixture was added diethyl ether (100 mL) and the reaction mixture was stirred and allowed to separate. The aqueous phase was re-extracted with diethyl ether (3×100 mL) and the combined organic layers were dried over sodium sulphate and concentrated in vacuo to afford a yellow oil. The crude material was purified by flash chromatography (SiO₂, ethyl acetate:petroleum ether 40-60; 30%:70%) to afford the desired compound as a yellow oil (2.34 g, 76%). ¹H NMR (400 MHz, CDCl₃) δ ppm 2.67-2.69 (2H, m, CH₂), 4.80-4.81 (1H, m, CH), 5.24-5.31 (2H, m, CH₂), 5.99-6.06 (1H, m, CH), 7.40-7.64 (4H, m, Ar—H), 7.66 (1H, d, J 8.0 Hz, ArH), 7.82 (1H, d, J 8.0 Hz, ArH), 8.28 (1H, d, J 8.0 Hz, ArH).

D. Synthesis of 1-naphthalen-1-yl-bicyclo[3.1.0]hexan-3-one

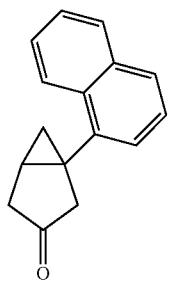

To a stirred solution of 1-naphthalen-1-yl-hex-5-en-1-yn-3-ol (1.00 g, 4.50 mmol) under an atmosphere of nitrogen in toluene (100 mL) was added platinum chloride (0.06 g, 0.22 mmol, 5 mol %); the resulting black mixture was stirred at 80° C. for 24 hr. TLC indicated that the reaction was complete. The organics were concentrated in vacuo to afford a black residue. The crude material was purified by flash chromatography (SiO₂, ethyl acetate:petroleum ether 40-60; 10%:90%) to afford the desired compound as a yellow oil (0.57 g, 57%). ¹H NMR (400 MHz, CDCl₃) δ ppm 0.73 (1H, t, J 4.0 Hz, CH), 0.82-0.84 (1H, m, CH), 1.17-1.24 (1H, m, CH), 2.47 (1H, d, J 19.0 Hz, CH), 2.75 (2H, d, J 10 Hz, CH)), 2.95-3.09 (1H, m, CH), 7.38-7.51 (4H, m, ArH), 7.73 (1H, d, J 8.0 Hz, ArH), 7.84 (1H, d, J 8.0 Hz, ArH), 8.10 (1H, d, J 8.0 Hz, ArH).

E. Synthesis of methyl-(1-naphthalen-1-yl-bicyclo[3.1.0]hex-3-yl)-amine hydrochloride

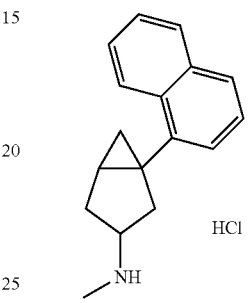

To a stirred solution of the ketone 1-naphthalen-1-yl-bicyclo[3.1.0]hexan-3-one (0.25 g, 1.12 mmol) in methanol (10 mL) was added methylamine (33% in ethanol; 3 mL) and sodium cyanoborohydride (0.09 g, 1.46 mmol, 1.3 eq.). The mixture was left to stir for 19 h at room temperature under an atmosphere of nitrogen. The reaction mixture was then cooled to 10° C. and acidified with 1N HCl (10 mL). The organics were concentrated in vacuo and the resulting aqueous layer was further diluted with water (10 mL). The aqueous layer was extracted with ethyl acetate (1×20 mL) and the yellow non-polar impurities were removed. The pH of the aqueous layer was subsequently adjusted to pH 9 with 1N NaOH and then the aqueous layer was extracted with ethyl acetate (5×20 mL) followed by dichloromethane (3×20 mL). The combined organic layers were dried over magnesium sulphate and concentrated in vacuo to afford an oily residue. The oil was dissolved in diethyl ether (10 mL) and the HCl salt was formed by slowly adding HCl (1M in diethyl ether, 1 mL). The slurry was stirred for 0.5 h before filtration. The solid pale brown solid was rinsed with ice-cold diethyl ether (10 mL) and the compound was transferred to a vacuum oven for drying for 12 h to afford the desired compound as a mixture of diastereoisomers as a beige solid (0.05 g, 16%). ¹H NMR (400 MHz, CD₃OD) δ ppm 0.85-0.92 (2H, m, 2×CH), 1.14-1.31 (4H, m, 4×CH), 1.82-1.95 (2H, m, CH₂), 2.05-2.13 (1H, m, CH), 2.31-2.36 (2H, m, CH₂), 2.49-2.54 (2H, m, CH₂), 2.62 (3H, s, CH₃), 2.68 (3H, s, CH₃), 2.88-2.96 (1H, m, CH), 3.45-3.53 (1H, m, CH), 4.00-4.07 (1H, m, CH), 7.36-7.55 (8H, m, ArH), 7.73 (2H, d, J 7.6 Hz, ArH), 7.84 (2H, d, J 8.0 Hz, ArH), 8.22 (1H, d, J 8.0 Hz, ArH), 8.28 (1H, d, J 8.4 Hz, ArH). ¹³C NMR (400 MHz, CD₃OD) δ ppm 14.49 (s, 1C), 22.15 (s, 1C), 24.04 (s, 1C), 24.75 (s, 1C), 30.13 (s, 1C), 31.20 (s, 1C), 31.46 (s, 1C), 31.70 (s, 1C), 32.83 (s, 1C), 33.48 (s, 1C), 37.86 (s, 1C), 40.42 (s, 1C), 56.93 (s, 1C), 63.10 (s, 1C), 124.45 (s, 1C), 125.23 (s, 1C), 125.31 (s, 1C), 125.43 (s, 1C), 125.47 (s, 1C), 125.74 (s, 1C), 125.78 (s, 1C), 127.38 (s, 1C), 127.44 (s, 1C), 128.50 (s, 1C), 132.61 (s, 1C), 134.14 (s, 1C), 134.20 (s, 1C), 138.83 (s, 1C), 139.39 (s, 1C). LCMS (M+1) 238.

F. Synthesis of dimethyl-(1-naphthalen-1-yl-bicyclo[3.1.0]hex-3-yl)amine hydrochloride

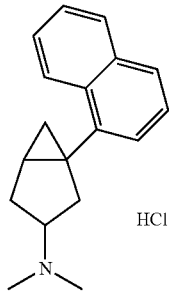

To a stirred solution of the ketone 1-naphthalen-1-yl-bicyclo[3.1.0]hexan-3-one (0.25 g, 1.12 mmol) in methanol (10 mL) was added dimethylamine (2M in tetrahydrofuran; 2.25 mL, 4.50 mmol, 4 eq.) and sodium cyanoborohydride (0.09 g, 1.46 mmol, 1.3 eq.). The mixture was left to stir for 19 h at room temperature under an atmosphere of nitrogen. The reaction mixture was then cooled to 10° C. and acidified with 1N HCl (10 mL). The organics were concentrated in vacuo and the resulting aqueous layer was further diluted with water (10 mL). The aqueous layer was extracted with ethyl acetate (20 mL) and the yellow non-polar impurities were removed. The pH of the aqueous layer was subsequently adjusted to pH 9 with 1N NaOH and then the aqueous layer was extracted with ethyl acetate (5×20 mL) followed by dichloromethane (3×20 mL). The combined organic layers were dried over magnesium sulphate and concentrated in vacuo to afford an oily residue. The oil was dissolved in diethyl ether (10 mL) and the HCl salt was formed by slowly adding HCl (1M in diethyl ether, 1 mL). The slurry was stirred for 0.5 h before filtration. The solid pale brown solid was rinsed with ice cold diethyl ether (10 mL) and the compound was transferred to a vacuum oven for drying for 12 h to afford the desired compound as a mixture of diastereoisomers as a beige solid (0.051 g, 16%). $^1$H NMR (400 MHz, CD$_3$OD) δ ppm 0.88-0.92 (1H, m, CH), 1.01-1.03 (1H, m, CH), 1.14-1.15 (1H, m, CH), 1.18-1.21 (1H, m, CH), 1.27-1.30 (1H, m, CH), 1.83-1.90 (2H, m, 2×CH), 1.98-1.99 (1H, m, CH), 2.15-2.21 (1H, m, CH), 2.30-2.56 (4H, m, 2×CH$_2$), 2.82 (3H, s, CH$_3$), 2.84 (3H, s, CH$_3$), 2.89 (3H, s, CH$_3$), 2.93 (3H, s, CH$_3$), 3.53-3.56 (1H, m, CH), 4.15-4.19 (1H, m, CH), 7.37-7.57 (8H, m, ArH), 7.76-7.80 (2H, m, ArH), 7.88 (2H, d, J 8.4 Hz, ArH), 8.25-8.28 (2H, m, ArH). $^{13}$C NMR (400 MHz, CD$_3$OD) δ ppm 14.08 (s, 1C), 22.11 (s, 1C), 22.75 (s, 1C), 31.09 (s, 1C), 33.11 (s, 1C), 37.53 (s, 1C), 40.19 (s, 1C), 41.85 (s, 1C), 65.05 (s, 1C), 124.28 (s, 1C), 125.46 (s, 1C), 125.15 (s, 1C), 125.29 (s, 1C), 125.45 (s, 1C), 125.53 (s, 1C), 125.76 (s, 1C), 125.82 (s, 1C), 127.44 (s, 1C), 127.56 (s, 1C), 128.47 (s, 1C), 128.56 (s, 1C), 134.14 (s, 1C), 134.20 (s, 1C), 138.83 (s, 1C), 139.39 (s, 1C). LCMS (M+1) 252.

EXAMPLE VI

Preparation of 5-(naphthalene-1-yl)bicyclo[3.1.0]hexan-2-amines Using Reaction Scheme 3

A. Synthesis of 3-naphthalen-1-yl-cyclopent-2-enone

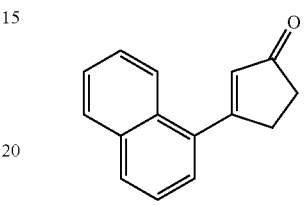

To a stirred solution of 1-iodonapthalene (10.00 g, 39.36 mmol) in tetrahydrofuran (300 mL) at −78° C. was added n-butyllithium (2.5 M in hexanes; 17.49 mL, 43.73 mmol, 1.1 eq.) so that the reaction temperature remained ≦−78° C. The reaction mixture was stirred for 15 minutes. To the reaction mixture was added a solution of 3-methoxy-2-cyclopenten-1-one (5.10 g, 45.48 mmol, 1.16 eq.) in tetrahydrofuran (50 mL) so that the reaction temperature remained ≦−78° C. The reaction mixture was warmed to −20° C. over a 2 h period and the reaction mixture was quenched with a solution of 1N HCl and concentrated in vacuo to remove the organics. A solution of 1N HCl was added and the reaction mixture was stirred for a further 0.5 h and extracted with ethyl acetate (3×100 mL). The organic layers were combined, washed with saturated aqueous sodium bicarbonate (100 mL) followed by brine (100 mL), dried over magnesium sulphate and concentrated in vacuo to afford a yellow oil. The crude oil was purified by flash chromatography (SiO$_2$, ethyl acetate:petroleum ether 40-60; 20%:80%) to afford the desired compound as an off-white solid (4.01 g, 49%). $^1$H NMR (400 MHz, CDCl$_3$) δ ppm 2.68 (2H, dt, J 2, 4.8 Hz, CH$_2$), 3.16 (2H, td, J 2.4, 4.8 Hz, CH$_2$), 6.51 (1H, t, J 1.6 Hz, CH), 7.54-7.60 (4H, m, ArH), 7.93-8.01 (2H, m, ArH), 8.10-8.18 (1H, m, ArH).

B. Synthesis of 3-naphthalen-1-yl-cyclopent-2-enol

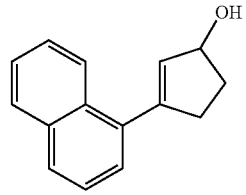

To a stirred solution of 3-napthalen-1-yl-cyclopent-2-enone (3.36 g, 16.13 mmol) in ethanol (150 mL) was added cerium trichloride (3.98 g, 16.13 mmol) followed portionwise by sodium borohydride (0.73 g, 19.36 mmol, 1.2 eq.) at room temperature. The reaction mixture was stirred for 0.5 h, until the reaction was shown to be complete by TLC. The reaction was quenched by the addition of saturated aqueous ammonium chloride (100 mL) and the organics were removed in vacuo. The remaining aqueous layer was further diluted with water (100 mL) and extracted with dichloromethane (3×200 mL). The organic extracts were combined, dried over magnesium sulphate and concentrated in vacuo. The crude oil was purified by flash chromatography (SiO$_2$, ethyl acetate:petroleum ether 40-60; 20%:80%) to afford the desired compound as a yellow oil (2.49 g, 74%). $^1$H NMR (400 MHz, CDCl$_3$) δ ppm 2.01-2.04 (1H, m, CH), 2.44-2.45 (1H, m, CH), 2.77-2.78 (1H, m, CH), 2.93-2.95 (1H, m, CH), 3.60 (1H, q, J 1.3 Hz, CH), 6.07 (1H, q, J 1.3 Hz, CH), 7.24-7.35 (4H, m, ArH), 7.75 (1H, d, J 8.0 Hz, ArH), 7.78 (1H, d, J 8.0 Hz, ArH), 8.15 (1H, d, J 8.0 Hz, ArH).

C. Synthesis of 5-naphthalen-1-yl-bicyclo[3.1.0]hexan-2-ol

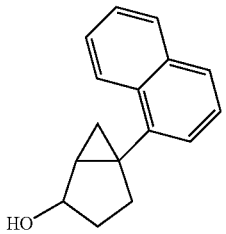

To a stirred solution of 3-naphthalen-1-yl-cyclopent-2-enol (1.00 g, 4.79 mmol) in dichloromethane (60 mL) was added diethylzinc (1.0 M in hexanes; 23.6 mL, 23.62 mmol, 4.9 eq.) and the reaction mixture was stirred for 10 min. The reaction mixture was cooled to 0° C. and treated with a solution of diiodomethane (1.93 mL, 24.04 mmol, 5 eq.) in dichloromethane (10 mL) in a dropwise fashion over 10 min. The reaction mixture was subsequently allowed to warm to ambient temperature and stirred for a further 2 h. TLC indicated that the reaction had gone to completion and was quenched with saturated aqueous ammonium chloride (50 mL). The reaction mixture was extracted with dichloromethane (3×100 mL) and the combined organics were dried over magnesium sulphate and concentrated in vacuo to afford the desired compound as a yellow oil. The crude material was purified by flash chromatography (SiO$_2$, ethyl acetate:petroleum ether. 40-60; 20%:80%) to afford the desired compound as a yellow oil (1.00 g, 93%). $^1$H NMR (400 MHz, CDCl$_3$) δ ppm 0.92-0.99 (1H, m, CH), 1.43-1.44 (2H, m, CH$_2$), 1.82-1.86 (1H, m, CH), 1.93-2.07 (2H, m, CH$_2$), 2.15-2.23 (1H, m, CH), 5.02-5.04 (1H, m, CH), 7.24-7.35 (4H, m, ArH), 7.75 (1H, d, J 8.0 ArH), 7.87 (1H, d, J 8.0 Hz, ArH) 8.15 (1H, d, J 8.4 Hz, ArH).

D. Synthesis of 5-naphthalen-1-yl-bicyclo[3.1.0]hexan-2-one

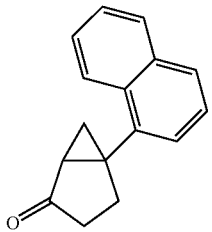

To a stirred solution of 5-naphthalen-1-yl-bicyclo[3.1.0]hexan-2-ol (1.00 g, 4.46 mmol) in dichloromethane (40 mL) was added pyridine (0.50 mL, 6.24 mmol, 1.4 eq.) followed by Dess-Martin periodinane (2.27 g, 5.35 mmol, 1.2 eq.) and the reaction mixture was warmed to room temperature and stirred for 3 h. To the reaction mixture was added 3 drops of water and the reaction mixture was left to stir for a further 0.5 h. The reaction mixture was quenched with saturated aqueous sodium bicarbonate (100 mL) followed by saturated aqueous sodium sulphite (100 mL) and extracted with dichloromethane (3×200 mL). The combined organic layers were dried over magnesium sulphate and concentrated in vacuo to afford the desired compound as a yellow oil. The crude material was purified by flash chromatography (SiO$_2$, ethyl acetate:petroleum ether 40-60; 30%:70%) to afford the desired compound as a yellow oil (0.71 g, 72%). $^1$H NMR (400 MHz, CDCl$_3$) δ ppm 1.59-1.61 (1H, m, CH), 1.68-1.70 (2H, m, CH$_2$), 2.21-2.23 (1H, m, CH), 2.24-2.40 (3H, m, CH and CH$_2$), 7.44-7.54 (4H, m, ArH), 7.79 (1H, d, J 8.0 Hz, ArH), 7.88 (1H, d, J 8.0 Hz, ArH), 8.17 (1H, d, J 8.0 Hz, ArH).

E. Synthesis of methyl-(5-naphthalen-1-yl-bicyclo[3.1.0]hex-2-yl)-amine hydrochloride

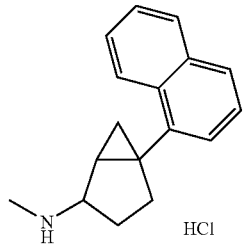

5-Naphthalen-1-yl-bicyclo[3.1.0]hexan-2-one (0.28 g, 1.28 mmol) was treated with a solution of methylamine (33% in absolute ethanol, 50 mL) followed by the addition of titanium (IV) isopropoxide (0.76 mL, 2.56 mmol, 2 eq.). The resulting mixture was stirred for 19 h before the addition of sodium borohydride (0.10 g, 2.56 mmol, 2 eq.). The reaction mixture was stirred for 1 h and concentrated in vacuo to afford a residue. The resulting residue was diluted with aqueous solutions of sodium bicarbonate (50 mL) and sodium sulphate (50 mL) and extracted with dichloromethane (3×100 mL). The combined organics were dried over potassium carbonate, filtered and concentrated in vacuo to afford a brown oily residue. The oil was dissolved in diethyl ether (10 mL) and the HCl salt was formed by slowly adding HCl (1M in diethyl ether, 1 mL). The slurry was stirred for 0.5 h before filtration. The solid pale brown solid was rinsed with diethyl ether and the compound was transferred to a vacuum oven for drying for 12 h to afford the desired compound as a beige solid (0.102 g, 30%). $^1$H NMR (400 MHz, CD$_3$OD) δ ppm 1.14-1.32 (3H, m, 3×CH), 1.87-1.95 (1H, m, CH), 1.96-2.09 (2H, m, CH$_2$), 2.18-2.29 (1H, m, CH), 2.61 (3H, s, CH$_3$), 3.77 (1H, m, CH), 7.37-7.53 (4H, m, ArH), 7.73 (1H, d, J 8.0 Hz, ArH), 7.86 (1H, d, J 8.0 Hz, ArH), 8.26-8.29 (1H, d, J 8.0 Hz, ArH). $^{13}$C NMR (400 MHz, CD$_3$OD); δ ppm 11.66 (s, 1C), 24.27 (s, 1C), 24.82 (s, 1C), 31.35 (s, 1C), 32.86 (s, 1C), 32.90 (s, 1C), 61.69 (s, 1C), 124.16 (s, 1C), 125.24 (s, 1C), 125.43 (s, 1C), 125.72 (s, 1C), 127.54 (s, 1C), 128.55 (s, 1C), 132.35 (s, 1C), 134.17 (s, 1C), 138.46 (s, 1C). LCMS (M+1) 238.

F. Synthesis of dimethyl-(5-naphthalen-1-yl-bicyclo[3.1.0]hex-2-yl)-amine hydrochloride

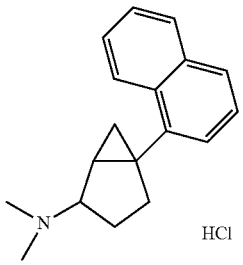

5-Naphthalen-1-yl-bicyclo[3.1.0]hexan-2-one (0.25 g, 1.13 mmol) in dichloroethane (10 mL) and dimethylamine (2M solution in tetrahydrofuran, 5.62 mL, 11.25 mmol, 10 eq.) was treated with sodium triacetoxyborohydride (0.24 g, 1.13 mmol) at room temperature. The reaction mixture was stirred for 19 h and concentrated to afford an oily residue. The resulting residue was diluted with saturated aqueous sodium bicarbonate (50 mL), extracted with dichloromethane (3×100 mL) and the combined organics were dried over potassium carbonate, filtered and concentrated in vacuo. The oil was dissolved in diethyl ether (10 mL) and the HCl salt was formed by slowly adding HCl (1M in diethyl ether, 1 mL). The slurry was stirred for 0.5 h before filtration. The solid pale brown solid was rinsed with diethyl ether and the compound was transferred to a vacuum oven for drying for 12 h to afford the desired compound as a brown solid. (0.074 g, 23%). $^1$H NMR (400 MHz, CD$_3$OD) δ ppm. 1.17-1.44 (3H, m, 3×CH), 1.76-1.83 (2H, m, CH$_2$), 1.94-2.06 (2H, m, CH$_2$), 2.40 (3H, s, CH$_3$), 2.42 (3H, s, CH$_3$), 3.09-3.14 (1H, m, CH), 7.37-7.57 (4H, m, Ar), 7.71 (1H, d, J 8.0 Hz, ArH), 7.85 (1H, d, J 8.0 Hz, ArH), 8.26-8.28 (1H, d, J 7.6 Hz, ArH). $^{13}$C NMR (400 MHz, CD$_3$OD); δ ppm 12.08 (s, 1C), 24.11 (s, 1C), 24.75 (s, 1C), 33.01 (s, 1C), 33.43 (s, 1C), 41.57 (s, 1C), 42.06 (s, 1C), 70.09 (s, 1C), 124.12 (s, 1C), 125.24 (s, 1C), 125.46 (s, 1C), 125.77 (s, 1C), 127.61 (s, 1C), 128.56 (s, 1C), 132.27 (s, 1C), 134.17 (s, 1C), 138.32 (s, 1C). LCMS (M+1) 252.

EXAMPLE VII

Preparation of 1-(naphthalene-2-yl)-bicyclo[3.1.0]hexan-3-amines Using Reaction Scheme 2

A. Synthesis of 3-naphthalen-2-yl-prop-2-yn-1-ol

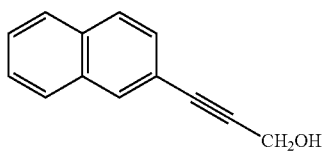

2-Bromonapthalene (50.0 g, 242.0 mmol), copper iodide (230.0 g, 1210.0 mmol, 5 eq.), potassium iodide (200 g, 1210.0 mmol, 5 eq.) and hexamethylphosphoramide (500 mL) were stirred and heated to 160° C. for 8 h. This was cooled and added to 1N HCl (250 mL) then toluene (300 mL) and ether (300 mL) and the mixture filtered through celite. The organic layer was separated and washed with water (2×250 mL) dried over magnesium sulphate and concentrated to afford 2-iodonaphthalene (61.5 g, 59%) as a white solid. $^1$H NMR (400 MHz, CDCl$_3$) δ ppm 7.46-7.52 (2H, m, ArH, 7.55-7.58 (1H, m, ArH), 7.68-7.74 (2H, m, ArH), 7.76-7.82 (1H, m, ArH), 8.22-8.26 (1H, m, ArH).

Bis(triphenylphosphine)palladium (II) chloride (0.18 g, 0.26 mmol, 0.18 mol %) was added to a stirred solution of propargyl alcohol (8.43 mL, 144.8 mmol, 1 eq.), 2-iodonapthalene (36 g, 142 mmol), triethylamine (39.6 mL, 284 mmol, 2 eq.) and copper iodide (0.09 g, 0.49 mmol, 0.3 mol %) in tetrahydrofuran (750 ml). The mixture was stirred at 35° C. for 12 h under nitrogen atmosphere. The mixture was then filtered through a bed of celite and the filtrate was washed with ethyl acetate (200 ml). The filtrate was then concentrated in vacuo. Purification by silica gel chromatography using 1:6 ethyl acetate/petrol as the eluting solvent afforded the desired compound (2.85 g, 11%) as a white solid. $^1$H NMR (400 MHz, CDCl$_3$) δ ppm 4.54 (2H, s, CH$_2$), 7.45-7.49 (3H, m, ArH), 7.75-7.81 (3H, m, ArH), 7.95 (1H, s, ArH).

B. Synthesis of naphthalen-2-yl-propynal

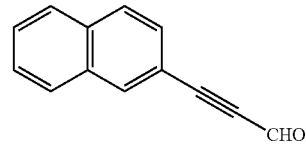

3-(Naphthalen-2-yl)prop-2-yn-1-ol (2.48 g, 13.6 mmol), tetrapropylammonium perruthanate (0.09 g, 0.27 mmol, 2 mol %), and dichloromethane (150 mL) were stirred under nitrogen at 0° C. A portion of N-methylmorpholine-N-oxide (2.87 g, 245 mmol) was added and the reaction was stirred at room temperature for 1 h. The remaining N-methylmorpholine-N-oxide was then added over 3 h at room temperature and the reaction stirred for a further 1 hour. Saturated sodium bicarbonate (75 mL) was added and the mixture was extracted with dichloromethane (3×75 mL), dried over sodium sulphate filtered and concentrated in vacuo to afford the desired compound (2.45 g, 81%) as a brown solid. $^1$H NMR (400 MHz, CDCl$_3$) δ ppm 7.47-7.54 (4H, m, ArH), 7.77-7.87 (3H, m, ArH), 8.19 (1H, s, ArH), 9.48 (1H, s, CHO).

C. Synthesis of 1-naphthalen-2-yl-hex-5-en-1-yn-3-ol

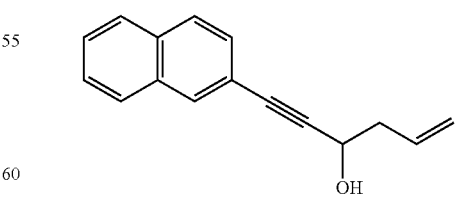

A solution of 3-(naphthalen-2-yl)propiolaldehyde (3.97 g, 22.0 mmol) in tetrahydrofuran (250 mL) was added to a solution of allyl magnesium bromide (33.1 mL, 33.0 mmol, 1.5 eq.) at 0° C. over 25 min. Stirring was continued overnight and the reaction was carefully quenched with water (50 mL)

at 0° C. tert-butyl methyl ether (100 mL) was added, and the layers were stirred and allowed to separate. The aqueous phase was re-extracted with tert-butyl methyl ether (50 mL) and the combined organic layers were dried over sodium sulphate and filtered. The filtrate was concentrated in vacuo. Purification by silica gel chromatography using 1:6 ethyl acetate/petrol as the eluting solvent to afford the desired compound (2.30 g, 47%) as a yellow oil. $^1$H NMR (400 MHz, CDCl$_3$) δ ppm 2.58-2.65 (2H, m, CH$_2$), 4.71 (1H, t, J=6.3 Hz, CH), 5.24-5.31 (2H, m, CH$_2$), 5.95-6.06 (1H, m, CH), 7.46-7.51 (3H, m, ArH), 7.76-7.83 (3H, m, ArH), 7.96 (1H, s, ArH).

D. Synthesis of 1-naphthalen-2-yl-bicyclo[3.1.0]hexan-3-one

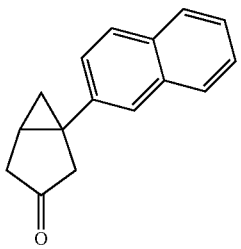

To a stirred solution of 1-naphthalen-2-yl-hex-5-en-1-yn-3-ol (1.00 g, 4.50 mmol) under an atmosphere of nitrogen in toluene (100 mL) was added platinum chloride (0.06 g, 0.22 mmol, 5 mol %); the resulting black mixture was stirred at 80° C. for 24 hr. TLC indicated that the reaction was complete. The organics were concentrated in vacuo to afford a black residue. The crude material was purified by flash chromatography (SiO$_2$, ethyl acetate:petroleum ether 40-60; 10%:90%) to afford the desired compound as a yellow oil (0.64 g, 64%). $^1$H NMR (400 MHz, CDCl$_3$) δ ppm 0.70 (1H, t, J 4.0 Hz, CH), 0.83-0.86 (1H, m, CH), 1.41-1.44 (1H, m, CH), 2.44 (1H, d, J 18.0 Hz, CH), 2.75 (1H, d, J 18 Hz, CH$_2$), 2.86-2.91 (1H, m, CH), 3.05 (1H, d, J 18.0 Hz, CH), 7.24-7.26 (1H, m, ArH), 7.44-7.49 (2H, m, ArH), 7.63 (1H, s, ArH), 7.80 (1H, d, J 8.0 Hz, ArH).

E. Synthesis of methyl-(1-naphthalen-2-yl-bicyclo[3.1.0]hex-3-yl)-amine

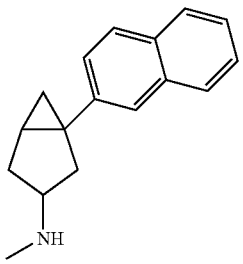

To a stirred solution of the ketone 1-naphthalen-2-yl-bicyclo[3.1.0]hexan-3-one (0.25 g, 1.12 mmol) in methanol (10 mL) was added methylamine (33% in ethanol; 3 mL) and sodium cycanoborohydride (0.09 g, 1.46 mmol, 1.3 eq.). The mixture was left to stir for 19 h at room temperature under an atmosphere of nitrogen. The reaction mixture was quenched by the addition of water (50 mL) and the organics were concentrated in vacuo. The aqueous layer was extracted with ethyl acetate (3×50 mL) and the combined organic layers were dried over magnesium sulphate and concentrated in vacuo to afford an oily residue. The residue was purified by flash chromatography (SiO$_2$, methanol:ethyl acetate:triethylamine; 10%:89%:1%) to afford the desired compound as a white solid (0.70 g, 23%). $^1$H NMR (400 MHz, CD$_3$OD) δ ppm 1.06-1.08 (1H, m, CH), 1.17-1.19 (1H, m, CH), 1.61-1.66 (1H, m, CH), 1.74-1.80 (1H, m, CH), 1.97-2.01 (1H, m, CH), 2.33-2.34 (3H, m, CH$_3$), 2.42-2.48 (1H, m, CH), 2.58-2.64 (1H, m, CH), 3.30-3.44 (1H, m, CH), 7.25-7.29 (1H, m, ArH), 7.34-7.43 (2H, m, ArH), 7.63 (1H, s, ArH), 7.72-7.77 (3H, m, ArH). $^{13}$C NMR (400 MHz, CD$_3$OD); δ ppm 24.40 (s, 1C), 26.82 (s, 1C), 33.90 (s, 1C), 35.58 (s, 1C), 40.01 (s, 1C), 63.43 (s, 1C), 124.01 (s, 1C), 124.90 (s, 1C), 125.00 (s, 1C), 125.52 (s, 1C), 127.13 (s, 1C), 127.75 (s, 1C), 132.35 (s, 1C), 132.17 (s, 1C), 133.46 (s, 1C). LCMS (M+1) 238.

EXAMPLE VIII

Preparation of 5-(naphthalene-2-yl)bicyclo[3.1.0]hexan-2-amines Using Reaction Scheme 3

A. Synthesis of 3-naphthalen-2-yl-cyclopent-2-enone

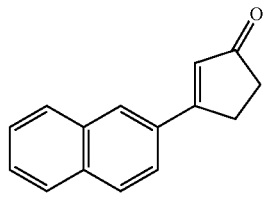

A solution of 2-bromonapthalene (8.03 g, 38.8 mmol) in anhydrous tetrahydrofuran (200 mL) at −78° C. was treated with a solution of n-butyllithium (1.6 M in hexane; 26.9 mL, 43.0 mmol, 1.1 eq.) such that the reaction temperature remained at −78° C. After 15 min, a solution of 3-methoxy-2-cyclopenten-1-one (5.0 g, 44.6 mmol, 1.1 eq.) in anhydrous tetrahydrofuran (50 mL) was added such that the reaction temperature remained below −78° C. The reaction was warmed to −20° C. over 2 h, quenched with a solution of 1N HCl (100 mL) and concentrated in vacuo to remove tetrahydrofuran. A solution of 1N HCl (100 mL) was added, stirred for 30 min and extracted with ethylacetate (3×100 mL). The combined organic extracts were washed with saturated aqueous sodium hydrogen carbonate (100 mL), brine (100 mL), dried over magnesium sulphate, filtered and concentrated in vacuo. The residue was purified by silica gel chromatography using 3:7 ethyl acetate/petrol as the eluting solvent to afford (2.77 g, 28%) as a white solid. $^1$H NMR (400 MHz, CDCl$_3$) δ ppm 2.63-2.66 (2H, m, CH$_2$), 3.17-3.20 (2H, m, CH$_2$), 6.70 (1H, t, J 1.6 Hz, CH), 7.53-7.59 (2H, m, ArH), 7.75 (1H, dd, J 1.6, 8.5 Hz, ArH), 7.85-7.93 (3H, m, ArH), 8.12 (1H, s, ArH).

B. Synthesis of 3-naphthalen-2-yl-cyclopent-2-enol

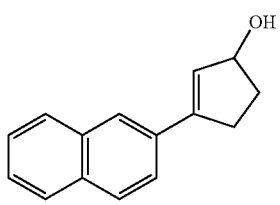

A solution of 3-(naphthalen-2-yl)cyclopent-2-enone (2.22 g, 10.7 mmol) in ethanol (250 mL) was treated with cerium trichloride (2.63 g, 10.7 mmol, 1 eq.) followed portion wise by sodium borohydride (0.48 g, 12.8 mmol, 1.2 eq.) at room temperature. The reaction mixture was stirred for 0.5 h, then quenched with saturated aqueous ammonium chloride (125 mL) and concentrated to remove ethanol. The concentrate was diluted with water (125 mL) and extracted with dichloromethane (3×125 mL). The combined organic extracts were dried over magnesium sulphate, filtered, and concentrated in vacuo to afford in a quantitative yield as a white solid which was not further purified. $^1$H NMR (400 MHz, CDCl$_3$) δ ppm 1.89-1.97 (1H, m, CH), 2.48-2.57 (1H, m, CH), 2.75-2.83 (1H, m, CH), 3.00-3.09 (1H, m, CH), 3.27 (1H, q, J 1.3 Hz, CH), 5.04-5.09 (1H, m, OH), 6.36 (1H, q, J 1.9 Hz, CH), 7.39-7.50 (2H, m ArH), 7.70 (1H, dd, J 1.6, 8.5 Hz, ArH), 7.75-7.88 (3H, m, ArH), 7.99 (1H, s, ArH).

C. Synthesis of 5-naphthalen-2-yl-bicyclo[3.1.0]hexan-2-ol

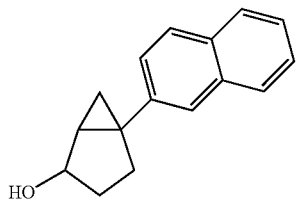

A solution of 3-(naphthalen-2-yl)cyclopent-2-enol (2.32 g, 11.0 mmol) in dichloromethane (80 mL) was treated with diethylzinc (1.0 M in hexane; 54.6 mL, 54.6 mmol, 5.0 eq.). After 10 min, the reaction mixture was cooled to 0° C., treated with a solution of diiodomethane (4.51 mL, 55.5 mmol, 5.0 eq) in dichloromethane (20 mL) dropwise over 10 min and allowed to warm to ambient temperature. After 2 h, the reaction mixture was quenched with saturated aqueous ammonium chloride (40 mL). The reaction mixture was extracted with dichloromethane (3×40 mL). The combined organic phases were dried over magnesium sulphate, concentrated in vacuo to afford the desired compound in a quantitative yield as a white solid which was not further purified. $^1$H NMR (400 MHz, CDCl$_3$) δ ppm 0.94-1.01 (1H, m, CH), 1.27-1.41 (2H, m, CH$_2$), 1.98-2.02 (1H, m, CH), 2.10-2.20 (2H, m, CH$_2$), 2.24-2.33 (1H, m, CH), 4.71-4.80 (1H, m, CH), 7.23-7.26 (1H, m, ArH), 7.40-7.48 (2H, m, ArH), 7.64 (1H, s, ArH), 7.72-7.84 (3H, m, ArH).

D. Synthesis of 5-naphthalen-2-yl-bicyclo[3.1.0]hexan-2-one

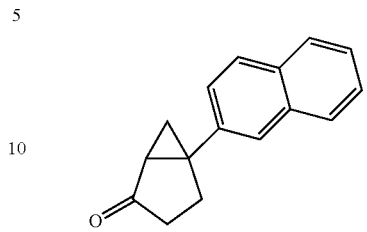

A solution of 5-(naphthalen-2-yl)bicyclo[3.1.0]hexan-2-ol (2.35 g, 10.5 mmol) in dichloromethane (110 mL) was treated with pyridine (1.18 mL, 14.6 mmol, 1.4 eq.) followed by Dess-Martin periodinane (5.34 g, 12.6 mmol, 1.2 eq.) and warmed to ambient temperature. After 2 h, 3 drops of water were added. After 0.5 h, the reaction was quenched with saturated sodium hydrogen carbonate (50 mL), saturated sodium sulphite (50 mL) and extracted with dichloromethane (3×50 mL). The combined organic extracts was dried over magnesium sulphate and concentrated in vacuo. Purification by silica gel chromatography using 1:6 ethyl acetate/petrol as the eluting solvent afforded the desired compound (1.44 g, 62%) as a yellow solid. $^1$H NMR (400 MHz, CDCl$_3$) δ ppm 1.56-1.58 (1H, m, CH), 1.71-1.75 (1H, m, CH), 2.22-2.25 (1H, m, CH), 2.30-2.34 (2H, m, CH$_2$), 2.44-2.57 (2H, m CH$_2$), 7.34 (1H, dd, J 1.9, 8.5, ArH), 7.44-7.51 (2H, m, ArH), 7.72-7.73 (1H, m, ArH), 7.80-7.83 (3H, m, ArH).

E. Synthesis of N-methyl-5-(naphthalen-2-yl)bicyclo[3.1.0]hexan-2-amine hydrochloride

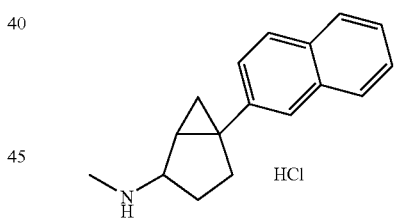

To a solution of 5-(naphthalen-2-yl)bicyclo[3.1.0]hexan-2-one (0.72 g, 3.24 mmol) in methanol (50 mL) was added methylamine (33% in ethanol, 6.05 mL, 48.6 mmol, 15.0 eq.) and sodium cyanoborohydride (0.26 g, 4.21 mmol, 1.3 eq.). The mixture was stirred at room temperature overnight. The reaction mixture was cooled to 10° C., and acidified with 1N HCl (25 mL). The reaction mixture was concentrated at 30° C. and the resulting aqueous layer diluted with water (25 mL). The aqueous layer was then extracted with ethyl acetate (125 mL) to remove non-polar impurities. The aqueous layer was then adjusted to pH 9 with 1N NaOH (25 mL), and the aqueous layer extracted with ethyl acetate (3×25 mL). The combined organic layers were dried over magnesium sulphate, filtered and concentrated in vacuo. The residue was then dissolved in diethyl ether (20 mL) and the HCl salt was formed by slowly adding HCl/diethyl ether solution (10 mL).

The slurry was stirred for 30 mins before filtration. The solids were rinsed with ice cold diethyl ether (10 mL) and the compound was quickly transferred to a vacuum oven and dried for 12 hours to afford the desired compound (0.36 g, 47%) as a white solid. ¹H NMR (400 MHz, CD₃OD) δ ppm 1.12-1.15 (1H, m, CH), 1.37-1.39 (1H, m, CH), 1.42-1.54 (1H, m, CH), 2.11-2.13 (1H, m, CH), 2.25-2.37 (2H, m, CH₂), 2.34-2.37 (1H, m, CH), 3.98-4.05 (1H, m, CH), 7.33 (1H, dd, J 1.6, 8.4, ArH), 7.40-7.47 (2H, m, ArH), 7.71-7.72 (1H, m, ArH), 7.78-7.80 (3H, m, ArH). ¹³C NMR (400 MHz, CD₃OD); δ ppm 13.41 (s, 1C), 24.40 (s, 1C), 24.50 (s, 1C), 30.55 (s, 1C), 31.69 (s, 1C), 33.3 (s, 1C), 61.44 (s, 1C), 124.75 (s, 1C), 125.28 (s, 1C), 125.91 (s, 1C), 127.25 (s, 1C), 127.28 (s, 1C), 127.85 (s, 1C), 132.32 (s, 1C), 133.59 (s, 1C), 140.18 (s, 1C). LCMS (M+1) 238.

F. Synthesis of N,N-dimethyl-5-(naphthalen-2-yl)bicyclo[3.1.0]hexan-2-amine hydrochloride

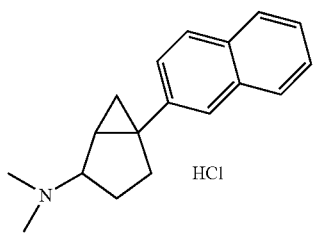

To a solution of 5-(naphthalen-2-yl)bicyclo[3.1.0]hexan-2-one (0.72 g, 3.24 mmol) in methanol (50 mL) was added dimethylamine (2M in tetrahydrofuran; 6.48 mL, 12.96 mmol, 4 eq.) and sodium cyanoborohydride (0.26 g, 4.21 mmol, 1.3 eq). The mixture was stirred at room temperature overnight. The reaction mixture was cooled to 10° C., and acidified with 1N HCl (25 mL). The reaction mixture was concentrated at 30° C. and the resulting aqueous layer diluted with water (25 mL). The aqueous layer was then extracted with ethyl acetate (125 mL) to remove nonpolar impurities. The aqueous layer was then adjusted to pH 9 with 1N NaOH (25 mL), and the aqueous layer extracted with ethyl acetate (3×25 mL). The combined organic layers were dried over magnesium sulphate, filtered and concentrated in vacuo. The residue was then dissolved in diethyl ether (20 mL) and the HCl salt was formed by slowly adding HCl/diethyl ether solution (10 mL). The slurry was stirred for 30 mins before filtration. The solids were rinsed with ice cold diethyl ether (10 mL) and the compound was quickly transferred to a vacuum oven and dried for 12 hours to afford the desired compound (0.81 g, 28%) as a white solid. ¹H NMR (400 MHz, CD₃OD) δ ppm 1.18-1.21 (1H, m, CH), 1.43-1.46 (1H, m, CH), 1.57-1.61 (1H, m, CH), 2.14-2.19 (1H, m, CH), 2.27-2.36 (2H, m, CH₂), 2.37-2.43 (1H, m, CH), 2.92 (3H, s, CH₃), 3.06 (3H, s, CH₃), 4.04-4.09 (1H, m, CH), 7.34 (1H, dd, J=1.9, 8.4, ArH), 7.39-7.47 (2H, m, ArH), 7.71-7.72 (1H, m, ArH), 7.79-7.80 (3H, m, ArH). ¹³C NMR (400 MHz, CD₃OD); δ ppm 13.74 (s, 1C), 24.28 (s, 1C), 25.31 (s, 1C), 30.70 (s, 1C), 33.53 (s, 1C), 41.58 (s, 1C), 41.89 (s, 1C), 69.80 (s, 1C), 124.50 (s, 1C), 124.75 (s, 1C), 125.33 (s, 1C), 125.93 (s, 1C), 127.25 (s, 1C), 127.87 (s, 1C), 132.35 (s, 1C), 133.57 (s, 1C), 140.02 (s, 1C). LCMS (M+1) 252.

EXAMPLE IX

Preparation of diastereomers of 1-arylbicyclo[3.1.0]hexan-3-amine Using Reaction Schemes 11 and 12

A. Synthesis of 1-aryl-2-hydroxymethyl cyclopropanecarbonitrile (1) (1R)-1-(3,4-Dichlorophenyl)-2-hydroxymethyl-cyclopropanecarbonitrile

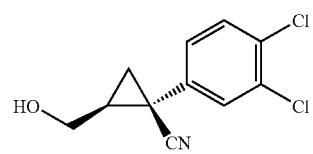

3,4-Dichlorophenyl acetonitrile (3 g, 1.6 mmole) was dissolved in dry tetrahydrofuran (THF, 25 mL) under nitrogen atmosphere. The solution was cooled to −25° C. Soda amide (0.6235, 1.6 mmol) was added portion wise maintaining the temperature of the reaction mass −25° C. The reaction mixture was allowed to warm to room temperature and maintained for 2 hours. It was then cooled to −25° C. A solution of S-(+) epichlorohydrin (1.49 g, 1.6 mmol) in tetrahydrofuran (5 mL) was added drop wise at −25° C. followed by the portion wise addition of soda amide (0.6235, 1.6 mmol). The temperature of the reaction mass was then gradually raised to room temperature over a period of 8 hours. The reaction was monitored by TLC (dichloromethane/hexane (1:1)). The reaction mass was quenched with saturated ammonium chloride solution. The aqueous layer was extracted with ethyl acetate (3×50 mL).The combined organic layer was dried over anhydrous sodium sulphate, filtered and evaporated under reduced pressure to yield 4.0 g of crude oil. The crude oil was purified by column chromatography (silica gel, dichloromethane/hexane (9:1) to yield 1.58 g (40%) of product. ¹H NMR: δ(300 MHz,CDCl3): 1.57-1.72(3H,m), 1.88-1.99 (1H,m), 3.72-3.79 (1H,dd, J=12.08,8.4 Hz), 4.06-4.12 (1H,dd, J=12.08,4.95 Hz), 7.13-7.17 (1H,m) 7.39-7.52 (2H, m).

(2) (1S)-1-(3,4-Dichlorophenyl)-2-hydroxymethyl-cyclopropanecarbonitrile

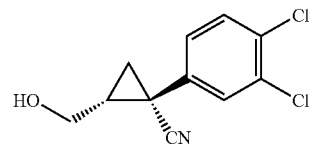

3,4-Dichlorophenyl acetonitrile (40 g, 215 mmole) was dissolved in dry tetrahydrofuran (THF, 350mL) under nitrogen atmosphere, The solution was cooled to −25° C. and soda amide (8.3 g, 215 mmol) was added portion wise maintaining the temperature of the reaction mass −25° C. The reaction mixture was allowed to warm to room temperature and maintained for 2 hours. It was then cooled to −25° C. A solution of R-(−) epichlorohydrin (19.89 g, 215 mmol) in tetrahydrofuran (50 mL) was added drop wise at −25° C. followed by the portion wise addition of soda amide (8.3 g, 250 mmol). The temperature of the reaction mass was then gradually raised to room temperature over a period of 8 hours. The reaction was monitored by TLC (dichloromethane/hexane (1:1)). The reaction mass was quenched with saturated ammonium chloride solution. The aqueous layer was extracted with ethyl acetate (3×500 mL). The combined organic layer was dried over anhydrous sodium sulphate, filtered and evaporated under reduced pressure to yield 58 g of crude oil. The crude oil was purified by column chromatography (silica gel, dichloromethane/hexane (9:1) to yield 33.4 g (64%) of product. $^1$H NMR δ(300 MHz,CDCl3): 1.59-1.67 (3H,m), 1.88-1.97 (1H,m), 3.72-3.79 (1H,m), 4.06-4.12 (1H,m), 7.13-7.17 (1H,m) 7.39-7.52 (2H,m).

(3) (1R)-2-Hydroxymethyl-1-(1-naphthyl)-cyclopropanecarbonitrile

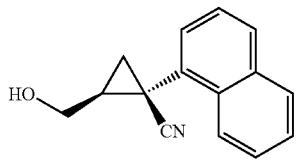

1-Naphthylacetonitrile (30 g, 180 mmole) was dissolved in dry tetrahydrofuran (THF, 300 mL) under nitrogen atmosphere, cooled to −15° C. and sodium-bis (trimethylsilylamide) in 1M tetrahydrofuran (180 mL) was added drop wise at −15° C. The resulting brown mixture was stirred for 45 min at −10° C. to 0° C. Then cooled the reaction mass to −15° C. A solution of S-(+) epichlorohydrin (16.6 g, 180 mmol) in tetrahydrofuran (20 mL) was added drop wise at −15° C. and stirred for 30 minutes. Sodiumbis (trimethylsilylamide) in 1M THF (180 mL) is added drop wise at −15° C. and the mixture was stirred for 45 min. The temperature of the reaction mass was then gradually raised to room temperature and maintained at room temperature for 30 minutes. The reaction is monitored by TLC (ethyl acetate/hexane (1:1)). The reaction was quenched with water (80mL). The aqueous layer was extracted with ethyl acetate (2×75 mL). The combined organic layer was washed with brine solution (200 mL), dried over anhydrous sodium sulphate, filtered and evaporated under reduced pressure to yield 55 g of crude oil, which was purified by column chromatography (silica gel, ethyl acetate/hexane (10:90) to yield 28 g (69%) of product. The $^1$H NMR shows mixture of diasteromers (2:1 cis/trans). $^1$H NMR δ((300 MHz,CDCl3, partial assignment): 1.57-1.62 (2H,m), 1.92-2.03 (1H,m), 3.10-3.25 (1H,br,s), 3.91-3.97 (1H,m) 4.22-4.27 (1H,m), 7.37-7.69 (4H,m), 7.82-7.92 (2H,m), 8.36-8.49 (1H,m).

(4) (1S)-2-Hydroxymethyl-1-(1-naphthyl)-cyclopropanecarbonitrile

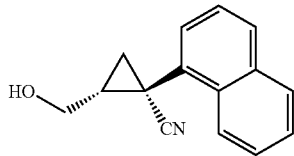

1-Naphthylacetonitrile (30 g, 180 mmole) was dissolved in dry tetrahydrofuran (THF, 300 mL) under nitrogen atmosphere, cooled to −15° C. and sodium-bis (trimethylsilylamide) in 1M tetrahydrofuran (180 mL) was added dropwise. The resulting brown mixture was stirred for 45 min at −10° C. to 0° C., cooled to −15° C. and added a solution of R-(+) epichlorohydrin (16.6 g, 180 mmol) in tetrahydrofuran (20 mL) was added dropwise at −15° C. and stirred for 30 min. Sodiumbis (trimethylsilylamide) in 1M tetrahydrofuran (180 mL) is added drop wise at −15° C. and the mixture was stirred for 45 min. The temperature of the reaction mass was then gradually raised to room temperature and maintained at room temperature for 30 min. The reaction is monitored by TLC (ethyl acetate/hexane (1:1)). The reaction mass was quenched with water (80 mL). The aqueous layer was extracted with ethyl acetate (2×75 mL). The combined organic layer was washed with brine solution (200 mL), dried over anhydrous sodium sulphate, filtered and evaporated under reduced pressure to yield 55 g of crude oil. The oil was purified by column chromatography (silica gel, ethyl acetate/hexane (10:90) to yield 25 g (62%) of product. The $^1$H NMR shows mixture of diasteromers (2:1 cis/trans). $^1$H NMR δ(300 MHz,CDCl3, partial assignment): 1.55-1.59 (2H,m), 1.94-2.04 (1H,m), 2.42 (1H,m) 3.08 (1H,br,s), 3.32 (1H,m),7.42-7.68 (4H,m), 7.72-7.93 (2H,m),8.37-8.40 (1H,d,J=8.4 Hz).

B. Synthesis of 1-aryl-3-oxabicyclo[3.1.0]hexan-2-one (1) (1R,5S)-1-(3,4-Dichlorophenyl)-3-oxabicyclo[3.1.0]hexan-2-one

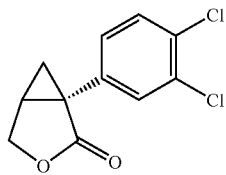

(1R)-1-(3,4-Dichloro-phenyl)-2-hydroxymethyl cyclopropanecarbonitrile (24 g, 9.9 mmol), ethanol (48 mL) and 25N sodium hydroxide solution (24 mL) were heated under reflux for 18 hours. The reaction is monitored by TLC (dichloromethane (100%)). The reaction mixture was cooled to room temperature and ice cold water (24 mL) was added to the reaction mass followed by concentrated hydrochloric acid drop wise to adjust the pH of the reaction mass to 1-2 and stirred for overnight at room temperature. The aqueous layer was extracted with dichloromethane (100 mL). The organic layer was washed with 3% sodium bicarbonate solution, dried over anhydrous sodium sulphate, filtered and evaporated under reduced pressure to yield 13 g (55%) of product. $^1$H NMR δ(300 MHz,CDCl3): 1.41-1.43 (1H,t,J=4.9 Hz), 1.58-1.63 (1H,dd,J=7.8,5.0 Hz), 2.56-2.59 (1H,m), 4.28-4.31 (1H, d, J=9.3 Hz), 4.44-4.48 (1H, dd, J=9.4, 4.6 Hz), 7.26-7.30 (1H,dd,J=8.4,2.1 Hz), 7.40-7.43 (1H,d,J=8.4 Hz) 7.52-7.53 (1H,d,J=2 Hz).

(2) (1S,5R)-1-(3,4-Dichlorophenyl)-3-oxabicyclo[3.1.0]hexan-2-one

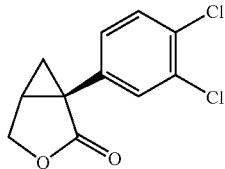

(1S)-1-(3,4-dichloro-phenyl)-2-hydroxymethyl cyclopropanecarbonitrile (10 g, 4.13 mmol), ethanol (20 mL) and 25N sodium hydroxide solution (10 mL) were heated under reflux for 18 hours. The reaction is monitored by TLC (dichloromethane (100%)). The reaction mixture was cooled to room temperature and ice cold water (10 mL) was added to the reaction mass followed by concentrated hydrochloric acid drop wise to adjust the pH of the reaction mass to 1-2 and stirred for overnight at room temperature. The aqueous layer was extracted with dichloromethane (100 mL). The organic layer was washed with 3% sodium bicarbonate solution, dried over anhydrous sodium sulphate, filtered and evaporated under reduced pressure to yield 4.5 g (45%) of product. $^1$H NMR δ(300 MHz,CDCl3): 1.41-1.43 (1H,t, J=4.9 Hz), 1.58-1.63 (1H,dd, J=7.79,4.94 Hz), 2.56-2.62 (1H,m), 4.28-4.31 (1H,d, J=9.3 Hz), 4.44-4.48 (1H,dd, J=9.34,4.58 Hz), 7.26-7.30 (1H,dd, J=8.2,2.0 Hz), 7.40-7.43 (1H,d, J=8.2 Hz), 7.52-7.53 (1H,d, J=2 Hz).

(3) (1R,5S)-1-(1-naphthyl)-3-oxabicyclo[3.1.0]hexan-2-one

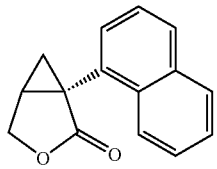

(1R)-2-Hydroxymethyl-1(1-naphthyl)-cyclopropanecarbonitrile (1a 10 g, 44.6 mmol), ethanol (20 mL) and 25N sodium hydroxide solution (10 mL) were heated under reflux for 18 hours. The reaction is monitored by TLC (dichloromethane (100%)). The reaction mixture was cooled to room temperature and ice cold water (12 mL) was added to the reaction mixture followed by concentrated hydrochloric acid drop wise to adjust the pH of the reaction mass to 1-2 and stirred for overnight. The aqueous layer was extracted with dichloromethane (200 mL). The organic layer was washed with 3% sodium bicarbonate solution, dried over anhydrous sodium sulphate, filtered and evaporated under reduced pressure to yield 5 g (50%) of product. $^1$H NMR δ(300 MHz, CDCl3): 0.78-0.81 (1H,m), 1.45-1.48 (1H,m,), 1.68-1.72 (1H,m,) 2.45-2.51 (1H,m), 4.37-4.40 (1H,d, J=9 Hz), 4.65-4.69 (1H,dd, J=9,3 Hz), 7.34-7.52 (4H,m), 7.76-7.91 (3H,m).

(4) (1S,5R)-1-(1-naphthyl)-3-oxabicyclo[3.1.0]hexan-2-one

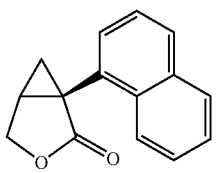

(1S)-2-hydroxymethyl-1-(1-naphthyl)-cyclopropanecarbonitrile (300 mg, 1.3 mmol) ethanol (0.6 mL) and 25N sodium hydroxide solution (0.3 mL) were heated under reflux for 18 hours. The reaction is monitored by TLC (dichloromethane (100%)). The reaction mixture was cooled to room temperature and ice cold water (12 mL) was added to the reaction mixture followed by concentrated hydrochloric acid drop to adjust the pH of the reaction mass to 1-2 and stirred for overnight. The aqueous layer was extracted with dichloromethane (25 mL). The organic layer was washed with 3% sodium bicarbonate solution, dried over anhydrous sodium sulphate, filtered and evaporated under reduced pressure to yield 128 mg (44%) of product. $^1$H NMR δ(300 MHz, CDCl3): 1.51-1.54 (1H,t, J=4.58,), 1.74-1.78 (1H,dd, J=7.7, 4.8 Hz), 2.53-2.57 (1H,m), 4.43-4.46 (1H,d,J=9.5 Hz), 4.71-4.76 (1H,dd,J=9.3,4.5 Hz), 7.40-7.58 (4H,m), 7.83-7.89 (2H, m), 7.95-7.98 (1H d,J=8.2 Hz).

C. Synthesis of (2-aryl-2-hydroxymethylcyclopropyl)methanol

(1) ((2R)-2-(3,4-Dichlorophenyl)-2-hydroxymethyl-cyclopropyl)methanol

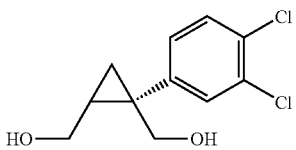

BMS (17.16 mL, 18 mmol) was added to (1R)-1-(3,4-dichlorophenyl)-3-oxabicyclo[3.1.0]hexan-2-one (22 g, 9 mmol) in dry tetrahydrofuran (200 mL), under nitrogen atmosphere. The reaction mass was refluxed for 5 hours and monitored by TLC (dichloromethane (100%)). The reaction mass was quenched with 10% potassium carbonate solution. The aqueous layer was extracted with dichloromethane (2×250 mL). The combined organic layer was dried over anhydrous sodium sulfate, filtered and evaporated under reduced pressure to yield 20.4 g (92%) of desired product. $^1$H NMR δ(300 MHz,CDCl3): 0.9-1.25 (1H,m), 1.35-1.52 (1H,m), 1.75-1.79 (1H,m), 3.32-3.42 (2H,m) 3.97-4.12 (2H,m) 7.26-7.30 (1H, dd,J=8.4,2.1 Hz), 7.40-7.43 (1H,d,J=8.4 Hz), 7.52-7.53 (1H, d,J=2 Hz).

(2) ((2S)-2-(3,4-Dichlorophenyl)-2-hydroxymethyl-cyclopropyl)methanol

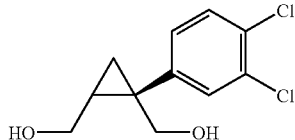

BMS (10.9 mL, 115 mmol) was added to (1S)-1-(3,4-dichloro-phenyl)-3-oxabicyclo[3.1.0]hexan-2-one (14 g, 57.6 mmol) in dry tetrahydrofuran (140 mL), under nitrogen atmosphere. The reaction mass was refluxed for 5 hours and monitored by TLC (dichloromethane (100%)). The reaction was quenched with 10% potassium carbonate solution. The aqueous layer was extracted with dichloromethane (2×250 mL). The combined organic layer was dried over anhydrous sodium sulphate, filtered and evaporated under reduced pressure to yield 14 g (98.5%) of desired product. $^1$H NMR δ(300 MHz,CDCl3): 0.9-0.98 (1H,m), 1.17 (1H,m), 1.48 (1H,m), 3.23-3.42 (2H,m) 3.92-4.03 (2H,m) 7.10-7.13 (1H,m), 7.24-7.27 (1H,m), 7.38 (1H,m,).

(3) ((2R)-2-(1-naphthyl)-2-hydroxymethylcyclopropyl)methanol

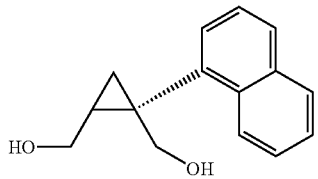

BMS (8.10 mL, 107 mmol) was added to (1R)-1-(1-naphthyl)-3-oxabicyclo[3.1.0]hexan-2-one (12 g, 53.5 mmol) in dry tetrahydrofuran (100 mL) under nitrogen atmosphere. The reaction mass was refluxed for 5 hours and monitored by TLC (dichloromethane (100%)). The reaction was quenched with 10% potassium carbonate solution. The aqueous layer was extracted with dichloromethane (2×150 mL). The combined organic layer was dried over anhydrous sodium sulfate, filtered and evaporated under reduced pressure to yield 20.4 g (92%) of desired product. $^1$H NMR δ(300 MHz,CDCl3): 0.87 (1H,m), 1.01-1.25 (2H,m,), 1.78-1.83 (2H,m,) 3.4-3.7 (2H,m), 4.12-4.18 (2H,m), 7.36-7.52 (4H,m), 7.57-7.75 (1H,m) 7.83-7.86 (1H,m) 8.25 (1H,brs).

(4) ((2S)-2-(1-naphthyl)-2-hydroxymethylcyclopropyl)methanol

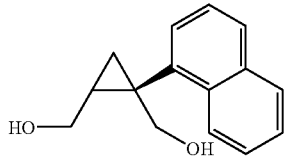

BMS (0.2 mL, 0.8 mmol) was added to (1S)-1-(1-naphthyl)-3-oxabicyclo[3.1.0]hexan-2-one (90 mg, 0.4 mmol) in dry tetrahydrofuran (1 mL), under nitrogen atmosphere. The reaction mass was refluxed for 5 hours and monitored by TLC (dichloromethane (100%)). The reaction mass was quenched with 10% potassium carbonate solution. The aqueous layer was extracted with dichloromethane (2×10 mL). The combined organic layer was dried over anhydrous sodium sulphate, filtered and evaporated under reduced pressure to yield 90 mg (98.5%) of desired product. $^1$H NMR δ(300 MHz, CDCl3): 1.09-1.43 (3H,m), 1.67-1.69 (2H,m,) 1.83-1.90 (1H, m), 3.5-3.7 (2H,m), 4.25-4.27 (2H,m), 7.4-7.65 (4H,m), (1H, m) 7.77-7.89 (2H,m), 8.25 (1H,brs).

D. Synthesis of 1,2-bis(bromomethyl)-1-arylcyclopropane

(1) (1R)-1,2-bis(bromomethyl)-1-(3,4-Dichlorophenyl)cyclopropane

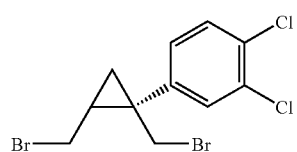

To a solution of ((2R)-2-(3,4-Dichlorophenyl)-2-hydroxymethylcyclopropyl)-methanol (20 g, 8.1 mmol) in dichloromethane (100 mL) was added carbon tetra bromide (236 g, 71.2 mmol) at room temperature. Triphenylphosphine (87.1, 71.2 mmol) was added portion wise under nitrogen atmosphere at 0° C. The reaction mass was stirred for overnight at room temperature. The reaction was monitored by TLC (hexane (100%)) and quenched with methanol (50 mL). The reaction mixture was concentrated under reduced pressure to obtain crude viscous mass (150 g). The crude product was purified by column chromatography (silica gel, ethyl acetate/hexane (3:97) to yield 10 g (33%) of desired product. $^1$H NMR δ(300 MHz,CDCl3): 0.9-1.12 (1H,t,J=6 Hz), 1.48-1.53 (1H,dd,J=9,6 Hz), 1.91-1.96 (1H,m), 3.48-3.63 (2H,m),.3.71-3.78 (2H,m), 7.22-7.26 (1H,dd,J=8.4,2.1 Hz), 7.39-7.42 (1H,d,J=8.4 Hz), 7.47-7.48 (1H,d,J=2 Hz).

(2) (1S)-1,2-bis(bromomethyl)-1-(3,4-Dichlorophenyl)cyclopropane

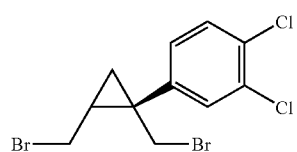

To a solution of ((2S)-2-(3,4-Dichlorophenyl)-2-hydroxymethylcyclopropyl)methanol (6 g, 24.3 mmol) in dichloromethane (100 mL) was added carbon tetrabromide (70.9 g, 213 mmol) at room temperature. Triphenyl phosphine (55.8 g 213 mmol) was added portion wise under nitrogen atmosphere at 0° C. The reaction mass was stirred for overnight at room temperature. The reaction was monitored by TLC (hexane (100%)) and quenched with methanol (50 mL). The reaction mixture was concentrated under reduced pressure to obtain crude viscous mass (50 g). The crude product was purified by column chromatography (silica gel, ethyl acetate/hexane (3:97) to yield 4 g (45%) of desired product. $^1$H NMR δ(300 MHz,CDCl3): 0.9-1.03 (1H,t,J=0 Hz), 1.47-1.52 (1H,dd,J=9.6 Hz), 1.93 (1H,m), 3.48-3.63 (2H,m), 3.70-3.77 (2H,m), 7.22-7.26 (1H,dd,J=9,3 Hz), 7.39-7.42 (1H,d,J=9 Hz), 7.47-7.48 (1H,d,J=3 Hz).

(3) (1R)-1,2-bis(bromomethyl)-1-(1-naphthyl)cyclopropane

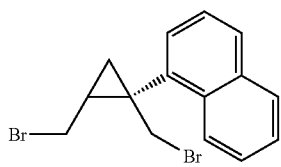

To a solution of (((2R)-2-(1-naphthyl)-2-hydroxymethyl-cyclopropyl)methanol (8 g, 52.6 mmol) in dichloromethane (60 mL) was added carbon tetrabromide (153.6 g, 463 mmol) at room temperature. Triphenyl phosphine (121.4,463 mmol) was added portion wise under nitrogen atmosphere at 0° C. The reaction mass was stirred for overnight at room temperature. The reaction was monitored by TLC (hexane (100%)) and quenched with methanol (50 mL). The reaction mixture was concentrated under reduced pressure to obtain crude viscous mass (95 g). The crude product was purified by column chromatography (silica gel, ethyl acetate/hexane (3:97) to yield 5 g (28%) of desired product. $^1$H NMR δ(300 MHz, CDCl3) 1.01-1.25 (1H,m,), 1.48-1.58 (1H,m,) 2.01-2.14 (1H,m), 3.5-4.2 (4H,brm), 7.36-7.52 (4H,m), 7.57-7.75 (1H,m) 7.76-7.96 (2H,m) 8.25 (1H,brs).

(4) (1S)-1,2-bis(bromomethyl)-1-(1-naphthyl)cyclopropane

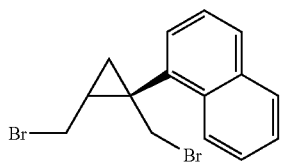

To a solution of ((2S)-2-(1-naphthyl)-2-hydroxymethylcyclopropyl)methanol (14 g, 61 mmol) in dichloromethane (100 mL) was added carbon tetrabromide (179.19 g, 540 mmol) at room temperature. Triphenyl phosphine (141.6,540 mmol) was added portion wise under nitrogen atmosphere at 0° C. The reaction was stirred for overnight at room temperature. The reaction was monitored by TLC (hexane (100%)) and quenched with methanol (50 mL). The reaction mixture was concentrated under reduced pressure to obtain crude viscous mass (140 g). The crude product was purified by column chromatography (silica gel, ethyl acetate/hexane (3:97) to yield 8.5 g (39%) of desired product. $^1$H NMR δ(300 MHz,CDCl3) 1.01-1.25 (1H,m,), 1.48-1.58 (1H,m,) 2.01-2.14 (1H,m), 3.5-4.2 (4H,brm), 7.36-7.52 (4H,m), 7.57-7.75 (1H,m) 7.76-7.96 (2H,m) 8.25 (1H,brs).

E. Synthesis of 1-aryl-3-Benzenesulfonyl-3-methyl-sulfanyl-bicyclo[3.1.0]hexane (1) (1R,5R)-3-Benzenesulfonyl-1-(3,4-dichlorophenyl)-3-methylsulfanyl-bicyclo[3.1.0]hexane

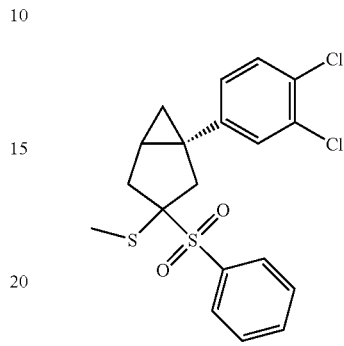

1-((Methylthio)methylsulfonyl)benzene (8.12 g, 40.2 mmole) was dissolved in dry dimethylformamide (DMF, 60 mL). Sodium hydride (2.4 g, 100 mmol) was added portion wise under nitrogen atmosphere at 0° C. The reaction mass was gradually heated to 40° C. and maintained for 30 minutes at 40° C. A solution of (1R)-4-(1,2-bis-bromomethyl-cyclopropylo-1,2-dichloro-benzene (10 g, 26 mmol) in DMF (40 mL) was added dropwise for 30 min at 0° C. The temperature of the reaction mass was gradually brought to room temperature and maintained for 7 hours. The reaction was monitored by TLC (ethyl acetate/hexane (10:90)). The reaction mass was quenched with water. The aqueous layer was extracted with diethyl ether (2×300 mL).The combined organic layer was dried over anhydrous sodium sulfate, filtered and evaporated under reduced pressure to yield 18.0 g of crude oil, which was purified by column chromatography (silica gel, ethyl acetate/hexane (4:96) to yield 5 g (45%) of product. $^1$H NMR δ(300 MHz,CDCl3): 1.73 (1H,m), 1.85 (2H,m), 2.09 (3H,s), 2.29 (2H,m), 2.54 (1H,m), 2.87 (1H,dd, J=15 Hz), 7.12 (1H,d, J=3 Hz), 7.15 (1H,d, J=3 Hz), 7.25 (1H,m), 7.3 (1H,d, J=9 Hz), 7.5-7.55 (2H,m), 7.91 (2H,m).

(2) (1S,5S)-3-Benzenesulfonyl-1-(3,4-dichlorophenyl)-3-methylsulfanyl-bicyclo[3.1.0]hexane

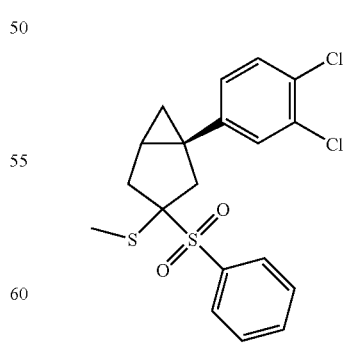

1-((Methylthio)methylsulfonyl)benzene (2.95 g, 14.6 mmole) was dissolved in dry dimethylforamide (DMF, 40 mL). Sodium hydride (1.75 g, 36.5 mmol) was added portion wise under nitrogen atmosphere at 0° C. The mass was gradually heated to 40° C. and maintained for 30 min at 40° C. A solution of (1S)-1,2-bis(bromomethyl)-1-(3,4-Dichlorophenyl)cyclopropane (5.65 g, 14.65 mmol) in DMF (10 mL) was added dropwise for 30 minutes at 0° C. The temperature of the reaction mass was brought to room temperature slowly and maintained for 7 hours. The reaction was monitored by TLC (ethyl acetate/hexane (10:90)). The reaction mass was quenched with water. The aqueous layer was extracted with diethyl ether (2×250 mL). The combined organic layer was dried over anhydrous sodium sulfate, filtered and evaporated under reduced pressure to yield 8 g of crude oil that was purified by column chromatography (silica gel, ethyl acetate/hexane (4:96) to yield 2 g (33%) of product. $^1$H NMR δ(300 MHz,CDCl3): 1.73 (1H,m), 1.85 (2H,m), 2.04 (3H,s), 2.29 (2H,m), 2.54 (1H,m), 2.88 (1H, dd, J=15 Hz), 7.12 (1H,d,J=3 Hz), 7.15 (1H,d,J=3 Hz), 7.25 (1H,m), 7.3 (1H,d,J=9 Hz), 7.55-7.57 (2H,m), 7.91 (2H,m).

(3) (1R,5R)-3-Benzenesulfonyl-1-(1-naphthyl)-3-methylsulfanyl-bicyclo[3.1.0]hexane

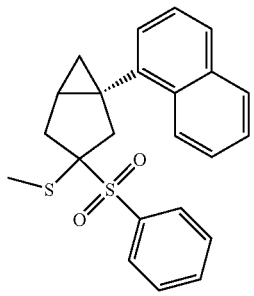

1-((Methylthio)methylsulfonyl)benzene (2.85 g, 14.1 mmole) was dissolved in dry dimethylforamide (DMF, 15 mL). Sodium hydride (1.69 g, 35.3 mmol) was added portion wise under nitrogen atmosphere at 0° C. The reaction mass was gradually heated to 40° C. and maintained for 30 min at 40° C. A solution of (1R)-1,2-bis(bromomethyl)-1-(1-naphthyl)cyclopropane (2.5 g, 7.0 mmol) in DMF (5 mL) was added dropwise for 30 min at 0° C. The temperature of the reaction mass was slowly brought to room temperature and maintained for 7 hours. The reaction was monitored by TLC (ethyl acetate/hexane (10:90)). The reaction mass was quenched with water. The aqueous layer was extracted with diethyl ether (2×150 mL). The combined organic layer was dried over anhydrous sodium sulfate, filtered and evaporated under reduced pressure to yield 10.0 g of crude oil that was purified by column chromatography (silica gel, ethyl acetate/hexane (4:96) to yield 1.92 g (69%) of product. $^1$H NMR δ(300 MHz,CDCl3): 1.93 (2H,m), 2.01 (1H,m), 2.07 (3H,s), 2.28 (2H,m), 2.44 (2H,m), 2.88 (1H,dd, J=15 Hz), 7.36 (1H,m), 7.47-7.68 (7H,m), 7.74 (1H,m), 7.91-7.97 (3H,m).

(4) (1S,5S)-3-Benzenesulfonyl-1-(1-naphthyl)-3-methylsulfanyl-bicyclo[3.1.0]hexane

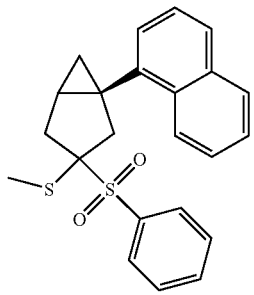

1-((Methylthio)methylsulfonyl)benzene (6.54 g, 32.2 mmole) was dissolved in dry dimethylforamide (DMF, 40 mL). Sodium hydride (3.86 g, 80.5 mmol) was added portion wise under nitrogen atmosphere at 0° C. The reaction mass was gradually heated to 40° C. and maintained for 30 minutes at 40° C. (1S)-1,2-bis(bromomethyl)-1-(1-naphthyl)cyclopropane (5.7 g, 6.1 mmol) dissolved in DMF (15 mL) was added dropwise for 30 min at 0° C. The temperature of the reaction mass was gradually brought to room temperature and maintained for 7 hours. The reaction was monitored by TLC (ethyl acetate/hexane (10:90)). The reaction mass was quenched with water. The aqueous layer was extracted with diethyl ether (2×250 mL). The combined organic layer was dried over anhydrous sodium sulfate, filtered and evaporated under reduced pressure to yield 12.0 g of crude oil that was purified by column chromatography (silica gel, ethyl acetate/hexane (4:96) to yield 3.5 g (53%) of product. $^1$H NMR δ(300 MHz,CDCl3): 1.93 (2H,m), 2.01 (1H,m), 2.07 (3H,s), 2.28 (2H,m), 2.44 (2H,m), 2.88 (1H, dd, J=15 Hz), 7.36 (1H,m), 7.47-7.68 (7H,m), 7.74 (1H,m), 7.91-7.97 (3H,m).

F. Synthesis of 1-arylbicyclo[3.1.0]hexan-3-one (1) (1R,5R)-1-(3,4-Dichlorophenyl)bicyclo[3.1.0]hexan-3-one

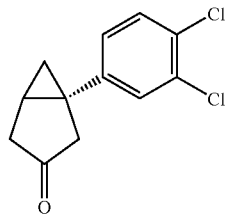

(1R,5R)-3-Benzenesulfonyl-1-(3,4-dichlorophenyl)-3-methylsulfanyl-bicyclo[3.1.0]hexane (1.4 g, 3.3 mmol), methanol (6 mL) and concentrated hydrochloric acid (1.5 mL) were heated to reflux for 7 hours. The reaction was monitored by TLC (ethyl acetate/hexane (20:80)). The reaction mixture was concentrated under reduced pressure to remove methanol. The pH of the reaction mass was adjusted to 8-9 with saturated sodium bicarbonate solution. The aqueous layer was extracted with diethyl ether (100 mL). The organic layer was washed with water, dried over anhydrous sodium sulphate, filtered and evaporated under reduced pressure to yield 1.1 g of crude oil, which was purified by preparative HPLC to yield 560 mg (70%) of 99% pure product. $^1$H NMR δ(300 MHz,CDCl3) 0.67-0.70 (1H,t, J=4 Hz), 1.25-1.35 (1H,m), 1.94-2.15 (1H,m), 2.36-2.42 (1H,d ,J=18 Hz), 2.59-2.65 (1H,d,J=18 Hz), 2.83-2.89 (2H,m), 6.99-7.03 (1H, dd,J=9.3 Hz), 7.25-7.26 (1H,d,J=3 Hz),7.36-7.39 (1H,d,J=9 Hz). $^{13}$CNMR(CDCl3) δ: 215.25, 143.49, 132.55, 130.39, 130.06, 128.07, 125.40, 45.34, 42.08, 27.18, 23.32, 22.24.

(2) (1S,5S)-1-(3,4-Dichlorophenyl)bicyclo[3.1.0]hexan-3-one

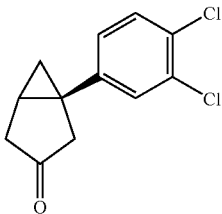

(1S,5S)-3-Benzenesulfonyl-1-(3,4-dichlorophenyl)-3-methylsulfanyl-bicyclo[3.1.0]hexane (3.5 g, 8.4 mmol), methanol (15 mL) and concentrated hydrochloric acid (3 mL) were heated to reflux for 7 hours. The reaction was monitored by TLC (ethyl acetate/hexane(20:80)). The reaction mixture was concentrated under reduced pressure to remove methanol. The pH of the reaction mass was adjusted to 8-9 with saturated sodium bicarbonate solution. The aqueous layer was extracted with diethyl ether (300 mL). The organic layer was washed with water, dried over anhydrous sodium sulfate, filtered and evaporated under reduced pressure to yield 3 g of crude oil, which was purified by preparative HPLC to give 900 mg (45%) of 99% pure product. $^1$H NMR δ(300 MHz, CDCl3) 0.68-0.70 (1H,t, J=4 Hz), 1.25-1.35 (1H,m), 1.94-2.15 (1H,m), 2.36-2.42 (1H, d, J=10 Hz), 2.59-2.66 (1H,d, J=10 Hz), 2.83-2.89 (2H,m), 6.99-7.03 (1H,dd,J=9,3 Hz), 7.25-7.26 (1H,d,J=3 Hz), 7.36-7.39 (1H,d,J=9 Hz). $^{13}$CNMR (CDCl3)δ: 215.28, 143.49, 132.57, 130.4, 130.07, 128.09, 125.41, 45.35, 42.08, 27.20, 23.31, 22.23.

(3) (1R,5R)-1-(1-naphthyl)bicyclo[3.1.0]hexan-3-one

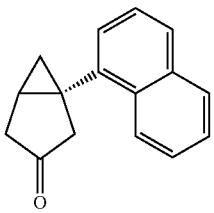

(1R,5R)-3-Benzenesulfonyl-1-(1-naphthyl)-3-methylsulfanyl-bicyclo[3.1.0]hexane (620 mg, 1.6 mmol), methanol (4 mL) and concentrated hydrochloric acid (0.7 mL) were heated to reflux for 7 hours. The reaction was monitored by TLC (ethyl acetate/hexane (20:80)) The reaction mixture was concentrated under reduced pressure to remove methanol. The pH of the reaction mass was adjusted to 8-9 with saturated sodium bicarbonate solution. The aqueous layer was extracted with diethyl ether (50 mL). The organic layer was washed with water, dried over anhydrous sodium sulphate, filtered and evaporated under reduced pressure to yield 458 mg of crude oil, which was purified by preparative HPLC to yield 135 mg (39%) of 99% pure product. $^1$H NMR δ(300 MHz,CDCl3) 0.76-0.79 (1H,t, J=4 Hz), 1.38 (1H,m), 2.01 (1H,m), 2.49-2.56 (1H,d, J=10Hz), 2.75 (2H,d,J=6 Hz), 3.05-3.15 (2H,dd,J=10 Hz), 7.40-7.45 (1H,m), 7.50-7.56 (3H,m), 7.76-7.79 (1H,d,J=9 Hz), 7.88-7.90 (1H,m), 8.13-8.15 (2H,d ,J=6 Hz). $^{13}$CNMR(CDCl3)δ: 218.25, 139.12, 134.01, 128.96, 127.80, 126.77, 126.17, 125.78, 125.33, 124.0, 48.18, 42.46, 27.80, 20.62, 20.05.

(4) (1S,5S)-1-(1-naphthyl)bicyclo[3.1.0 ]hexan-3-one

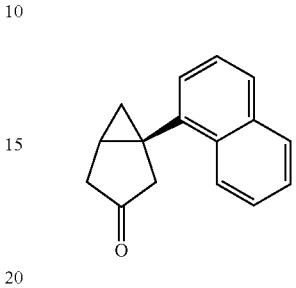

(1S,5S)-3-Benzenesulfonyl-1-(1-naphthyl)-3-methylsulfanyl-bicyclo[3.1.0]hexane (3 g, 7.6 mmol), methanol (18 mL) and concentrated hydrochloric acid (5.4 mL) were heated to reflux for 7 hours. The reaction was monitored by TLC (ethyl acetate/hexane (20:80)).The reaction mixture was concentrated under reduced pressure to remove methanol. The pH of the reaction mass was adjusted to 8-9 with saturated sodium bicarbonate solution. The aqueous layer was extracted with diethyl ether (300 mL). The organic layer was washed with water, dried over anhydrous sodium sulphate, filtered and evaporated under reduced pressure to yield 3 g of crude oil, which was purified by preparative HPLC to give 1 g (62%) of 99% pure product. $^1$H NMR δ(300 MHz,CDCl3): 0.75-0.78 (1H,t, J=4 Hz), 1.37 (1H,m), 1.98-2.04 (1H,m), 2.49-2.55 (1H,d ,J=18 Hz), 2.77-2.79 (2H,d,J=6 Hz), 3.03-3.11 (2H,dd,J=18,6 Hz), 7.39-7.44 (1H,m), 7.48-7.57 (3H,m),7.76-7.78 (1H,d,J=6 Hz), 7.87-7.90 (1H,m), 8.12-8.15 (2H,d ,J=9 Hz).

$^{13}$CNMR(CDCl3)δ: 218.25, 139.05, 133.93, 132.48, 128.91, 127.75, 126.7, 126.13, 125.74, 125.45, 124.36, 48.12, 42.43, 27.74, 20.54, 19.99.

G. Synthesis of 1-arylbicyclo[3.1.0]hexan-3-amine

(1) (1R,5R)-1-(3,4-Dichlorophenyl)bicyclo[3.1.0]hexan-3-amine

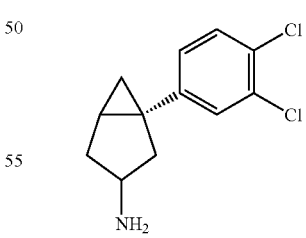

To a solution of (1R,5R)-1-(3,4-dichlorophenyl)bicyclo [3.1.0]hexan-3-one (0.9 g, 3.73 mmol) in methanol (112 mL) was added ammonium acetate (28.3 g, 373 mmol), stirred for 15 minutes at room temperature and sodiumcyano borohydride (1.87 g, 30.8 mmol) was added and the mixture was heated to 60° C. for 2 hours. The reaction was monitored by TLC (ethyl acetate/methanol/triethylamine (89:10:1)). The reaction mixture was concentrated under reduced pressure to remove methanol at 30° C., the residual mass was quenched with water (50 mL) and the aqueous layer was extracted again with ethyl acetate (3×100 mL). The aqueous layer was saturated with sodium chloride and re-extracted with ethyl acetate (3×100 mL). The organic layers were combined, dried over anhydrous sodium sulphate, filtered and evaporated under reduced pressure to yield 2.4 g of crude oil, which was purified by preparative HPLC to give 600 mg (66%) of 99% pure product. $^1$H NMR δ(300 MHz,CD3OD): 0.92-0.99 (2H,m), 1.27 (1H,m), 1.78-1.83 (3H,m), 2.04-2.15 (2H,m), 2.57-2.74 (3H,m), 3.98-4.01 (1H,m), 7.11-7.14 (1H,m), 7.36-7.41 (2H, m). $^{13}$CNMR(CD3OD) δ: 145.92, 133.22, 131.50, 130.76, 129.77, 129.30, 127.57, 127.06, 54.35, 40.52, 37.67, 35.74, 34.36, 33.53, 31.10, 28.25, 26.08, 25.87, 18.50. Purity: 99.15% (a/a) by HPLC. MS, M+(241).

HCl Salt: To a solution of(1R,5R)-1-(3,4-dichlorophenyl) bicyclo[3.1.0]hexan-3-amine (400 mg, 1.65 mmol) in diethyl ether (10 mL), was added HCl/diethylether (2 mL) solution at 0° C. and stirred for 30 minutes at room temperature. The slurry mass was filtered and washed with diethyl ether (10 mL) and dried under vacuum for 12 hours to yield 320 mg of white solid (69.5%). $^1$H NMR δ(300 MHz,CD3OD): 0.91-0.94 (2H,m), 1.18 (1H,m), 1.74-1.75 (3H,m), 2.01-2.08 (2H, m), 2.50-2.66 (3H,m), 3.92-3.95 (1H,m), 7.03-7.06 (1H,m), 7.26-7.34 (2H,m).

$^{13}$CNMR(CD3OD) δ: 145.93, 133.19, 131.50, 130.72, 129.76, 129.30, 127.59, 127.09, 54.39, 40.50, 37.64, 35.73, 34.35, 33.53, 31.09, 28.27, 26.09, 25.93, 18.51. Purity: 99.56% (a/a) by HPLC. MS, M+(241).

(2) (1S,5S)-1-(3,4-Dichlorophenyl)bicyclo[3.1.0]hexan-3-amine

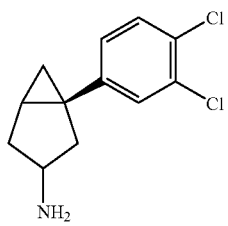

To a solution of (1S,5S)-1-(3,4-dichlorophenyl)bicyclo[3.1.0]hexan-3-one (0.7 g, 2.9 mmol) in methanol (87.5 mL) was added ammonium acetate (22.05 g, 290 mmol), stirred for 15 minutes at room temperature and sodium cyanoborohydride (1.45 g, 23 mmol) was added and the mixture was heated to 60° C. for 2 hours. The reaction was monitored by TLC (ethyl acetate/methanol/triethylamine (89:10:1)). The reaction mixture was concentrated under reduced pressure to remove methanol at 30° C., the crude mass was quenched with water (20 mL) and the aqueous layer was extracted with ethyl acetate (3×75 mL). The aqueous layer was saturated with sodium chloride and re-extracted with ethyl acetate (3×75 mL). The organic layers were combined, dried over anhydrous sodium sulfate, filtered and evaporated under reduced pressure to yield 2.4 g of crude oil, which was purified by preparative HPLC to yield 430 mg (66%) of 99% pure product. $^1$H NMR δ(300 MHz,CD3OD) 0.92-0.98 (2H,m), 1.28 (1H,m), 1.76-1.87 (3H,m), 2.08-2.14 (2H,m), 2.57-2.75 (3H,m), 3.98-4.04 (1H,m),7.10-7.15 (1H,m), 7.35-7.42 (2H, m). $^{13}$CNMR(CD3OD) δ: 145.91, 133.24, 131.51, 130.79, 129.78, 129.29, 127.58, 127.05, 54.33, 40.53, 37.67, 35.75, 34.36, 33.54, 31.10, 28.25, 26.08, 25.84, 18.53. Purity: 99.53% (a/a) by HPLC. MS, M+(241).

(3) (1R,5R)-1-(1-naphthyl)bicyclo[3.1.0]hexan-3-amine

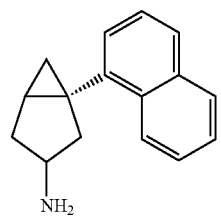

To a solution of (1R,5R)-1-(1-naphthyl)bicyclo[3.1.0]hexan-3-one (480 mg, 2.1 mmol) in methanol (60 mL) was added ammonium acetate (16.8 g, 210 mmol), stirred for 15 min at room temperature and sodium cyanoborohydride (1.08 g, 17 mmol) and the mixture was heated to 60° C. for 2 hours. The reaction was monitored by TLC (ethyl acetate/methanol/triethylamine(89:10:1)). The reaction mixture was concentrated under reduced pressure to remove methanol at 30° C., the crude mass was quenched with water (25 mL) and the aqueous layer was extracted with ethyl acetate (3×100 mL). The aqueous layer was saturated with sodium chloride and re-extracted with ethyl acetate (3×100 mL). The organic layers were combined, dried over anhydrous sodium sulfate, filtered and evaporated under reduced pressure to yield 1.5 g of crude oil, which was purified by preparative HPLC to give 280 mg (58%) of 99% pure product. $^1$H NMR δ(300 MHz, CD3OD): 1.10-1.23 (2H,m), 1.86-1.98 (2H,m) 2.25-2.31 (1H,m), 2.44-2.51 (1H,m), 2.90 (1H,m), 4.06-4.08 (1H,m), 7.33-7.56 (4H,m), 7.71-7.74 (1H,d,6 Hz), 7.82-7.85 (1H, d, 9 Hz), 8.20-8.28 (1H, m). $^{13}$CNMR(CD3OD): 140.75, 140.30, 135.49, 135.44, 133.92, 129.78, 128.61, 127.75, 127.09, 127.00, 126.72, 126.67, 126.58, 126.52, 125.68, 54.95, 43.05, 40.40, 36.35, 34.52, 33.88, 33.64, 25.86, 24.94, 23.70, 15.70.

Purity: 98.04% (a/a) by HPLC. MS, M+(224).

HCl Salt: To a solution of (1R,5R)-1-(1-naphthyl)bicyclo[3.1.0]hexan-3-amine (350 mg, 1.56 mmol) in diethyl ether (10 mL) was added HCl/diethylether (2 mL) solution at 0° C. and stirred for 30 min at room temperature. The slurry mass was filtered and washed with diethyl ether (10 mL) and dried under vacuum for 12 hours to yield white solid (300 mg). $^1$H NMR δ(300 MHz,CD3OD): 1.15-1.17 (1H,m), 1.24 (1H,m), 1.88-1.92 (2H,m), 2.25-2.32 (1H,m), 2.49-2.53 (1H,m), 2.93 (1H,m), 4.11 (1H,m), 7.37-7.57 (4H,m), 7.74-7.76 (1H,d,6 Hz), 7.85-7.88 (1H,d,9 Hz), 8.21-8.30 (1H,m). $^{13}$CNMR (CD3OD): 40.74, 140.30, 135.52, 133.92, 129.82, 128.65, 127.14, 127.01, 126.75, 126.54, 125.69, 55.02, 43.09, 40.43, 36.17, 34.54, 33.93, 25.88, 24.99, 23.70, 15.76.

Purity: 99.63% a/a by HPLC. MS, M+(224).

(4) (1S,5S)-1-(1-naphthyl)bicyclo[3.1.0]hexan-3-amine

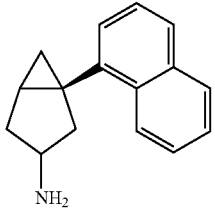

To a solution of (1S,5S)-1-(1-naphthyl)bicyclo[3.1.0]hexan-3-one (0.7 g, 3.1 mmol) in methanol (87.5 mL) was added ammonium acetate (24.3 g, 310 mmol), stirred for 15 minutes at room temperature and sodium cyanoborohydride (1.58 g, 25 mmol) was added and the mixture was heated to 60° C. for 2 hours. The reaction was monitored by TLC (ethyl acetate/methanol/triethylamine (89:10:1)). The reaction mixture was concentrated under reduced pressure to remove methanol at 30° C., the crude mass was quenched with water (50 mL). The aqueous layer was extracted with ethyl acetate (3×150 mL). The aqueous layer was saturated with sodium chloride and re-extracted with ethyl acetate (3×150 mL). The organic layers were combined, dried over anhydrous sodium sulfate, filtered and evaporated under reduced pressure to yield 2.4 g of crude oil, which was purified by preparative HPLC to 400 mg (57%) of 99% pure product. $^1$H NMR δ(300 MHz,CD3OD): 1.1-1.15 (1H,m), 1.21-1.24 (1H,m), 1.88-1.93 (2H,m), 2.24-2.31 (1H,m), 2.45-2.57 (1H,m), 2.90-2.92 (1H,m), 4.10-4.2 (1H,m), 7.37-7.57 (4H,m), 7.74-7.76 (1H,d, 6 Hz), 7.85-7.88 (1H,d,9 Hz), 8.20-8.29 (1H,m). $^{13}$CNMR (CD3OD): 140.74, 140.30, 135.51, 133.93, 129.81, 128.64, 127.76, 127.12, 127.01, 126.74, 126.59, 125.67 119.93, 54.97, 43.08, 40.42, 36.16, 34.53, 33.91, 25.88, 24.94, 23.70, 15.76. Purity: 98.5% (a/a) by HPLC. MS, M+(224).

HCl Salt: To a solution of (1S,5S)-1-(1-naphthyl)bicyclo[3.1.0]hexan-3-amine (500 mg, 1.56 mmol) in diethyl ether (10 mL) was added HCl/diethylether (2 mL) solution at 0° C. and stirred for 30 min at room temperature. The slurry mass was filtered and washed with diethyl ether (10 mL) and dried under vacuum for 12 hours to yield white solid (350 mg). $^1$H NMR δ(300 MHz,CD3OD): 1.10-1.23 (2H,m), 1.86-1.98 (2H,m), 2.25-2.31 (1H,m), 2.44-2.51 (1H,m), 2.90 (1H,m), 4.06-4.08 (1H,m),7.33-7.56 (4H,m),7.71-7.74 (1H,d,6 Hz), 7.82-7.85 (1H,d,9 Hz), 8.20-8.28 (1H,m). $^{13}$CNMR (CD3OD): 140.75, 140.31, 135.49, 135.44, 133.91, 129.79, 128.62, 127.75, 127.12, 127.01, 126.73, 126.67, 126.59, 126.53, 125.70, 55.02, 43.06, 40.39, 36.15, 34.52, 33.90, 31.65, 25.87, 24.99, 23.68, 15.76. Purity: 99.09% (a/a) by HPLC. MS, M+(224).

H. Separation of diastereomers of (1R,5R)-1-(3,4-dichlorophenyl)bicyclo[3.1.0]hexan-3-amine The free base was purified by preparative chiral HPLC (CHIRALPAK AD column, 5×50 cm 20 µm, mobile phase heptane/ethanol 97:3 pre-mix, flow rate 118 mL/min, uv 230 nm). The free base was dissolved in 70:30 heptane/ethanol. Injections of 10 mL of the solution (85 mg) and elution provided separation of the diastereomers (fractions analyzed by chiral HPLC and pure fractions mixed and concentrated in vacuo). Mixed fractions were combined and re-dissolved in mobile phase and separated. The residue was dried under vacuum overnight (50° C.).

The COSY 2D NMR spectrum was obtained to verify the assignments of all protons. With this information in hand, a 1D nOe difference experiment was performed (irradiating on the methine proton) and, for the 2nd diastereomers, a large enhancement between the cyclopropyl methylene and the aminocyclopentane methine proton was observed. Therefore, this diastereomer is the isomer corresponding to 1R,3R,5R diastereomer.

(1) (1R,3S,5R)-1-(3,4-Dichlorophenyl)bicyclo[3.1.0]hexan-3-amine

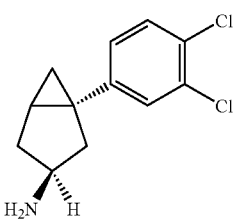

1$^{st}$ diastereome is 93 mg (55%): $^1$H NMR (300 MHz, CDCl$_3$) δ 7.29 (d, J=8 Hz, 1H), 7.22 (d, J=2 Hz, 1H), 6.95 (dd, J=8, 2 Hz, 1H), 3.85-3.65 (m, 1H), 2.45-2.20 (m, 2H), 1.85 (dd, J=4, 4 Hz, 1H), 1.70-1.60 (m, 1H), 1.55 (dd, J=14, 4 Hz, 1H), 1.22 (t, J=7 Hz, 1H), 1.00-0.90 (m, 1H); MS (ESI) m/z 242 [M+H]$^+$; Chiral HPLC (Method 2) 98.2% (AUC), t$_R$=9.02 min.

HCl Salt: A stirred solution of (1R,5R)-1-(3,4-dichlorophenyl)bicyclo[3.1.0]hexan-3-amine from 1$^{st}$ eluted diastereomer (93 mg, 0.38 mmol) in methanol (10 mL), was added aqueous HCl (0.18 mL, 2.0 M, 0.38 mmol). The mixture was concentrated in vacuo to afford 103 mg (96%) of white solid: $^1$H NMR (500 MHz, CD$_3$OD) δ 7.42 (d, J=8 Hz, 1H), 7.38 (d, J=2 Hz, 1H), 7.14 (dd, J=8, 2 Hz, 1H), 4.10-3.09 (m, 1H), 2.80-2.60 (m, 2H), 2.12 (dd, J=14, 4 Hz, 1H), 1.90-1.83 (m, 1H), 1.80 (dd, J=14, 4 Hz, 1H), 1.28 (t, J=7 Hz, 1H), 0.99 (t, J=7 Hz, 1H); $^{13}$C NMR (125 MHz, CD$_3$OD) δ 145.89, 133.26, 131.45, 130.83, 129.82, 127.60, 54.37, 40.57, 35.78, 34.39, 28.25, 25.85; MS (ESI) m/z 242 [M+H]$^+$; HPLC (Method 1)>99% (AUC), t$_R$=11.91 min; Chiral HPLC (Method 2) 97.4% (AUC), t$_R$=9.19 min; Optical Rotation [α]$^{25}_D$+82.3°; Melting Point 222-225° C.

(2) (1R,3R,5R)-1-(3,4-Dichlorophenyl)bicyclo[3.1.0]hexan-3-amine

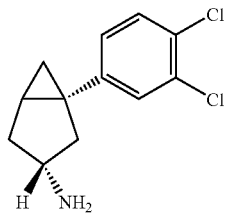

2$^{nd}$ diastereome is 27 mg (16%): $^1$H NMR (300 MHz, CDCl$_3$) δ 7.31 (d, J=8 Hz, 1H), 7.21 (d, J=2 Hz, 1H), 6.95 (dd, J=8, 2 Hz, 1H), 3.25-3.00 (m, 1H), 2.50-2.35 (m, 1H), 2.25-

2.15 (m, 1H), 1.80-1.50 (m, 2H), 1.90-1.83 (m, 1H), 0.90 (t, J=5 Hz, 1H), 0.80-0.60 (m, 1H); MS (ESI) m/z 242 [M+H]+; Chiral HPLC (Method 2) 98.9% (AUC), $t_R$=13.47 min.

HCl Salt: A stirred solution of (1R,5R)-1-(3,4-dichlorophenyl)bicyclo[3.1.0]hexan-3-amine from $2^{nd}$ eluted diastereomer (27 mg, 0.11 mmol) in methanol (2 mL), was added aqueous HCl (0.06 mL, 2.0 M, 0.12 mmol). The mixture was concentrated in vacuo to afford 31 mg (99%) of off-white solid: $^1$H NMR (500 MHz, CD$_3$OD) δ 7.43 (d, J=8 Hz, 1H), 7.36 (d, J=2 Hz, 1H), 7.13 (dd, J=8, 2 Hz, 1H), 3.50-3.40 (m, 1H), 2.67-2.58 (m, 1H), 2.40-2.30 (m, 1H), 2.15-2.00 (m, 2H), 1.90-1.83 (m, 1H), 1.01 (t, J=5 Hz, 1H), 0.93 (t, J=7 Hz, 1H); $^{13}$C NMR (125 MHz, CD$_3$OD) δ 145.82, 133.27, 131.51, 130.72, 129.33, 127.09, 49.57, 37.73, 33.60, 31.14, 26.10, 18.55; MS (ESI) m/z 242 [M+H]+; HPLC (Method 1) 98.2% (AUC), $t_R$=12.00 min; Chiral HPLC (Method 2)>99% (AUC), $t_R$=13.49 min; Optical Rotation [α]$^{25}_D$+68.4°; Melting Point 218-220° C.

I. Separation of Diastereomers of (1R,5R)-1-(1-naphthyl)bicyclo[3.1.0]hexan-3-amine The free base was purified by preparative chiral HPLC (CHIRALPAK AD column, 5×50 cm 20 μm, mobile phase heptane/ethanol 97:3 pre-mix, flow rate 118 mL/min, uv 230 nm). The free base was dissolved in 70:30 heptane/ethanol. Injections of 10 mL of the solution (85 mg) and elution provided separation of the diastereomers (fractions analyzed by chiral HPLC and pure fractions mixed and concentrated in vacuo). Mixed fractions were combined and re-dissolved in mobile phase and separated. The residue was dried under vacuum overnight (50° C.).

The COSY 2D NMR spectrum was obtained to verify the assignments of all protons. With this information in hand, a 1D nOe difference experiment was performed (irradiating on the methine proton) and, for the 2nd diastereomers, a large enhancement between the cyclopropyl methylene and the aminocyclopentane methine proton was observed. Therefore, this diastereomer is the isomer corresponding to 1R,3R,5R diastereomer.

(1) (1R,3S,5R)-1-(1-naphthyl)bicyclo[3.1.0]hexan-3-amine

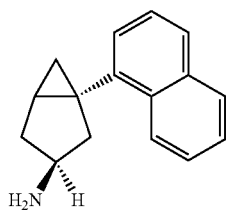

$1^{st}$ diastereome is 93 mg (54%): $^1$H NMR (300 MHz, CDCl$_3$) δ 8.26 (d, J=7 Hz, 1H), 7.85 (d, J=7 Hz, 1H), 7.71 (d, J=7 Hz, 1H), 7.60-7.30 (m, 4H), 3.90-3.70 (m, 1H), 2.71-2.58 (m, 1H), 2.44-2.30 (m, 1H), 1.98 (dd, J=14, 4 Hz, 1H), 1.80-1.60 (m, 2H), 1.39 (t, J=7 Hz, 1H), 1.10-1.00 (m, 1H); MS (ESI) m/z 224 [M+H]+; Chiral HPLC (Method 2)>99% (AUC), $t_R$=6.96 min.

HCl Salt: A stirred solution of (1R,5R)-1-(naphthalen-1-yl)bicyclo[3.1.0]hexan-3-amine from $1^{st}$ eluted diastereomer (93 mg, 0.42 mmol) in methanol (10 mL), was added aqueous HCl (0.21 mL, 2.0 M, 0.42 mmol). The mixture was concentrated in vacuo to afford 107 mg (99%) of white solid: $^1$H NMR (500 MHz, CD$_3$OD) δ 8.23 (d, J=7 Hz, 1H), 7.88 (d, J=7 Hz, 1H), 7.76 (d, J=7 Hz, 1H), 7.58-7.53 (m, 1H), 7.52-7.47 (m, 1H), 7.44 (dd, J=7, 2 Hz, 1H), 7.39 (t, J=7 Hz, 1H), 4.18-4.08 (m, 1H), 3.00-2.88 (m, 1H), 2.60-2.50 (m, 1H), 2.28 (dd, J=14, 4 Hz, 1H), 2.00-1.85 (m, 2H), 1.25 (t, J=7 Hz, 1H), 1.14 (t, J=7 Hz, 1H); $^{13}$C NMR (125 MHz, CD$_3$OD) δ 140.75, 135.59, 133.97, 129.90, 128.73, 127.20, 127.07, 126.81, 126.59, 125.70, 55.06, 43.17, 36.25, 34.61, 25.95, 25.04; MS (ESI) m/z 224 [M+H]+; HPLC (Method 1)>99% (AUC), $t_R$=11.45 min; Chiral HPLC (Method 2)>99% (AUC), $t_R$=7.06 min; Optical Rotation [α]$^{25}_D$+51.5°; Melting Point 203-205° C.

(2) (1R,3R,5R)-1-(1-naphthyl)bicyclo[3.1.0]hexan-3-amine

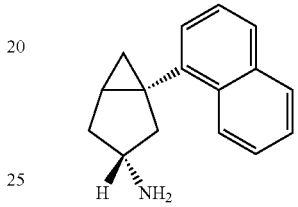

$2^{nd}$ diastereomer is 24 mg (14%): $^1$H NMR (300 MHz, CDCl$_3$) δ 8.30 (d, J=7 Hz, 1H), 7.85 (d, J=7 Hz, 1H), 7.72 (d, J=7 Hz, 1H), 7.60-7.30 (m, 4H), 3.40-3.20 (m, 1H), 2.60-2.50 (m, 1H), 2.40-2.30 (m, 1H), 2.02-1.90 (m, 1H), 1.82-1.62 (m, 2H), 1.01 (t, J=7 Hz, 1H), 0.82-0.72 (m, 1H); Chiral HPLC (Method 2) 98.5% (AUC), $t_R$=9.87 min.

HCl Salt: A stirred solution of (1R,5R)-1-(naphthalen-1-yl)bicyclo[3.1.0]hexan-3-amine from $2^{nd}$ eluted diastereomer (24 mg, 0.11 mmol) in methanol (2 mL), was added aqueous HCl (0.06 mL, 2.0 M, 0.12 mmol). The mixture was concentrated in vacuo to afford 29 mg (103%) of off-white solid: $^1$H NMR (500 MHz, CD$_3$OD) δ 8.29 (d, J=7 Hz, 1H), 7.88 (d, J=7 Hz, 1H), 7.77 (d, J=7 Hz, 1H), 7.58-7.46 (m, 3H), 7.41 (t, J=7 Hz, 1H), 3.60-3.48 (m, 1H), 2.80-2.68 (m, 1H), 2.55-2.48 (m, 1H), 2.40-2.28 (m, 1H), 2.05 (t, J=7 Hz, 1H), 1.90-1.82 (m, 1H), 1.15 (t, J=7 Hz, 1H), 0.89 (t, J=7 Hz, 1H); $^{13}$C NMR (125 MHz, CD$_3$OD) δ 138.79, 134.01, 132.47, 128.36, 127.24, 125.48, 125.23, 125.12, 124.17, 48.48, 38.79, 32.47, 30.20, 22.21, 14.29; MS (ESI) m/z 224 [M+H]+; HPLC (Method 1) 98.4% (AUC), $t_R$=11.60 min; Chiral HPLC (Method 2) 98.3% (AUC), $t_R$=10.13 min; Optical Rotation [α]$^{25}_D$+49.2°; Melting Point 260-263° C.

EXAMPLE X

Activity Selectivity, and Potency of Arylbicyclo[3.1.0]hexylamines for Inhibiting Monoamine Neurotransmitter Transport The effects of arylbicyclo[3.1.0]hexylamines of the invention for inhibiting transport of norepinephrine (NE) and/or dopamine (DA) and/or serotonin (5-HT) were evaluated using preparations of synaptosomes from different regions of the rat brain according to previously-reported techniques. [Perovic, S. and Muller, W. E., Arzneimittelforschung 45: 1145-1148 (1995); Janowsky, A. et al., J. Neurochem. 46: 1272-1276 (1986)] The subject assay methods are art-accepted models for generally assessing and predicting activities of drugs that modulate biogenic amine transport in mammals.

Whole brains were obtained from normal rats, and synaptosomal preparations were made from either whole brain (5-HT), striatum (DA) or hypothalamus (NE) by gentle disruption in 10 volumes (w/v) of 0.32 M sucrose (0-4° C.) using a Teflon-glass homogenizer. The homogenate was then centrifuged at 1000×g for 10 min. The supernatant was retained and centrifuged at 23000 g for 20 min. The resulting pellet was gently resuspended in 200 volumes of 0.32 M sucrose (0-4° C.) using a teflon-glass homogenizer. Aliquots (250 µL) of this preparation were added to tubes, along with 0.2 µCi/mL of [$^3$H]5-HT, [$^3$H]DA, or [$^3$H]NE, 200 µL of selected 1-arylbicyclo[3.1.0]hexanamine test compounds (to yield final concentrations of 500 nM) and 1 mL of Krebs-Ringer bicarbonate buffer (pH 7.4). The mixtures were incubated for either 15 (DA and 5-HT uptake) or 20 (NE uptake) minutes at 37° C. At the end of this period, the assay was terminated by rapid filtration over Whatman GF/C glass fiber filters. The filters were rinsed 3 times with 4 ml of Krebs-Ringer bicarbonate buffer (0-4° C.), and the radioactivity retained on the filters was measured by liquid scintillation spectrometry. The results of these assays are shown in Table 2, below, which indicates, for each of the exemplary, the structure of the substituent, and levels of observed uptake inhibition percentage for each of the indicated neurotransmitters.

TABLE 2

Inhibition of Biogenic Amine Uptake By Exemplary Substituted Arylbicyclo[3.1.0.]hexylamines

| Structure | Uptake Inhibition % at 500 nM | | | Uptake IC50 (nM) | | |
|---|---|---|---|---|---|---|
| | NE | 5-HT | DA | NE | 5-HT | DA |
| 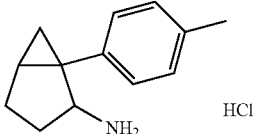 | 14 | 20 | 18 | | | |
| 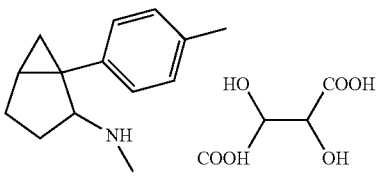 | 8 | 4 | 33 | | | |
| 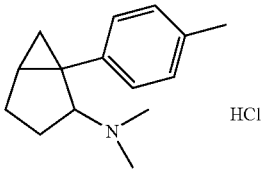 | 71 | 0 | 70 | 2090 | >5000 | 335 |
| 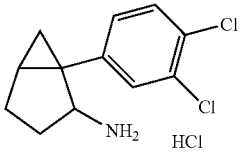 | 34 | 5 | 86 | | | |
| 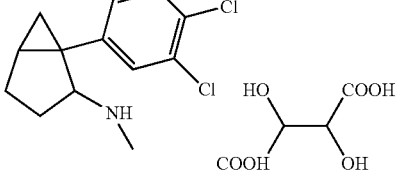 | 94 | 15 | 101 | 18 | 3680 | 3 |
| 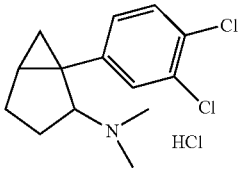 | 96 | 38 | 99 | 11 | 1240 | 9 |

TABLE 2-continued

Inhibition of Biogenic Amine Uptake By Exemplary Substituted Arylbicyclo[3.1.0.]hexylamines

| Structure | Uptake Inhibition % at 500 nM | | | Uptake IC50 (nM) | | |
|---|---|---|---|---|---|---|
| | NE | 5-HT | DA | NE | 5-HT | DA |
| | 38 | 21 | 44 | | | |
| | 73 | 69 | 43 | | | |
| | 50 | 66 | 0 | | | |
| | 76 | 89 | 77 | 126 | 38 | 111 |
| | 92 | 95 | 95 | 83 | 37 | 60 |
| | 59 | 75 | 83 | 454 | 172 | 283 |
| | 60 | 92 | 65 | 464 | 82 | 312 |

TABLE 2-continued

Inhibition of Biogenic Amine Uptake By Exemplary Substituted Arylbicyclo[3.1.0.]hexylamines

| Structure | Uptake Inhibition % at 500 nM | | | Uptake IC50 (nM) | | |
|---|---|---|---|---|---|---|
| | NE | 5-HT | DA | NE | 5-HT | DA |
| (3,4-dichlorophenyl bicyclo[3.1.0]hexyl-N,N-dimethylamine HCl) | 40 | 95 | 48 | | | |
| (1-naphthyl bicyclo[3.1.0]hexyl-amine HCl) | 76 | 65 | 53 | 282 | 425 | 496 |
| (1-naphthyl bicyclo[3.1.0]hexyl-amine HCl, isomer) | 42 | 74 | 39 | | | |
| (1-naphthyl bicyclo[3.1.0]hexyl-N-methylamine HCl) | 81 | 82 | 23 | 74 | 76 | 8730 |
| (1-naphthyl bicyclo[3.1.0]hexyl-N,N-dimethylamine HCl) | 50 | 83 | 17 | 805 | 70 | >10,000 |

TABLE 2-continued
Inhibition of Biogenic Amine Uptake By Exemplary Substituted Arylbicyclo[3.1.0.]hexylamines
| Structure | Uptake Inhibition % at 500 nM | | | Uptake IC50 (nM) | | |
|---|---|---|---|---|---|---|
| | NE | 5-HT | DA | NE | 5-HT | DA |
| 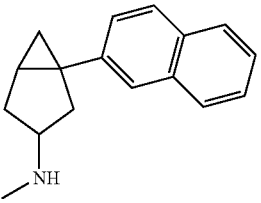 | 56 | 95 | 66 | 339 | 35 | 221 |
| 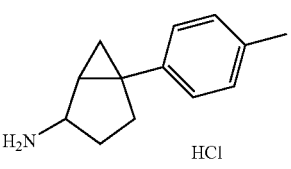 | 50 | 25 | 31 | | | |
| 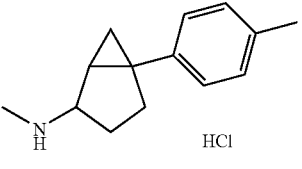 | 89 | 37 | 63 | 313 | 1190 | 858 |
| 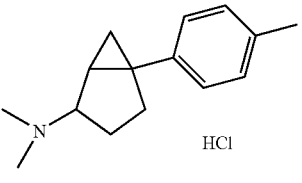 | 57 | 44 | 55 | | | |
| 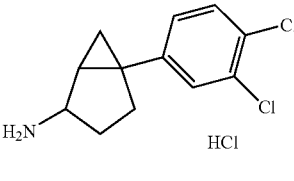 | 35 | 53 | 29 | | | |
| 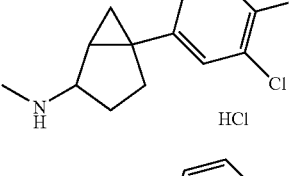 | 63 | 94 | 56 | 444 | 75 | 360 |
| 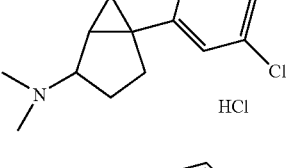 | 29 | 95 | 34 | | | |
| 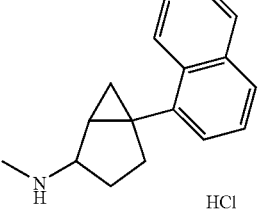 | 49 | 90 | 29 | | | |

TABLE 2-continued

Inhibition of Biogenic Amine Uptake By Exemplary
Substituted Arylbicyclo[3.1.0.]hexylamines

| Structure | Uptake Inhibition % at 500 nM | | | Uptake IC50 (nM) | | |
|---|---|---|---|---|---|---|
| | NE | 5-HT | DA | NE | 5-HT | DA |
| (1-naphthyl structure, HCl) | 25 | 76 | 15 | | | |
| (2-naphthyl structure, NH, HCl) | 47 | 90 | 45 | | | |
| (2-naphthyl structure, N-methyl, HCl) | 26 | 96 | 42 | | | |

Readily discernable from the foregoing results is the high degree of diversity with respect to the biological activity changes that were achieved by differentially altering substituents to yield novel arylbicyclo[3.1.0]hexylamines according to the invention—whereby the absolute potency at any one transporter may be altered dramatically, and in distinct patterns among the exemplified compounds. Radical changes in the potency ratio were evinced among the exemplary arylbicyclo[3.1.0]hexylamine compounds. The differential potency ratios for inhibition of neurotransmitter uptake affecting dopamine, serotonin, and norepinephrine transport yield profound and distinct therapeutic potentials among the different, novel compounds of the invention. Both the absolute changes in potency and the changes in potency "ratio" demonstrated herein for exemplary compounds of the invention would not have been expected or predictable with a reasonable expectation of success by persons of ordinary skill in the art The data provided in Table 2 demonstrate that several of the exemplary arylbicyclo[3.1.0]hexylamines are potent inhibitors of norepinephrine and/or serotonin and/or dopamine uptake. As such, the compounds and related formulations and methods of the invention provide neurobiologically active tools for modulating biogenic amine transport in mammalian subjects. These subjects may include in vitro or ex vivo mammalian cell, cell culture, tissue culture, or organ explants, as well as human and other mammalian individuals presenting with, or at heightened risk for developing, a central nervous system (CNS) disorder, including neuropsychiatric disorders such as anxiety, or depression.

In certain embodiments, neurobiologically active compositions comprising an arylbicyclo[3.1.0]hexylamine of the invention are effective to inhibit cellular uptake of norepinephrine in a mammalian subject. In other embodiments, these compositions will effectively inhibit cellular uptake of serotonin in mammals. Other compositions of the invention will be effective to inhibit cellular uptake of dopamine in mammalian subjects.

As illustrated by the foregoing examples, additional neurobiologically active compositions of the invention will be effective to inhibit cellular uptake of multiple biogenic amine neurotransmitters in mammalian subjects, for example, norepinephrine and serotonin, norepinephrine and dopamine, or serotonin and dopamine. In additional embodiments, the compositions of the invention are effective to inhibit cellular uptake of norepinephrine, serotonin and dopamine in mammalian subjects.

In further-detailed embodiments, as exemplified by the results presented in Table 2, neurobiologically active compositions of the invention surprisingly inhibit cellular reuptake of two, or three, biogenic amines selected from norepinephrine, serotonin and dopamine in a mammalian subject "nonuniformly" across an affected range of multiple biogenic amine targets. The distinct double and triple reuptake inhibition activity profiles demonstrated herein for exemplary compounds of the invention illustrate the powerful and unpredictable nature of the subject, compounds, and further evince the ability to follow the teachings of the present disclosure to produce, select, and employ other substituted arylbicyclo[3.1.0]hexylamines according to the invention having distinct activity profiles to fulfill additional therapeutic uses within the invention for treating diverse CNS disorders.

In exemplary embodiments, differential reuptake inhibition mediated by the compounds of the invention may yield a profile/ratio of reuptake inhibition activities for all three neurotransmitters, norepinephrine, dopamine, and serotonin, respectively, in reuptake inhibition profiles/ratios as exemplified in Table 2, selected from the following approximate inhibition profiles/ratios: (2:1:1); (3:10:1); (2:5:1); (12:1:5); (15:1:12); (3:8:5); (2:4:1); (3:1:2); and (2:4:1). Although these values are approximate, they will correlate in a measurable way with novel in vivo reuptake inhibition profiles/ratios as will be readily determined by those skilled in the art.

In related embodiments, neurobiologically active compositions of the invention inhibit cellular uptake of two, or three, biogenic amine neurotransmitters non-uniformly, for example by inhibiting uptake of at least one member of a group of transmitters including norepinephrine, serotonin, and dopamine by a factor of two- to ten-fold greater than a potency of the same composition to inhibit uptake of one or more different neurotransmitter(s). In exemplary embodiments, compositions of the invention comprising arylbicyclo[3.1.0]hexylamines, inhibit cellular uptake of serotonin by a factor of at least approximately two-fold, three-fold, five-fold, ten-fold or greater compared to a potency of the same composition to inhibit uptake of norepinephrine, dopamine, or both norepinephrine and dopamine. In other exemplary embodiments, different arylbicyclo[3.1.0]hexylamines of the invention inhibit cellular uptake of dopamine by a factor of at least approximately two-fold, three-fold, five-fold, ten-fold or greater compared to a potency of the composition for inhibiting uptake of norepinephrine, serotonin, or both norepinephrine and serotonin. In additional exemplary embodiments, the compositions described herein inhibit cellular uptake of norepinephrine by a factor of at least approximately two-fold, three-fold, five-fold, ten-fold or greater compared to a potency of the same composition for inhibiting uptake of serotonin. In different exemplary embodiments, compositions are provided that inhibit cellular uptake of dopamine by a factor of at least approximately two-fold, three-fold, five-fold, ten-fold or greater compared to a potency of the composition for inhibiting uptake of serotonin. In yet additional embodiments, neurobiologically active compositions are provided that exhibit approximately equivalent potency for inhibiting cellular uptake of norepinephrine and serotonin, while at the same time inhibiting dopamine uptake by a factor of at least approximately two-fold, three-fold, five-fold, ten-fold or greater compared to a potency of the composition for inhibiting uptake of norepinephrine and serotonin. In still other exemplary embodiments, compositions of the invention exhibit approximately equivalent potency for inhibiting cellular uptake of serotonin and dopamine, while at the same time inhibiting norepinephrine by a factor of no greater than approximately half the potency for inhibiting uptake of serotonin and dopamine. In certain embodiments, compositions of the invention exhibit approximately equivalent potency for inhibiting cellular uptake of norepinephrine, serotonin, and dopamine.

Compounds of the invention that inhibit uptake of norepinephrine and/or, serotonin, and/or dopamine have a wide range of therapeutic uses, principally to treat CNS disorders, including various neuropsychiatric disorders, as described above. Certain CNS disorders contemplated herein will be more responsive to a compound of the invention that preferentially inhibits, for example, dopamine uptake relative to norepinephrine and/or serotonin uptake, as in the case of some forms of depression. Other disorders will be determined to be more responsive to compounds of the invention that more potently inhibit norepinenephrine reuptake relative to serotonin reuptake and dopamine reuptake. Other CNS disorders, for example, attention deficit hyperactivity disorder (ADHD), may respond better to compounds of the invention that preferentially inhibit dopamine and norepinephrine reuptake relative to serotonin reuptake. Thus, the host of exemplary compounds described herein, which provide a range of reuptake inhibition profiles/ratios, will provide useful drug candidates for a diverse range of CNS disorders, and will effectively treat specific disorders with lower side effect profiles than currently available drugs.

It will be understood that the instant invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

REFERENCES

Skolnick, P. et al Eur. J. Pharmacol. 461:99 (2003)
Skolnick, P. et al., Life Sci. 73: 3175-3179 (2003)
Bulletin Chem. Soc. Japan 62: 2728 (1989)
Yong, W. et al., Synlett 9: 911-912 (1996)
McBriar, M. D. et al., J. Med. Chem. 49: 2294-2310 (2006)
"Nitrogen Protecting Groups in Organic Synthesis", John Wiley and Sons, New York, N.Y., 1981, Chapter 7
"Nitrogen Protecting Groups in Organic Chemistry", Plenum Press, New York, N.Y., 1973, Chapter 2
Green, T. W. and Wuts, P. G. M. in "Protective Groups in Organic Chemistry", 3rd edition, John Wiley & Sons, New York, N.Y., 1999
Quick Reference to the Diagnostic Criteria From DSM-IV (Diagnostic and Statistical Manual of Mental Disorders, Fourth Edition), The American Psychiatric Association, Washington, D.C., 1994
Perovic, S, and Muller, W. E., Arzneimittelforschung 45: 1145-1148 (1995)
Janowsky, A. et al., J. Neurochem. 46: 1272-1276 (1986)
Skolnick, P., Basile, A. and Chen, Z., International Patent Application, Pub. No. WO/2006/098101; Sep. 14, 2006
U.S. Pat. No. 6,132,724; Blum; Oct. 17, 2000
U.S. Pat. No. 4,122,193; Scherm et al.; Oct. 24, 1978

What is claimed is:

1. A method for treating a central nervous system (CNS) disorder selected from the group consisting of depression, an anxiety disorder, an attention deficit disorder, substance abuse, and an eating disorder in a mammalian subject comprising administering to said subject an effective amount of a compound sufficient to treat said CNS disorder, or to alleviate the CNS disorder wherein the compound is 1-p-tolylbicyclo [3.1.0]hexan-2-amine; N-methyl-1-p-tolylbicyclo[3.1.0] hexan-2-amine; N,N-dimethyl-1-p-tolylbicyclo[3.1.0] hexan-2-amine; 1-(3,4-dichlorophenyl)bicyclo[3.1.0]hexan-2-amine; 1-(3,4-dichlorophenyl)-N-methylbicyclo[3.1.0] hexan-2-amine; 1-(3,4-dichlorophenyl)-N,N-dimethylbicyclo[3.1.0]hexan-2-amine; 1-p-tolylbicyclo [3.1.0]hexan-3-amine; N-methyl-1-p-tolylbicyclo[3.1.0] hexan-3-amine; N,N-dimethyl-1 -p-tolylbicyclo[3.1.0] hexan-3-amine; 1-(3,4-dichlorophenyl)bicyclo[3.1.0]hexan- 3-amine; 1-(3,4-dichlorophenyl)-N-methylbicyclo[3.1.0]hexan-3-amine; 1-(3,4-dichlorophenyl)-N,N-dimethylbicyclo[3.1.0]hexan-3-amine; 5-p-tolylbicyclo[3.1.0]hexan-2-amine; N-methyl-5-p-tolylbicyclo [3.1.0]hexan-2-amine; N,N-dimethyl-5-p-tolylbicyclo[3.1.0]hexan-2-amine; 5-(3,4-dichlorophenyl)bicyclo[3.1.0]hexan-2-amine; 5-(3,4-dichlorophenyl)-N-methylbicyclo[3.1.0]hexan-2-amine; and 5-(3,4-dichlorophenyl)-N,N-dimethylbicyclo[3.1.0]hexan-2-amine, N-methyl-1-(naphthalen-1-yl)bicyclo[3.1.0]hexan-3-amine; N,N-dimethyl-1-(naphthalen-1-yl)bicyclo[3.1.0]hexan-3-amine; N-methyl-1-(naphthalen-2-yl) bicyclo[3.1.0]hexan-3-amine; N-methyl-5-(naphthalen-1-yl)bicyclo[3.1.0]hexan-2-amine; N,N-dimethyl-5-(naphthalen-1-yl)bicyclo[3.1.0]hexan-2-amine; N-methyl-5-(naphthalen-2-yl)bicyclo[3.1.0]hexan-2-amine; and N,N-dimethyl-5-(naphthalen-2-yl)bicyclo[3.1.0]hexan-2-amine, or pharmaceutically acceptable salts, enantiomers, hydrates, and combinations thereof.

2. A method for treating a central nervous system (CNS) disorder selected from the group consisting of depression, an anxiety disorder, an attention deficit disorder, substance abuse, and an eating disorder in a mammalian subject comprising administering to said subject an effective amount of a composition according to claim 1 in a pharmaceutically acceptable carrier or excipient sufficient to treat said CNS disorder, or to alleviate the CNS disorder.

* * * * *